US008480569B2

(12) United States Patent
Terliuc et al.

(10) Patent No.: US 8,480,569 B2
(45) Date of Patent: Jul. 9, 2013

(54) FLEXIBLE ENDOSCOPE SYSTEM AND FUNCTIONALITY

(75) Inventors: Gad Terliuc, Ra'anana (IL); Gilad Luria, Givatayim (IL); Ohad Shafran, Hof Hacarmel (IL)

(73) Assignee: Smart Medical Systems Ltd., Ra'anana (IL)

(*) Notice: Subject to any disclaimer, the term of this patent is extended or adjusted under 35 U.S.C. 154(b) by 1082 days.

(21) Appl. No.: 12/301,094

(22) PCT Filed: May 17, 2007

(86) PCT No.: PCT/IL2007/000600
§ 371 (c)(1),
(2), (4) Date: Jan. 20, 2009

(87) PCT Pub. No.: WO2007/135665
PCT Pub. Date: Nov. 29, 2007

(65) Prior Publication Data
US 2009/0187069 A1  Jul. 23, 2009

Related U.S. Application Data

(60) Provisional application No. 60/801,057, filed on May 18, 2006, provisional application No. 60/801,058, filed on May 18, 2006, provisional application No. 60/801,093, filed on May 18, 2006, provisional application No. 60/840,006, filed on Aug. 25, 2006, provisional application No. 60/873,261, filed on Dec. 7, 2006, provisional application No. 60/873,262, filed on Dec. 7, 2006.

(51) Int. Cl.
*A61B 1/00* (2006.01)
*A61B 1/04* (2006.01)

(52) U.S. Cl.
USPC ............ 600/153; 600/114; 600/115; 600/121

(58) Field of Classification Search
USPC .................................. 600/102, 115–116, 153
See application file for complete search history.

(56) References Cited

U.S. PATENT DOCUMENTS

| 4,040,413 A | 8/1977 | Ohshiro |
| 4,066,070 A | 1/1978 | Utsugi |

(Continued)

FOREIGN PATENT DOCUMENTS

| JP | 2003250896 | 9/2003 |
| WO | 8301893 | 6/1983 |

(Continued)

OTHER PUBLICATIONS

Sleeve Expander Tool product, manufactured by Hellermann Tyton of 7930 N. Faulkner Road., Milwaukee, Wisconsin USA, and commercially distributed in the UK by Canford Audio PLC of Crowther Road, Washington, UK under catalog No. 55-601.

(Continued)

*Primary Examiner* — Alireza Nia
(74) *Attorney, Agent, or Firm* — Fish & Richardson P.C.

(57) ABSTRACT

An enhanced flexibility auxiliary endoscope assembly for use with an endoscope, the assembly including at least one flexible elongate element and a flexible sleeve having a first lumen for accommodating a distal portion of an endoscope capable of assuming at least a first curvature and a second lumen for accommodating the at least one flexible elongate element, the second lumen being configured to allow the at least one flexible elongate element to assume the at least first curvature as well as at least a second curvature about the first curvature, thereby to enhance flexibility of the auxiliary endoscope assembly.

24 Claims, 44 Drawing Sheets

U.S. PATENT DOCUMENTS

| | | | |
|---|---|---|---|
| 4,148,307 A | 4/1979 | Utsugi | |
| 4,176,662 A | 12/1979 | Frazer | |
| 4,195,633 A | 4/1980 | Nehring et al. | |
| 4,195,637 A | 4/1980 | Gruntzig et al. | |
| 4,224,929 A | 9/1980 | Furihata | |
| 4,445,892 A | 5/1984 | Hussein et al. | |
| 4,453,545 A | 6/1984 | Inoue | |
| 4,616,652 A | 10/1986 | Simpson | |
| 4,646,722 A | 3/1987 | Silverstein et al. | |
| 4,646,988 A | 3/1987 | Campbell | |
| 4,676,228 A | 6/1987 | Krasner et al. | |
| 4,748,969 A * | 6/1988 | Wardle | 600/150 |
| 4,784,969 A * | 11/1988 | Nitayama | 438/243 |
| 4,807,593 A | 2/1989 | Ito | |
| 4,862,874 A | 9/1989 | Kellner | |
| 4,983,165 A | 1/1991 | Loiterman | |
| 5,025,778 A | 6/1991 | Silverstein et al. | |
| 5,050,585 A | 9/1991 | Takahashi | |
| 5,135,001 A | 8/1992 | Sinofsky et al. | |
| 5,259,366 A | 11/1993 | Reydel et al. | |
| 5,518,501 A | 5/1996 | Oneda et al. | |
| 5,577,992 A | 11/1996 | Chiba et al. | |
| 5,588,424 A * | 12/1996 | Insler et al. | 128/207.15 |
| 5,662,587 A | 9/1997 | Grundfest et al. | |
| 5,679,110 A | 10/1997 | Hamazaki | |
| 5,762,604 A | 6/1998 | Kieturakis | |
| 5,876,329 A | 3/1999 | Harhen | |
| 5,938,586 A | 8/1999 | Wilk et al. | |
| 6,007,482 A * | 12/1999 | Madni et al. | 600/115 |
| 6,161,049 A | 12/2000 | Rudie et al. | |
| 6,162,171 A | 12/2000 | Ng et al. | |
| 6,309,346 B1 | 10/2001 | Farhadi | |
| 6,461,294 B1 | 10/2002 | Oneda et al. | |
| 6,485,409 B1 | 11/2002 | Voloshin et al. | |
| 6,585,639 B1 | 7/2003 | Kotmel et al. | |
| 6,663,589 B1 | 12/2003 | Halevy | |
| 6,702,735 B2 | 3/2004 | Kelly | |
| 6,951,554 B2 | 10/2005 | Johansen et al. | |
| 7,056,284 B2 | 6/2006 | Martone et al. | |
| 7,169,105 B2 | 1/2007 | Iwasaka et al. | |
| 7,615,004 B2 * | 11/2009 | Stokes et al. | 600/104 |
| 2002/0143237 A1 | 10/2002 | Oneda et al. | |
| 2002/0156347 A1 | 10/2002 | Kim et al. | |
| 2004/0102681 A1 | 5/2004 | Gross | |
| 2005/0038335 A1 | 2/2005 | Gross et al. | |
| 2005/0059931 A1 | 3/2005 | Garrison et al. | |
| 2005/0124856 A1 | 6/2005 | Fujikura et al. | |
| 2005/0125005 A1 | 6/2005 | Fujikura | |
| 2005/0133453 A1 | 6/2005 | Woodruff et al. | |
| 2005/0137457 A1 | 6/2005 | Machida | |
| 2005/0159645 A1 | 7/2005 | Bertolero et al. | |
| 2005/0165233 A1 | 7/2005 | Hamedi et al. | |
| 2005/0165273 A1 | 7/2005 | Takano | |
| 2005/0273021 A1 | 12/2005 | Burgermeister | |
| 2006/0111610 A1 | 5/2006 | Machida | |
| 2006/0161044 A1 | 7/2006 | Oneda et al. | |
| 2006/0241345 A1 | 10/2006 | Oishi et al. | |
| 2007/0244361 A1 | 10/2007 | Ikeda et al. | |

FOREIGN PATENT DOCUMENTS

| | | |
|---|---|---|
| WO | 9953827 | 10/1999 |
| WO | 02064028 | 8/2002 |
| WO | 03080155 | 10/2003 |
| WO | 2004101059 | 11/2004 |
| WO | WO-2005074377 | 8/2005 |
| WO | WO-2007017854 | 2/2007 |

OTHER PUBLICATIONS

Double Balloon Endoscope product, including EN-450T5 enteroscope, TS-13140 overtube and BS-2 front balloon, which interface with balloon pump control BP-20 and 2200 video system, all commercially available from Fujinon Inc., of 10 High Point Drive, Wayne, New Jersey, USA.

Single Balloon Endoscope product, including SIF-Q 180 enteroscope, ST-SB1 overtube, which interface with balloon pump control OBCU and EVIS EXERA II system video system, all commercially available from Olympus Inc., o 3500 Corporate Parkway Center Valley, PA 18034-0610, USA.

An English Translation of the Prior Art issues only cited in an Office Action dated Jan. 21, 2013, which issued during the prosecution of Israel Patent Application No. 195314.

* cited by examiner

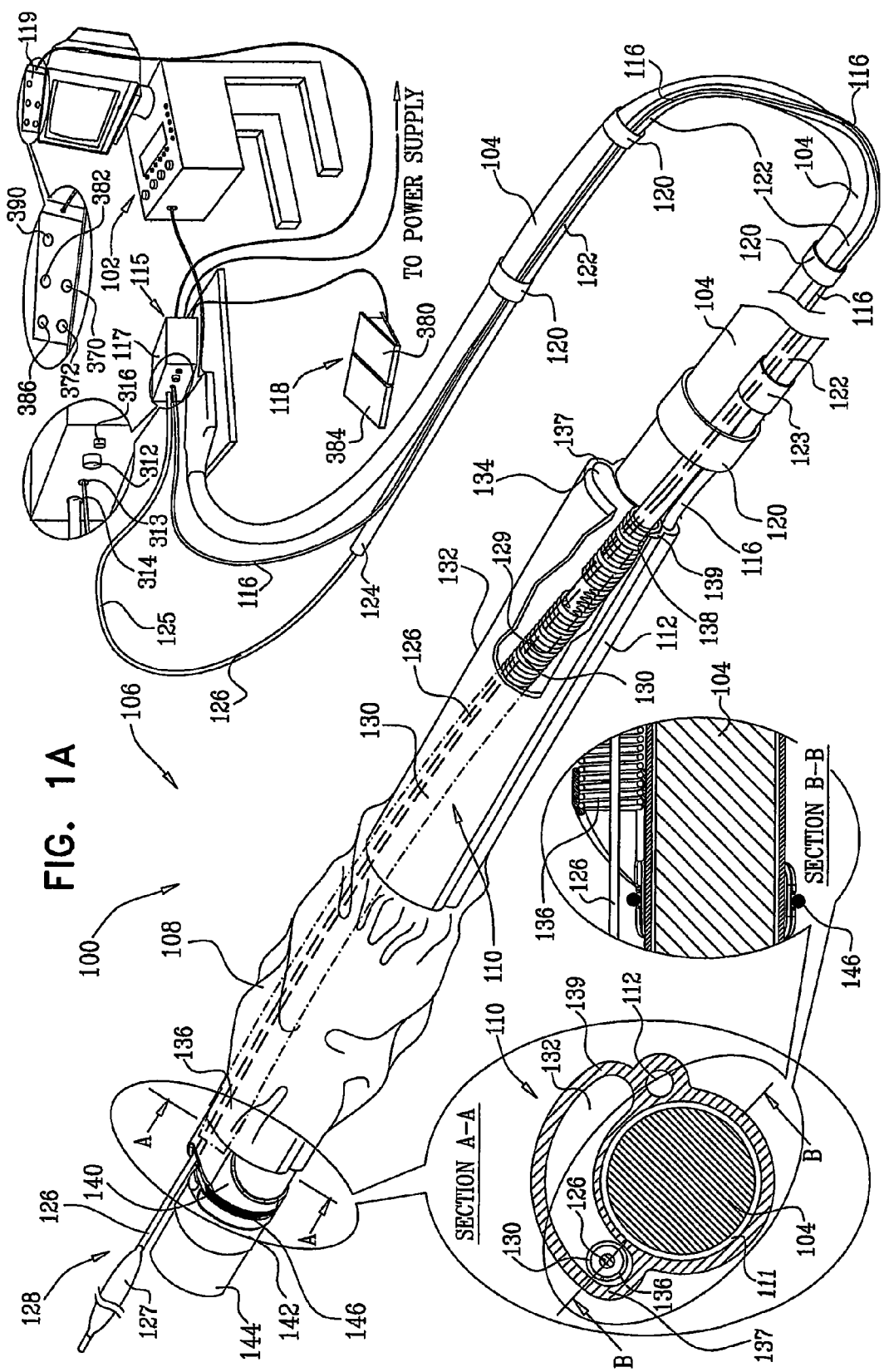

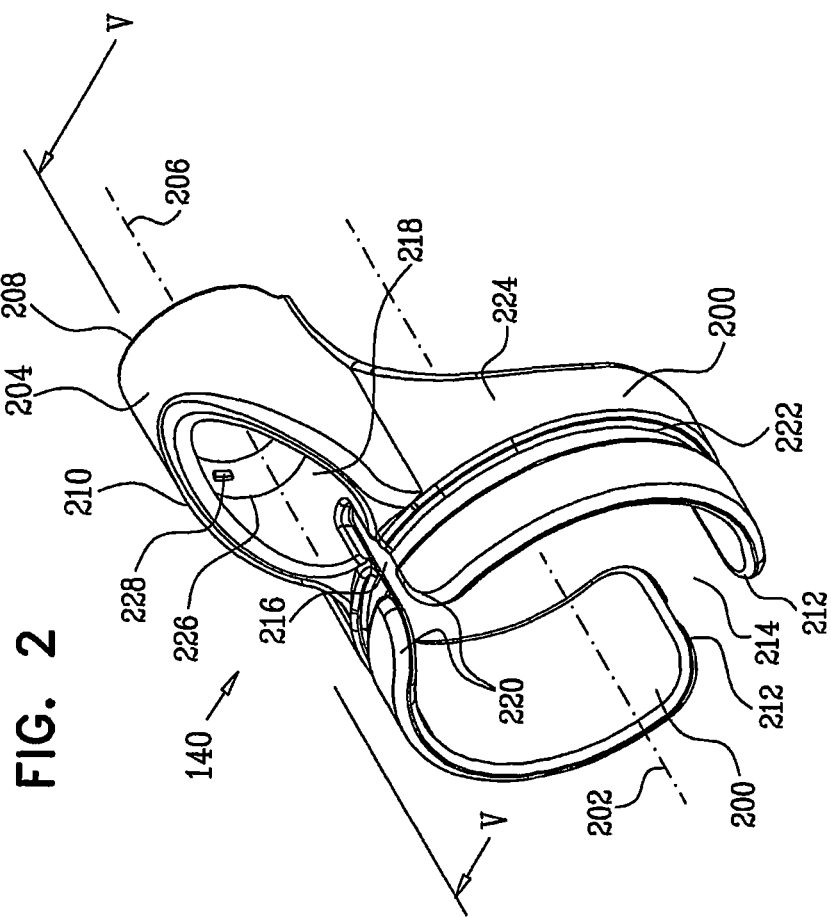

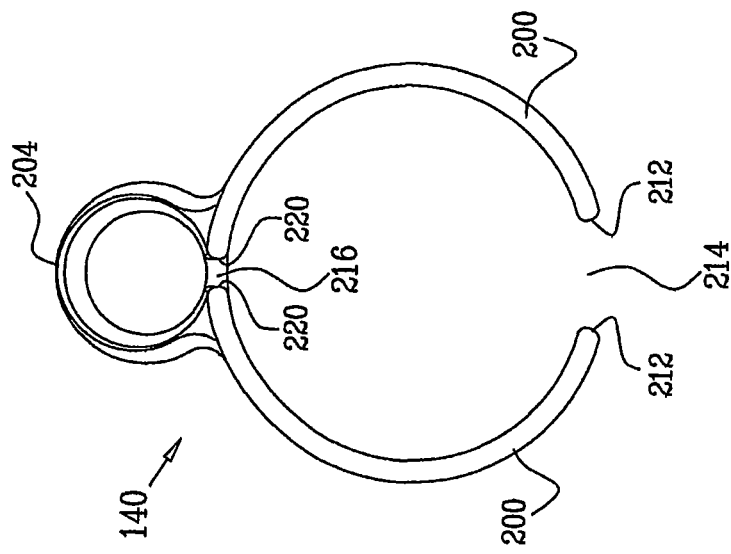
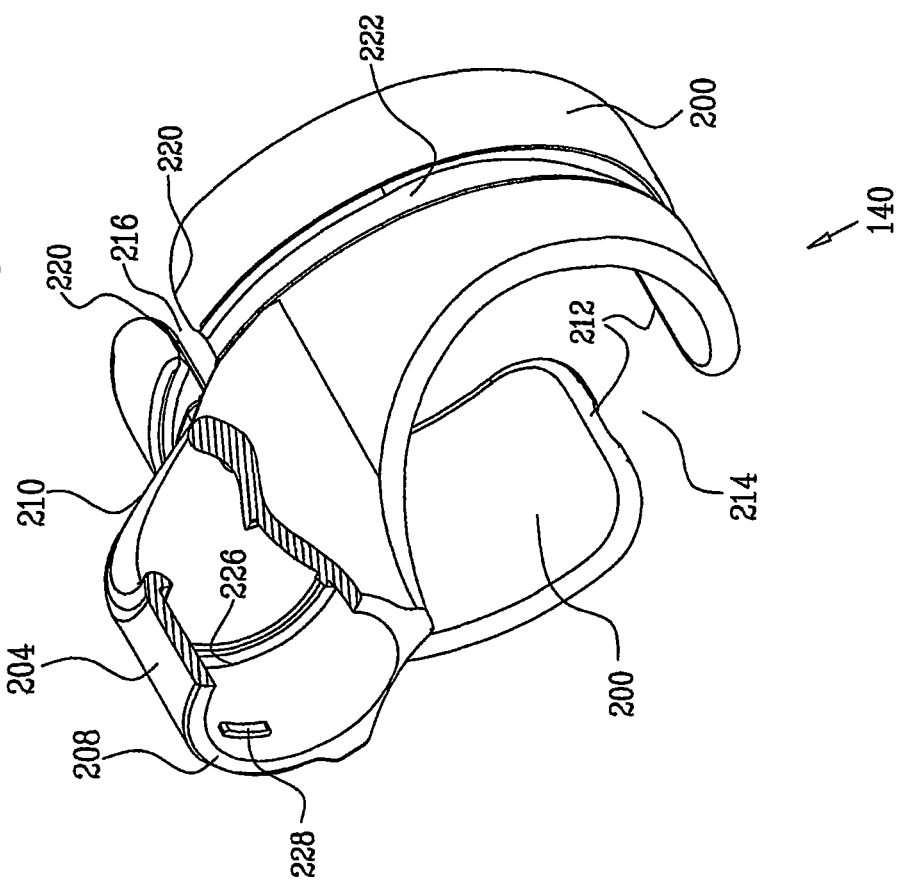

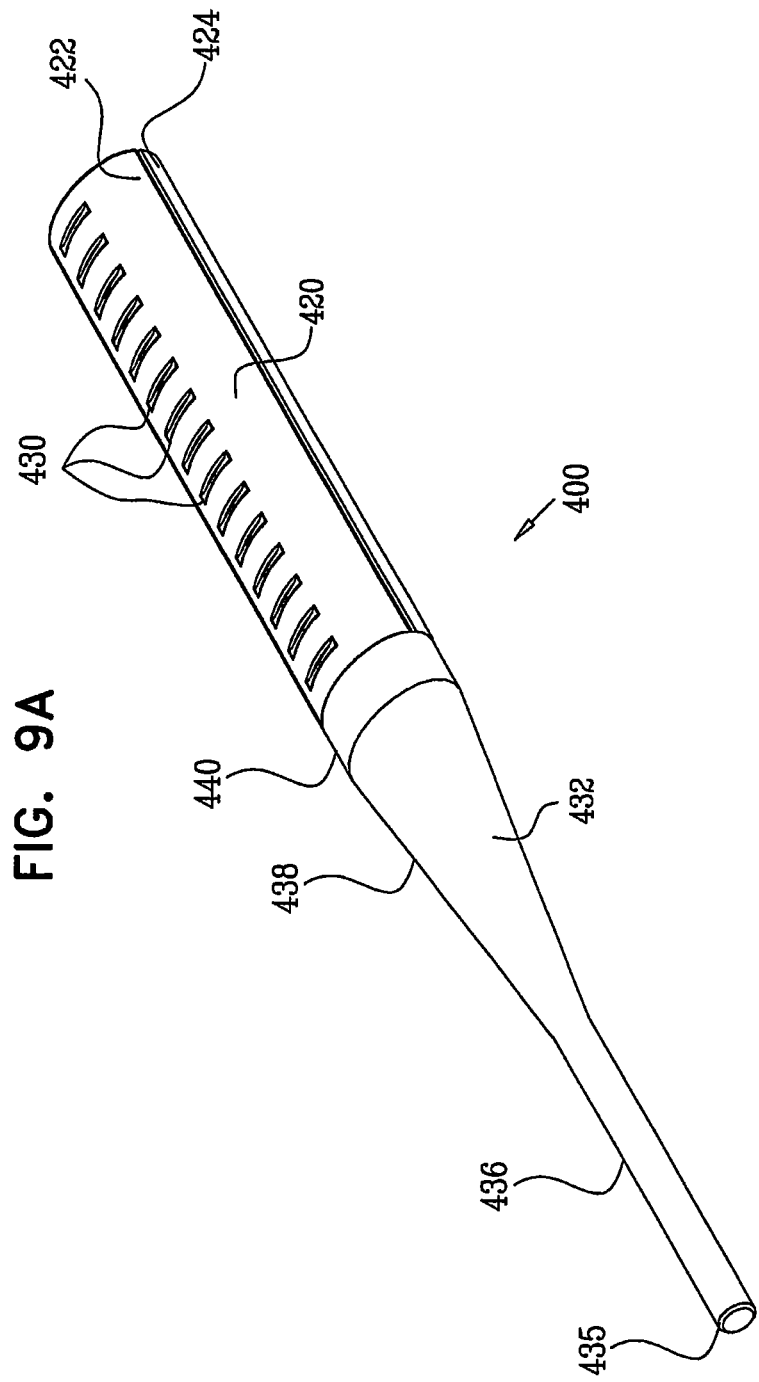

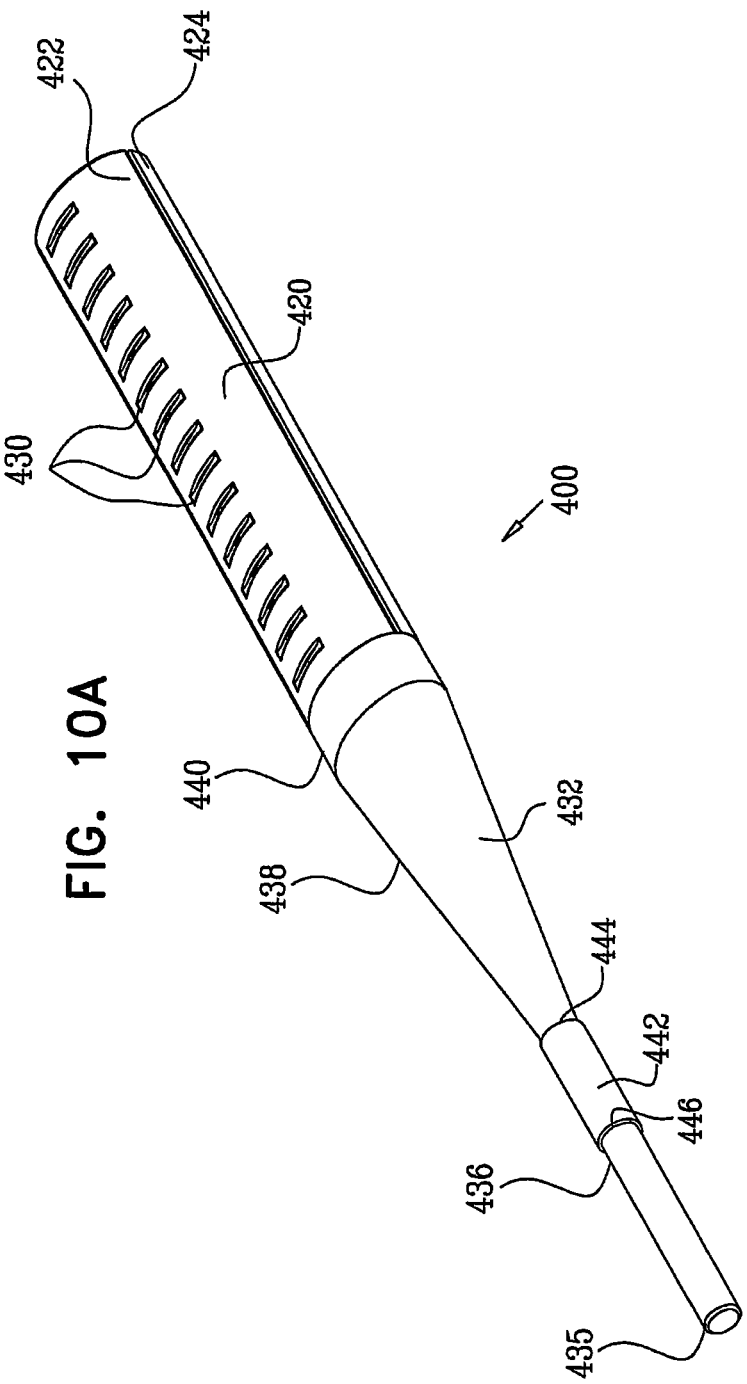

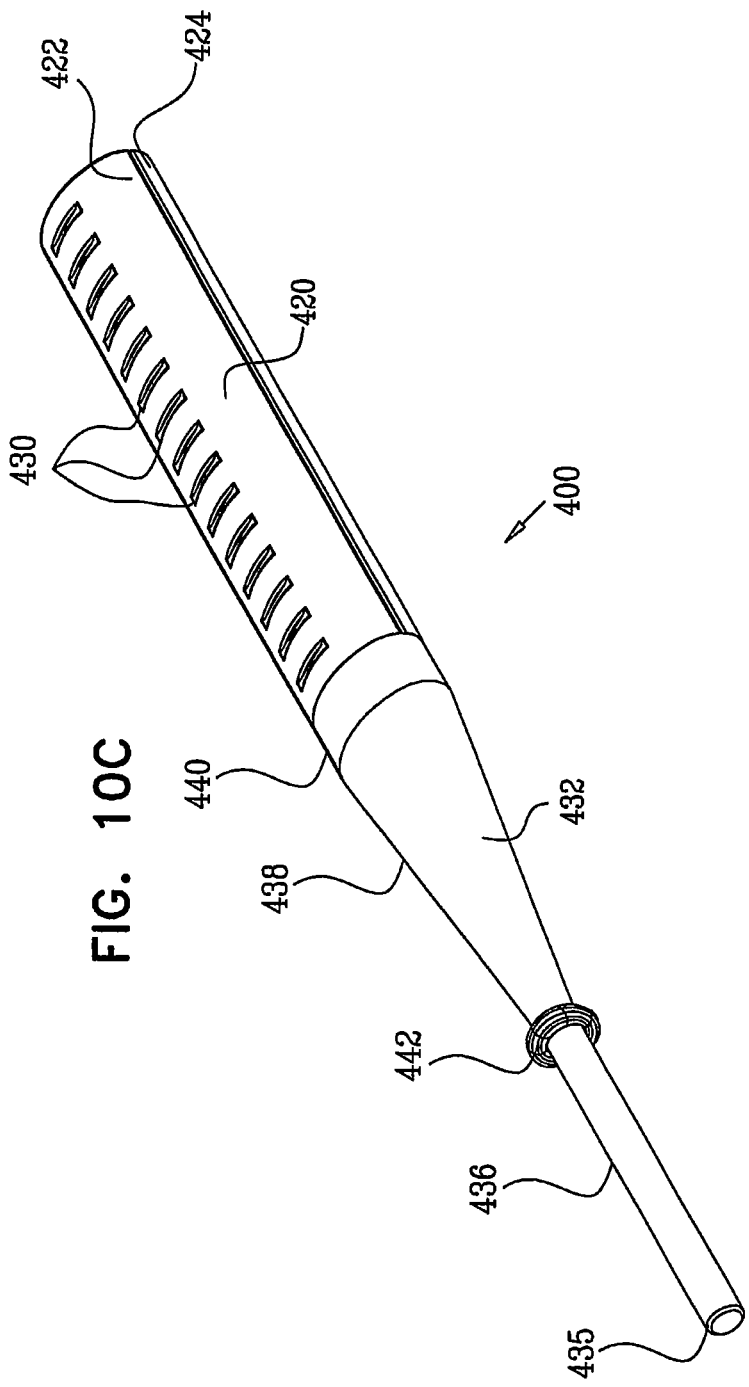

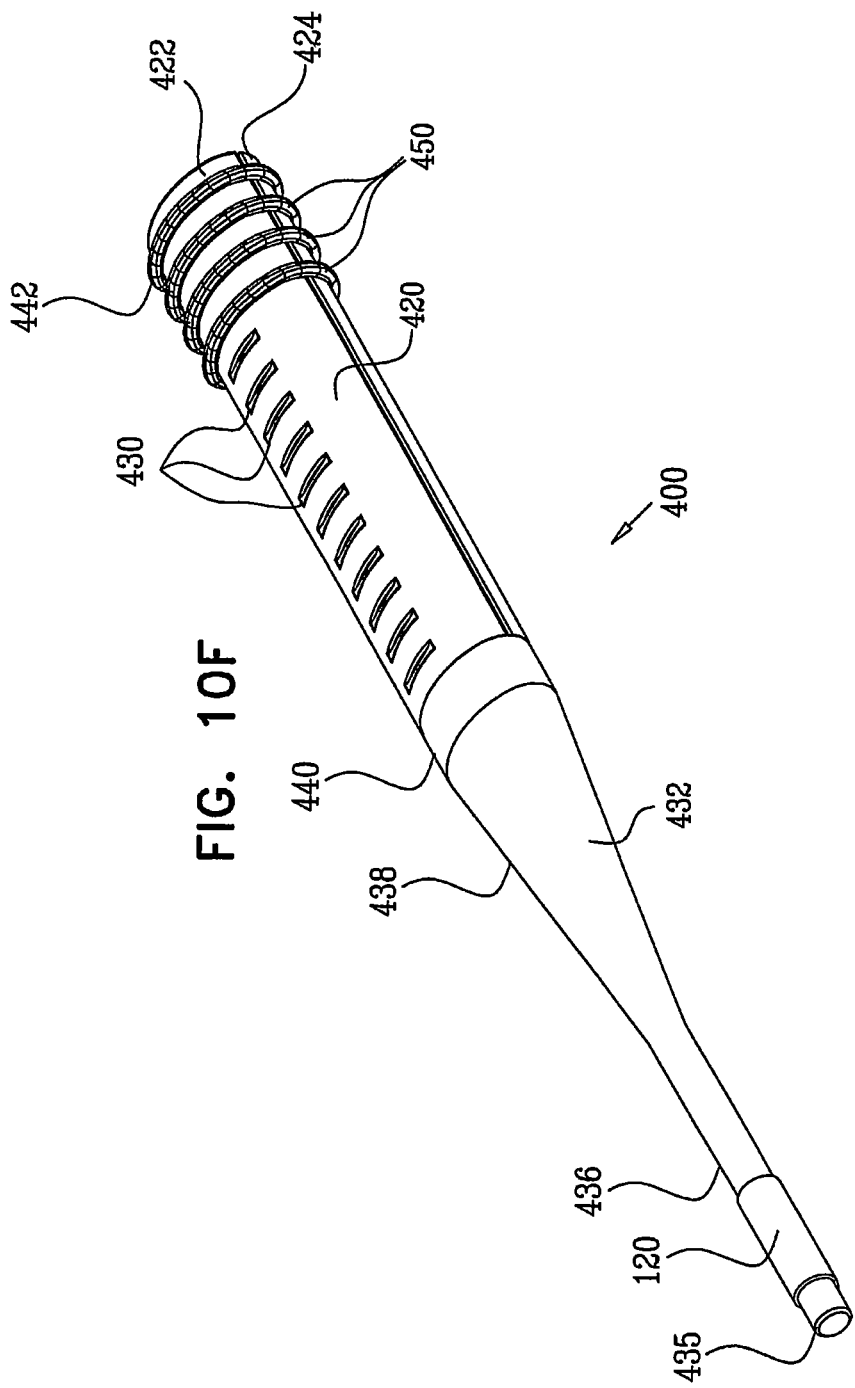

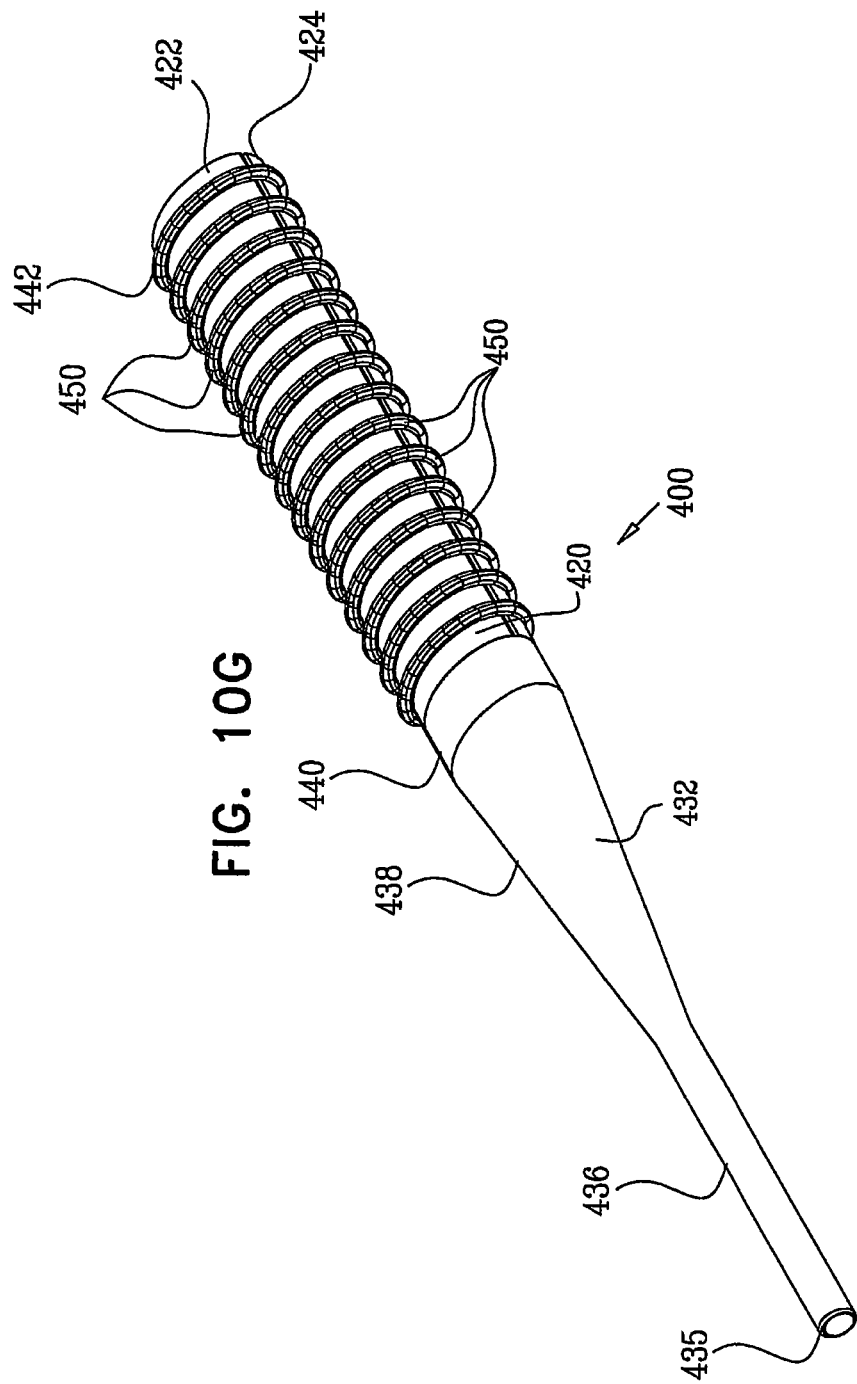

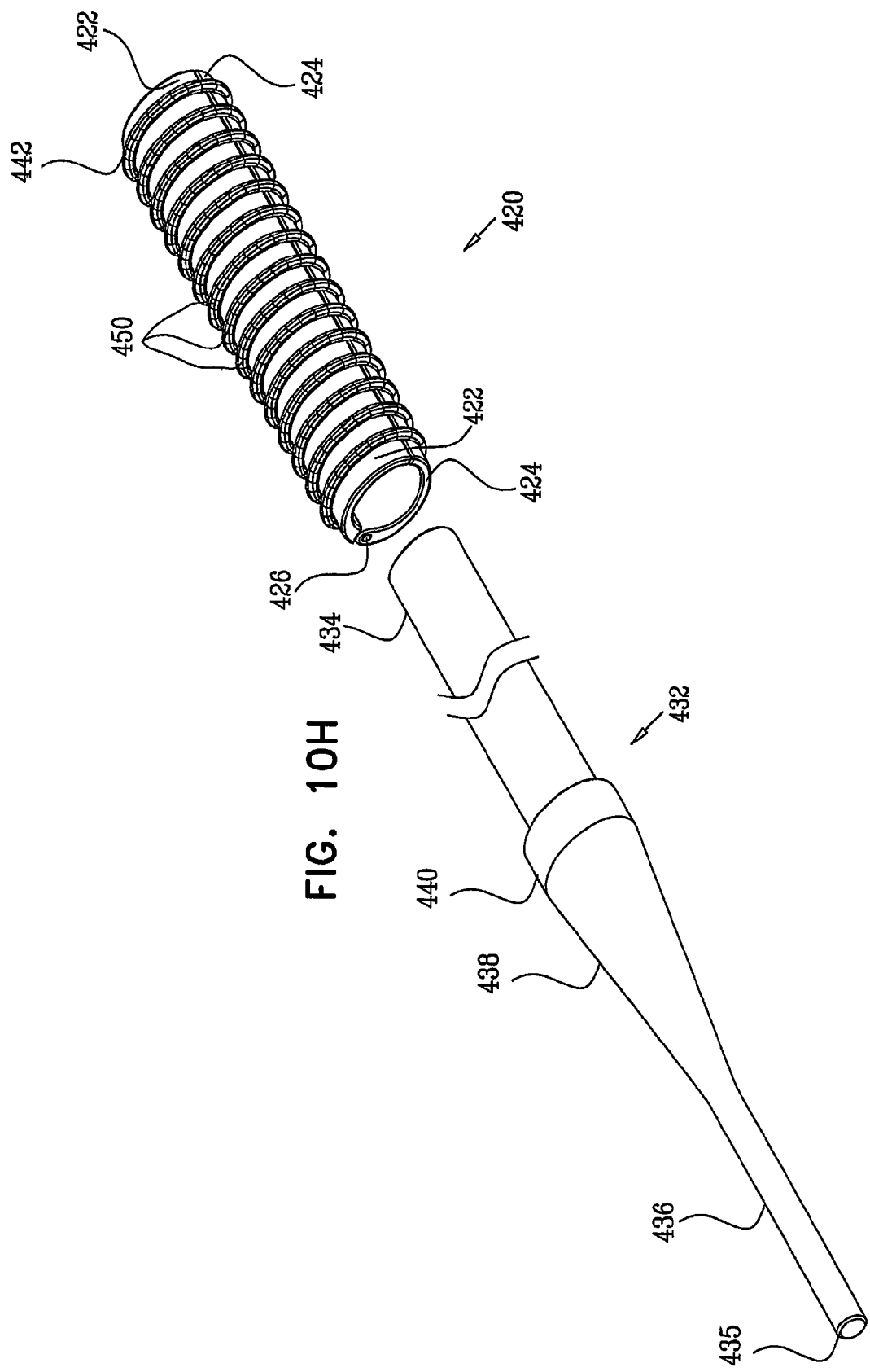

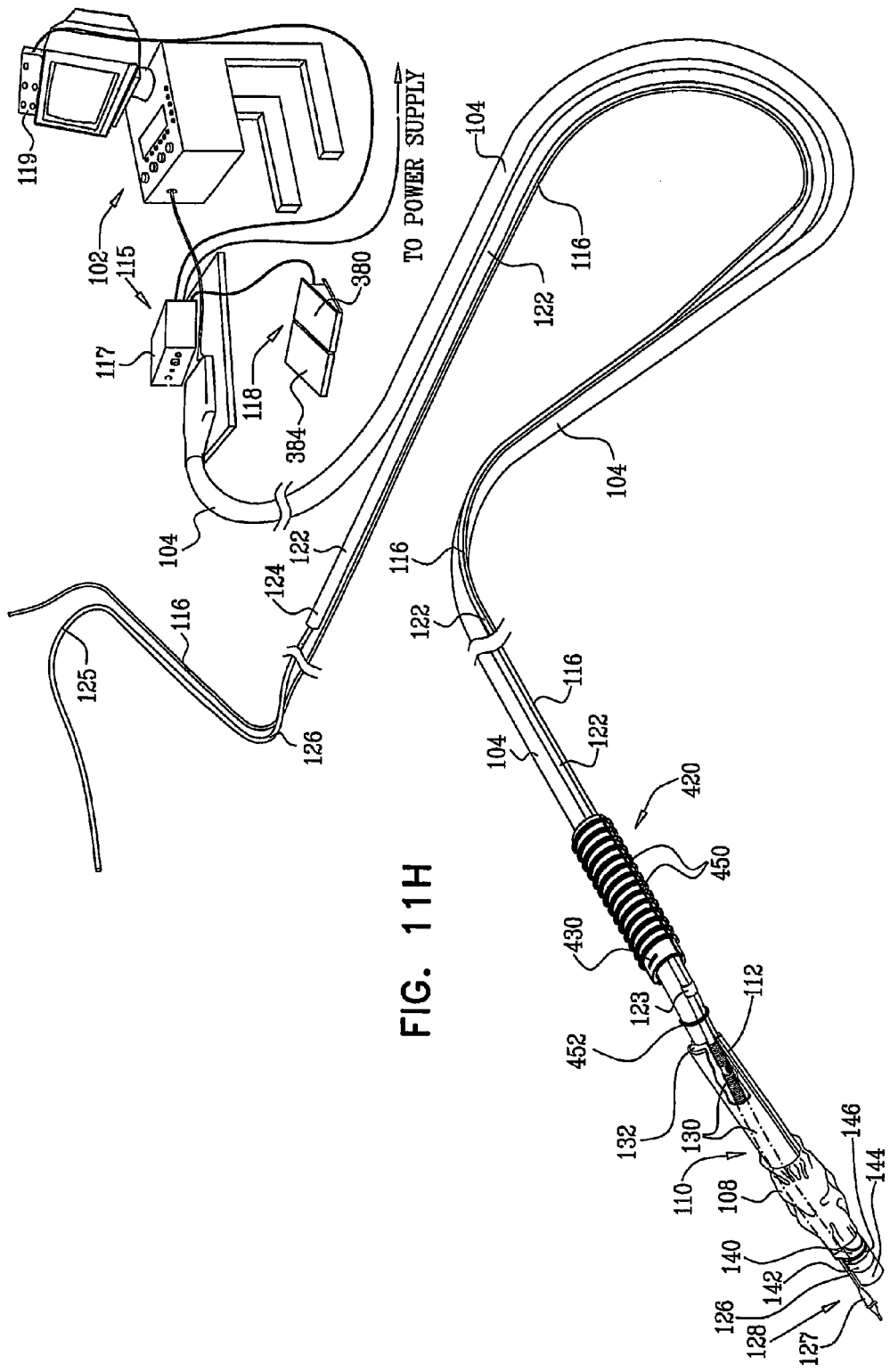

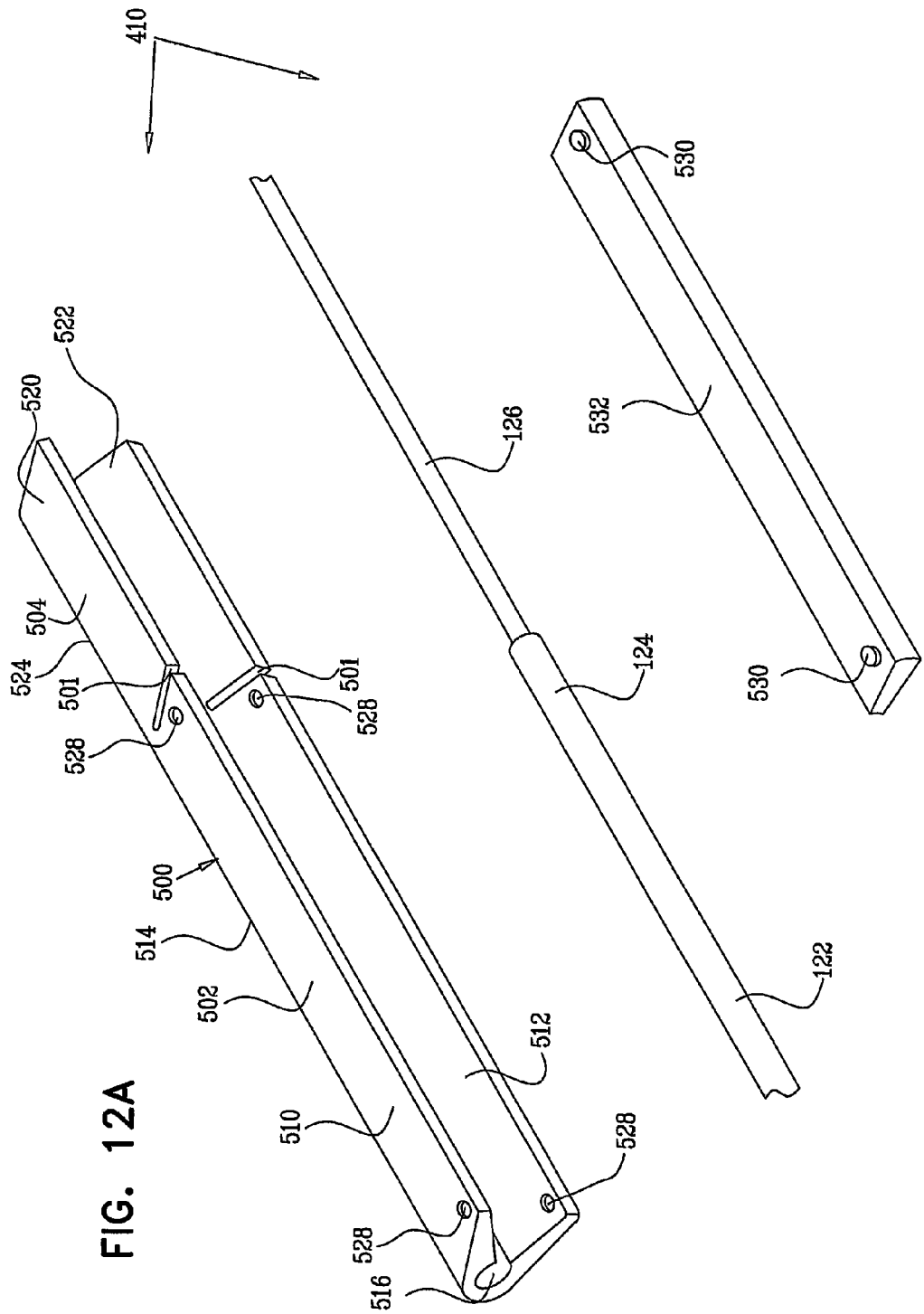

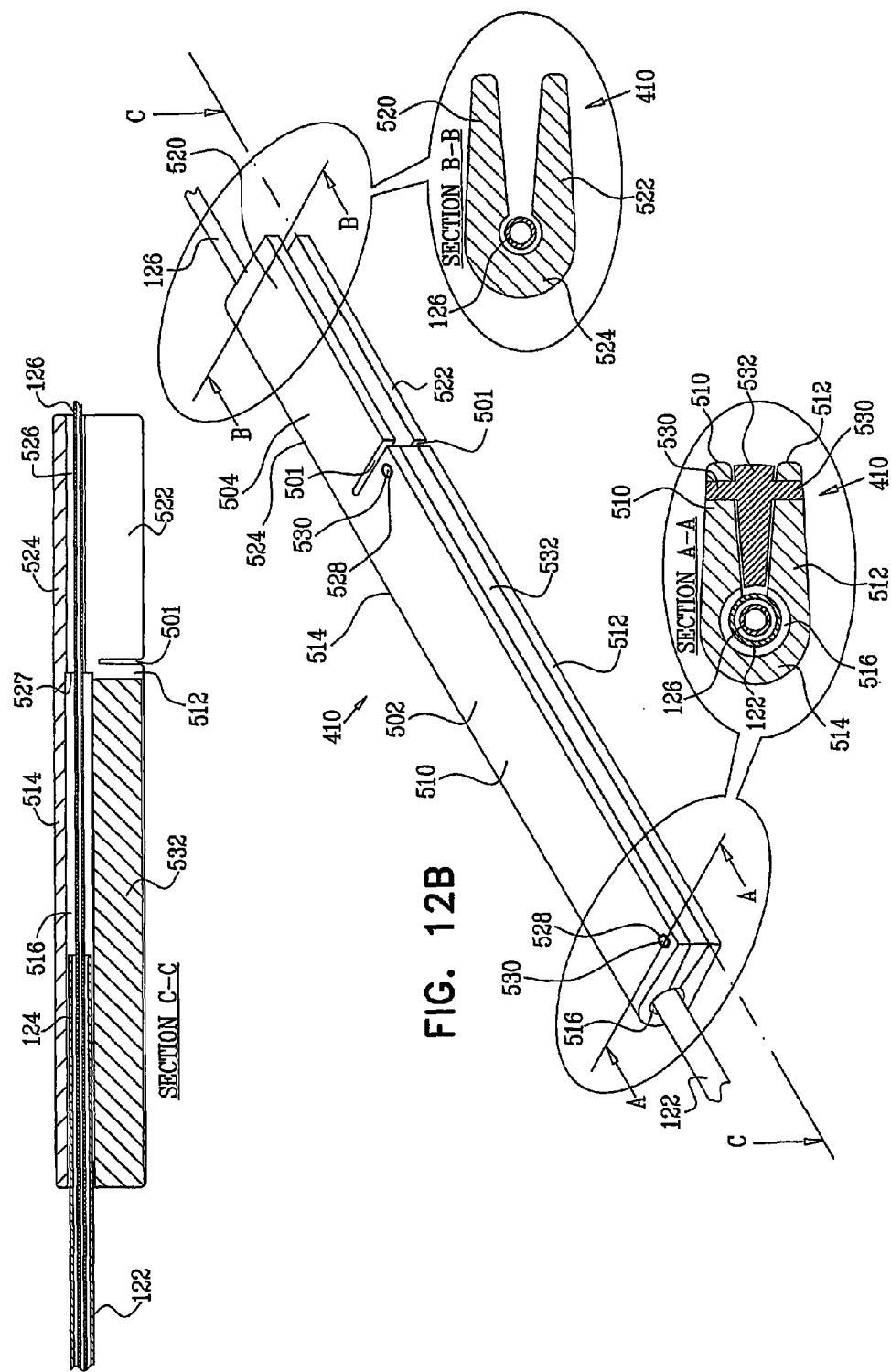

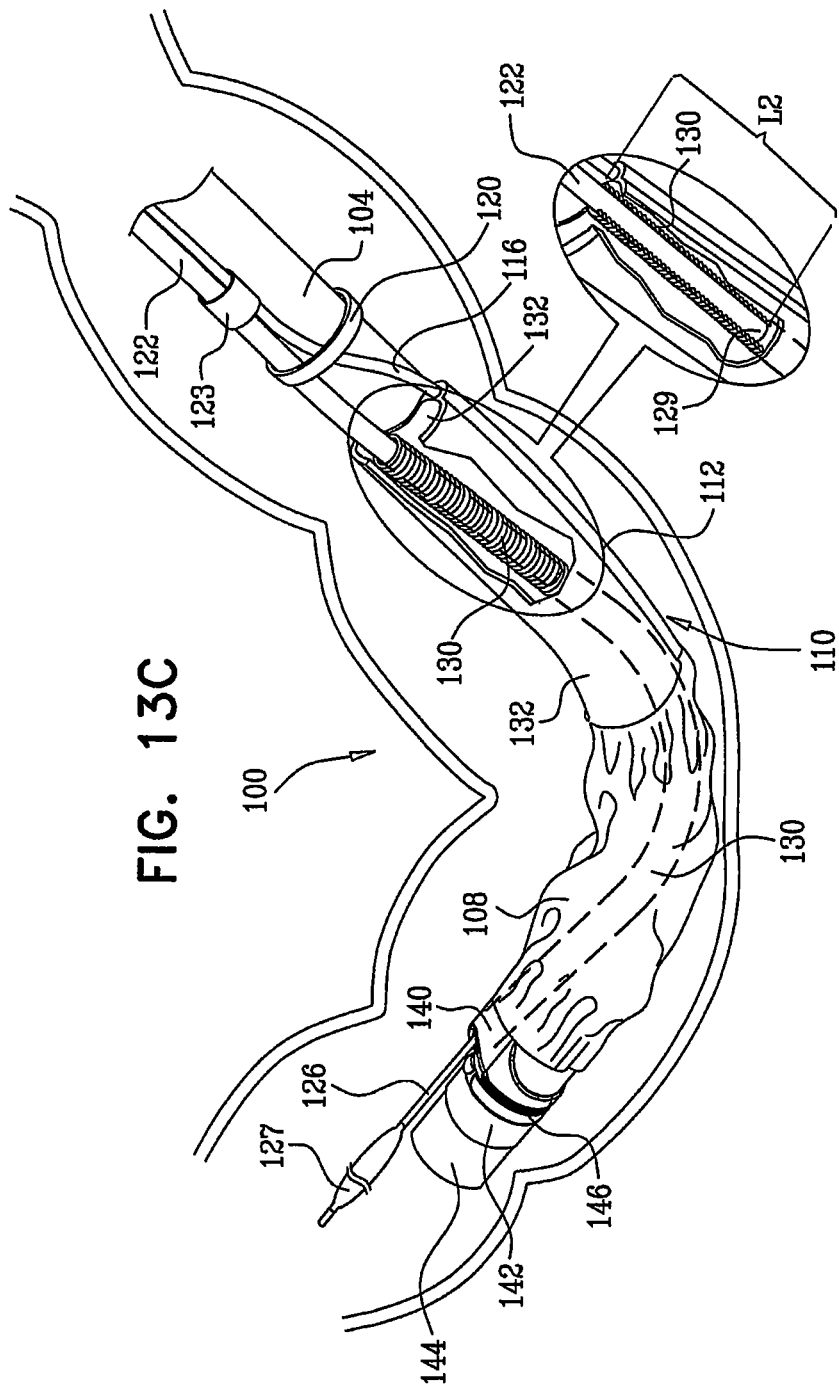

FLEXIBLE ENDOSCOPE SYSTEM AND FUNCTIONALITY

REFERENCE TO RELATED APPLICATIONS

Reference is made to U.S. Provisional Patent Application Ser. No. 60/801,057, filed May 18, 2006 and entitled "Fastening Devices and Applications Thereof," U.S. Provisional Patent Application Ser. No. 60/801,058, filed May 18, 2006 and entitled "Tubular Assembly and Applications Thereof," U.S. Provisional Patent Application Ser. No. 60/801,093, filed May 18, 2006 and entitled "Tubular Assembly," U.S. Provisional Patent Application Ser. No. 60/840,006, filed Aug. 25, 2006, and entitled "Air Supply Unit," U.S. Provisional Patent Application Ser. No. 60/873,261, filed Dec. 7, 2006 and entitled "Advancing Elements and Applications Thereof," and U.S. Provisional Patent Application Ser. No. 60/873,262, filed Dec. 7, 2006 and entitled "Band Mounting Assembly," the disclosures of which are hereby incorporated by reference and priorities of which are hereby claimed pursuant to 37 CFR 1.78(a)(4) and (5)(i).

Reference is made to applicant's copending PCT Application No. PCT/IL2005/000152, filed Feb. 7, 2005, and PCT Application No. PCT/IL2005/000849, filed Aug. 8, 2005, the disclosures of which are hereby incorporated by reference.

FIELD OF THE INVENTION

The present invention relates to endoscope systems generally.

BACKGROUND OF THE INVENTION

The following patent publications are believed to represent the current state of the art:
U.S. Pat. Nos. 7,169,105 and 7,056,284.

SUMMARY OF THE INVENTION

The present invention seeks to provide improved endoscope assemblies.

There is thus provided in accordance with a preferred embodiment of the present invention an enhanced flexibility auxiliary endoscope assembly for use with an endoscope, the assembly including at least one flexible elongate element and a flexible sleeve having a first lumen for accommodating a distal portion of an endoscope capable of assuming at least a first curvature and a second lumen for accommodating the at least one flexible elongate element, the second lumen being configured to allow the at least one flexible elongate element to assume the at least first curvature as well as at least a second curvature about the first curvature, thereby to enhance flexibility of the auxiliary endoscope assembly.

There is also provided in accordance with another preferred embodiment of the present invention an enhanced flexibility auxiliary endoscope assembly for use with an endoscope, the assembly including a flexible elongate element having an outer cross section having a diameter and a flexible elongate sleeve having a first lumen for accommodating a distal portion of an endoscope capable of assuming at least a first curvature and a second lumen for accommodating the flexible elongate element, the second lumen being configured to define, at least along a portion of the elongate extent thereof, an elongate element transverse displacement accommodating volume having a transverse extent at least twice as long as the diameter of the outer cross section of the flexible elongate element.

There is further provided in accordance with yet another preferred embodiment of the present invention an enhanced flexibility endoscope system including an endoscope, a flexible elongate element and a flexible sleeve having a first lumen for accommodating a distal portion of the endoscope capable of assuming at least a first curvature and a second lumen for accommodating the flexible elongate element, the second lumen being configured to allow the flexible elongate element to assume the at least first curvature as well as at least a second curvature about the first curvature, thereby to enhance flexibility of the endoscope system.

There is yet further provided in accordance with still another preferred embodiment of the present invention an enhanced flexibility endoscope system including an endoscope, a flexible elongate element having an outer cross section having a diameter and a flexible elongate sleeve having a first lumen for accommodating a distal portion of the endoscope capable of assuming at least a first curvature and a second lumen for accommodating the flexible elongate element, the second lumen being configured to define, at least along a portion of the elongate extent thereof, an elongate element transverse displacement accommodating volume having a transverse extent at least twice as long as the diameter of the outer cross section of the flexible elongate element.

Preferably, the at least one flexible elongate element is angularly misaligned with respect to the first lumen. Additionally or alternatively, at least part of the second lumen has a generally saddle shaped cross section. Preferably, the saddle shaped cross section is adapted to enable the at least one flexible elongate element to be slidably displaced laterally in accordance with the first curvature.

Preferably, the enhanced flexibility auxiliary endoscope assembly also includes a collar assembly operative to secure together at least the endoscope, the at least one flexible elongate element and the flexible sleeve.

There is also provided in accordance with another preferred embodiment of the present invention an enhanced flexibility auxiliary endoscope assembly for use with an endoscope, the assembly including an elongate element and an elongate channel each arranged for mounting at a different location on a distal portion of the endoscope, the elongate channel being arranged to receive the elongate element to a variable elongate extent, at least one of the elongate element and the elongate channel being flexible and the variable elongate extent varying as a function of a degree of bending of the endoscope.

There is further provided in accordance with still another preferred embodiment of the present invention an enhanced flexibility endoscope system including an endoscope and an elongate element and an elongate channel each arranged for mounting at a different location on a distal portion of the endoscope, the elongate channel being arranged to receive the elongate element to a variable elongate extent, at least one of the elongate element and the elongate channel being flexible and the variable elongate extent varying as a function of a degree of bending of the endoscope.

Preferably, the enhanced flexibility auxiliary endoscope assembly also includes a flexible elongate element having an outer cross section having a diameter and a flexible sleeve having a first lumen for accommodating a distal portion of the endoscope and a second lumen for accommodating the flexible elongate element, the first lumen being configured for accommodating the distal portion of the endoscope which is capable of assuming at least a first curvature and the second lumen being configured to define, at least along a portion of the elongate extent thereof, an elongate element transverse displacement accommodating volume having a transverse extent at least twice as long as the diameter of the outer cross section of the flexible elongate element.

Preferably, at least one of the elongate channel and elongate element is angularly misaligned with respect to the endoscope. In accordance with another preferred embodiment the enhanced flexibility auxiliary endoscope assembly also includes a collar assembly operative to secure together at least the endoscope and the elongate channel.

Preferably, the enhanced flexibility auxiliary endoscope assembly also includes an inflatable balloon mounted onto the flexible sleeve. Additionally or alternatively, the at least one flexible elongate element includes a channel. Additionally, the at least one flexible elongate element also includes an endoscope tool which extends through the channel and includes an inflatable endoscope tool balloon.

In accordance with another preferred embodiment the channel is defined at least in part by a coil spring. Additionally or alternatively, the channel includes at least first and second mutually telescoping channel elements.

Additionally, the collar assembly includes a collar element and a retaining band engaging the collar element, the collar assembly being adapted for securing endoscopes of varying cross-sectional dimensions.

Preferably, the enhanced flexibility auxiliary endoscope assembly also includes an endoscope tool manipulator assembly for advancing and retracting the endoscope tool.

In accordance with another preferred embodiment the at least one flexible elongate element includes an elongate element and an elongate channel each arranged for mounting at a different location on a distal portion of the endoscope, the elongate channel being arranged to receive the elongate element to a variable elongate extent, at least one of the elongate element and the elongate channel being flexible and the variable elongate extent varying as a function of a degree of bending of the endoscope. Additionally or alternatively, the flexible elongate element has an outer cross section having a diameter and the first lumen is configured for accommodating the distal portion of the endoscope which is capable of assuming at least a first curvature and the second lumen is configured to define, at least along a portion of the elongate extent thereof, an elongate element transverse displacement accommodating volume having a transverse extent at least twice as long as the diameter of the outer cross section of the flexible elongate element.

Preferably, the inflatable balloon can be inflated to a diameter 3-10 times larger than its diameter when not inflated. Additionally or alternatively, the inner diameter of the channel is in the range of 3-6 mm.

In accordance with another preferred embodiment the inflatable endoscope tool balloon, when in a fully deflated state, is adaptive to be at least partially inserted within the channel. Additionally or alternatively, the inflatable endoscope tool balloon is adaptive to be inflated to a diameter of at least 35 mm.

Preferably, the enhanced flexibility auxiliary endoscope assembly also includes at least one inflation control subassembly operative to facilitate at least one of inflation and deflation at least one of the inflatable balloon and the inflatable endoscope tool balloon. Additionally, the at least one inflation control subassembly includes initialization functionality operative to ensure that prior to operation at least one of the inflatable balloon and the inflatable endoscope tool balloon is in a fully deflated state.

There is yet further provided in accordance with still another preferred embodiment of the present invention an enhanced flexibility auxiliary endoscope assembly for use with an endoscope, the assembly including a coil spring and a flexible sleeve having a first lumen for accommodating a distal portion of an endoscope capable of assuming at least a first curvature and a second lumen for accommodating the coil spring.

There is also provided in accordance with another preferred embodiment of the present invention an enhanced flexibility endoscope system including an endoscope, a coil spring and a flexible sleeve having a first lumen for accommodating a distal portion of the endoscope capable of assuming at least a first curvature and a second lumen for accommodating the coil spring.

There is even further provided in accordance with yet another preferred embodiment of the present invention an endoscope system including an endoscope, an auxiliary endoscope assembly and a plurality of stretchable resilient endless mounting bands engaging the endoscope and auxiliary endoscope assembly at spaced locations along the length thereof.

There is also provided in accordance with another preferred embodiment of the present invention an endoscope tool manipulator including a tube clamping element operative to clamp a first tube and a tube guiding element operative to guide a second tube, the endoscope tool manipulator assembly operative to advance and retract the first tube relative to the second tube.

Preferably, the first tube is located within the second tube. Additionally or alternatively, the tube guiding element also includes a locking element. Additionally or alternatively, the endoscope tool manipulator assembly also includes a shoulder defining an extent of movement of the second tube relative to the first tube.

BRIEF DESCRIPTION OF THE DRAWINGS

The present invention will be better understood and appreciated from the following detailed description, taken in conjunction with the drawings in which:

FIGS. 1A and 1B are, respectively, pictorial and exploded view simplified illustrations of a flexible endoscope system constructed and operative in accordance with a preferred embodiment of the present invention;

FIG. 2 is a simplified pictorial illustration of a collar element forming part of the flexible endoscope system of FIGS. 1A and 1B;

FIG. 3 is a simplified, partially pictorial, partially sectional, illustration of the collar element of FIG. 2;

FIG. 4 is a simplified end view illustration of the collar element of FIGS. 2 and 3;

FIGS. 9A and 9B are respective simplified assembled and exploded view illustrations of a flexible band mounting assembly used in preparation of the flexible endoscope system of FIGS. 1A and 1B for use;

FIGS. 10A, 10B, 10C, 10D, 10E, 10F, 10G and 10H are simplified illustrations of loading flexible bands onto a flexible band holder, forming part of the flexible band mounting assembly of FIGS. 9A and 9B;

FIGS. 11A, 11B, 11C, 11D, 11E, 11F, 11G, 11H, 11I, 11J, 11K and 11L are simplified illustrations of unloading flexible bands from the flexible band holder, forming part of the flexible band mounting assembly of FIGS. 9A and 9B, and placement of the flexible bands onto the flexible endoscope assembly at appropriate locations therealong;

FIGS. 12A and 12B are simplified assembled and exploded view illustrations of an endoscope tool driving assembly useful in operation of the flexible endoscope system of FIGS. 1A and 1B; and FIGS. 13A, 13B, 13C, 13D, 13E, 13F and 13G are simplified illustrations of operation of the flexible endoscope system of FIGS. 1A and 1B.

DETAILED DESCRIPTION OF EMBODIMENTS

The terms "endoscope" and "endoscopy" are used throughout in a manner somewhat broader than their customary meaning and refer to apparatus and methods which operate within body cavities, passageways and the like, such as, for example, the small intestine, the large intestine, arteries and veins. Although these terms normally refer to visual inspection, as used herein they are not limited to applications which employ visual inspection and refer as well to apparatus, systems and methods which need not necessarily involve visual inspection.

The term "distal" refers to the remote end of an endoscope, accessory or tool furthest from the operator.

The term "proximal" refers to the end portion of an endoscope, accessory or tool closest to the operator, typically outside an organ or body portion of interest.

Figure 1B:
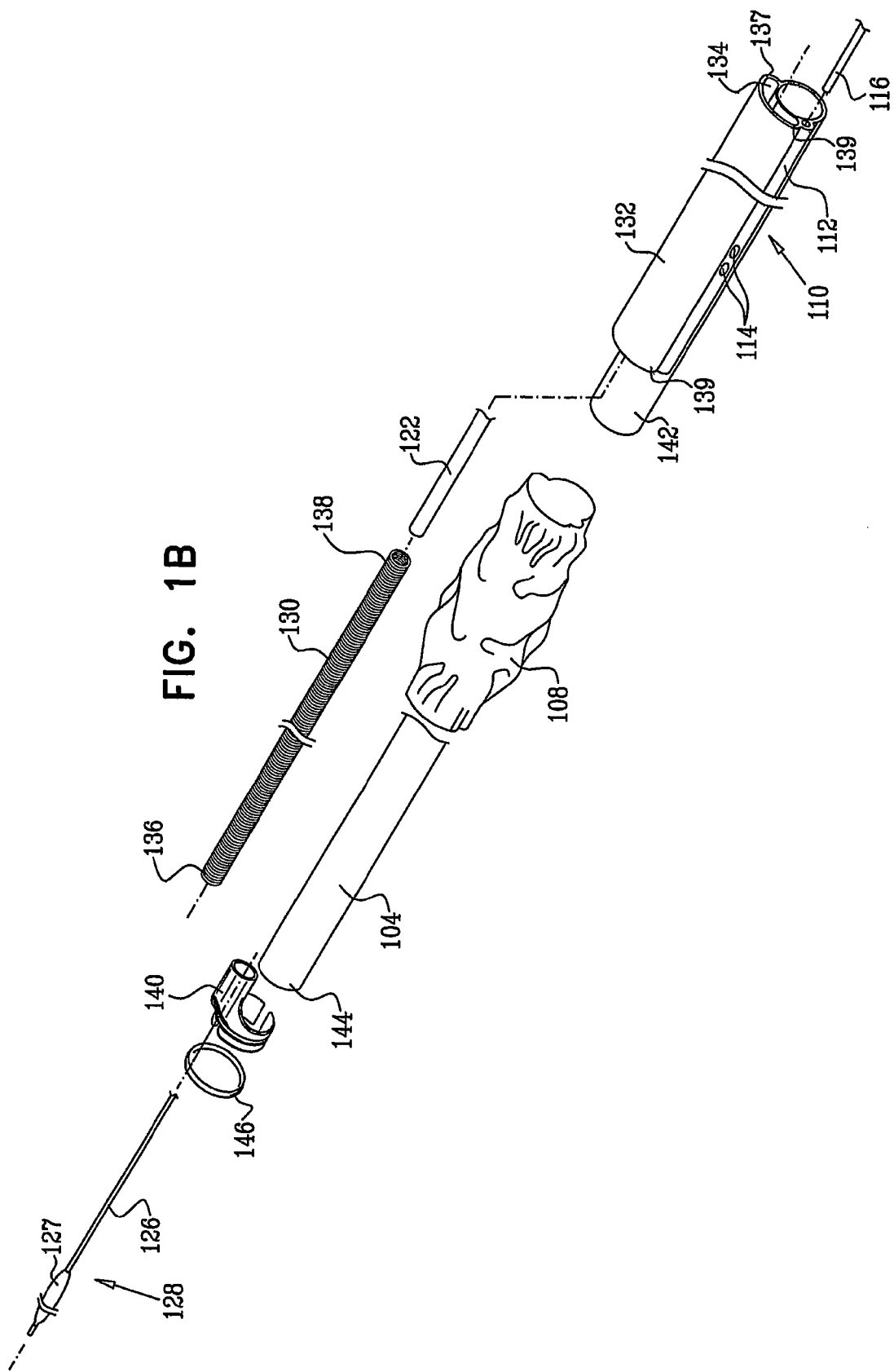
Figure 5:
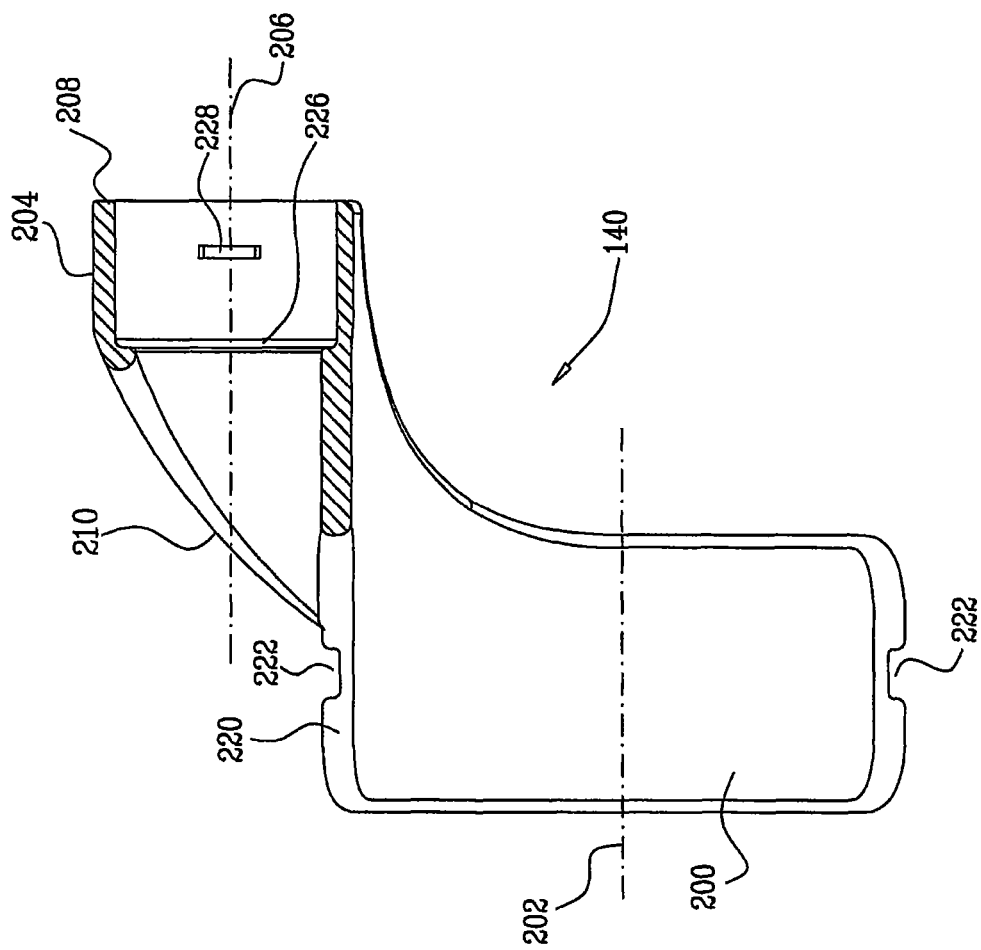
FIG. 5 is a simplified sectional illustration of the collar element of FIGS. 2-4 taken along lines V-V in FIG. 2.

Reference is now made to FIGS. 1A & 1B, which illustrate an endoscopy system 100 constructed and operative in accordance with a preferred embodiment of the present invention. The endoscopy system 100 preferably includes a console 102, such as a console including a EPK-1000 video processor and a SONY LMD-2140MD medical grade flat panel LCD monitor, all commercially available from Pentx Europe GmbH, 104 Julius-Vosseler St., 22527 Hamburg, Germany. The system 100 preferably includes a conventional flexible endoscope 104, such as a VSB-3430K video enteroscope or a EC-3470LK video colonoscope which are commercially available from Pentx Europe GmbH, 104 Julius-Vosseler St. 22527 Hamburg, Germany.

In accordance with a preferred embodiment of the invention, an auxiliary endoscopy assembly 106 comprising a peripheral balloon 108 may be mounted onto endoscope 104 as shown, by means of a tubular sleeve 110 having a central lumen 111 which is placed over part of the distal portion of endoscope 104, and is associated with peripheral balloon 108. Many of the features of auxiliary endoscopy assembly 106 are described in one or both of applicant/assignee's PCT patent application PCT/IL2005/000152 and PCT patent application PCT/IL2005/000849, which are hereby incorporated by reference.

It is appreciated that the tubular sleeve 110 may be constructed of a flexible and stretchable material, such as flexible and stretchable silicon, latex or rubber, thereby enabling it to conform with bending of endoscope 104. It is further appreciated that tubular sleeve 110 preferably has an untensioned inner circumference slightly larger than the cross-sectional circumference of endoscope 104, thereby allowing it to be pulled and slid over the endoscope 104.

As illustrated in FIGS. 1A & 1B, peripheral balloon 108 at least partially overlays tubular sleeve 110 at a location adjacent a distal end of tubular sleeve 110, and is fixed thereon at both edges by any suitable conventional means, such as an adhesive, in order to define a sealed volume therebetween. Preferably inflation and deflation of peripheral balloon 108 is provided via a lumen 112, which preferably is defined by tubular sleeve 110 and communicates with the interior of peripheral balloon 108 via at least one aperture 114. Lumen 112 preferably communicates with an inflation control unit 115 via a tube 116. Inflation control assembly 115 preferably comprises a control unit 117 having associated therewith dual foot pedals 118 and an operational status indicator panel 119.

Tube 116 may be attached to endoscope 104 at multiple locations along its length by any suitable conventional means such as medical adhesive tape or flexible bands 120.

It is appreciated that in accordance with a preferred embodiment of the present invention peripheral balloon 108 is generally inflatable, and can be inflated to a diameter about 3-10 times larger than its diameter when not inflated. In accordance with a preferred embodiment of the present invention, useful for small intestine endoscopy, the diameter of peripheral balloon 108 when fully inflated is in the range of 35-45 mm. Preferably, inflation of the peripheral balloon 108 to a diameter less than 45 mm may be achieved using relatively low pressure, such as in the range of 30-70 millibars.

In another specific embodiment, useful for large intestine endoscopy, the diameter of the peripheral balloon, when fully inflated, is in the range of 4-6 centimeters. In a further embodiment, also useful for large intestine endoscopy, the diameter of the peripheral balloon, when fully inflated, is six centimeters. Preferably, inflation of the peripheral balloon 108 to a diameter less than six centimeters may be achieved using relatively low pressure, such as in the range of 30-70 millibars.

It is appreciated that in accordance with a preferred embodiment of the present invention, useful for in vivo inspection of a generally tubular body portion having a variable cross-sectional diameter, the expansion diameter range of peripheral balloon 108 is larger than the maximum cross-sectional diameter of the generally tubular body portion, thereby enabling engagement of expanded peripheral balloon 108 with the interior surface of the generally tubular body portion, and anchoring of the endoscope 104 thereto. Preferably, peripheral balloon 108 is a relatively soft, highly compliant balloon, operative to at least partially conform to the shape of the interior surface of the generally tubular body portion when in engagement therewith.

It is appreciated that peripheral balloon 108 may be formed of suitable well-known stretchable materials such as latex, flexible silicon, or highly flexible nylon. Alternatively, peripheral balloon 108 may be formed of polyurethane, which is less stretchable and conforming than latex, flexible silicon or highly flexible nylon. Preferably, the diameter of peripheral balloon 108 is sufficient to ensure tight anchoring at any part of the generally tubular body portion. Alternatively, peripheral balloon 108 may be obviated.

In a preferred embodiment of the present invention, auxiliary assembly 106 may comprise at least one external tube 122. External tube 122 may be attached to the endoscope 104 at multiple locations along its length by any suitable conventional means such as medical adhesive tape or flexible bands 120. External tube 122 is preferably attached to tube 116 by a band 123. A proximal end 124 of tube 122 is typically open to enable a proximal end 125 of an inflation tube 126 coupled to a balloon 127 of an endoscope tool 128 to extend therefrom outside of a patient's body, thereby enabling insertion, removal and manipulation of tool 128 by an operator. Additionally any other suitable endoscope tool may be inserted, removed or manipulated through tube 122. Proximal end 125 of inflation tube 126 of endoscope tool 128 is also coupled to the inflation control assembly 115.

Many of the features of endoscope tool 128 are described in one or both of applicant/assignee's PCT patent application PCT/IL2005/000152 and PCT patent application PCT/IL2005/000849, which are hereby incorporated by reference. In accordance with a preferred embodiment of the present invention, useful for small intestine endoscopy, the diameter of balloon 127 when fully inflated is in the range of 35-45 mm. Preferably, inflation of the peripheral balloon 127 to a diameter less than 45 mm may be achieved using relatively low pressure, such as in the range of 30-70 millibars.

A distal end 129 of external tube 122 preferably extends slidably and telescopically through part of the length of a coil spring 130 which movably and slidably resides within a lumen 132, which preferably forms part of tubular sleeve 110. Preferably distal end 129 is beveled for ease of passage into and through coil spring 130. It is a particular feature of the present invention that spring 130 defines a generally non-collapsible and highly flexible channel for endoscope tool 128. It is a further particular feature of the present invention that lumen 132 has a generally saddle shaped cross section, as seen particularly at reference numeral 134, which is sufficiently wide to enable spring 130 to be slidably displaced laterally depending on the curvature of the endoscope 104. This enhances the flexibility of the combination of endoscope 104 and the auxiliary assembly 106. It is appreciated that although provision of spring 130 is preferred, spring 130 may be replaced by a suitable, flexible, non-collapsible tube of another type. In accordance with a preferred embodiment of the present invention, useful for small intestine endoscopy, the inner diameter of spring 130 is in the range of 3-6 mm. Preferably balloon 127, when in a fully deflated state, may assume a small enough cross section to allow positioning thereof at least partially within spring 130 if needed, for example during insertion of the flexible endoscope assembly through the stomach into the small intestine.

As illustrated in FIG. 1A, a distal end 136 of spring 130 is located adjacent to a first side wall 137 of lumen 132. Spring 130 extends generally diagonally along lumen 132 such that a proximal end 138 thereof lies adjacent a second side wall 139 of lumen 132, opposite to first side wall 137.

It is appreciated that during operation of the endoscopy system 100, when the endoscope 104 and the auxiliary endoscopy assembly 106 are curved in various directions, the orientation of spring 130, particularly proximal end 138 thereof, may change appropriately.

It is seen that spring 130 is preferably angularly misaligned with a respect to the central lumen 111. Generally diagonal orientation of spring 130 within lumen 132 is particularly useful in reducing, minimizing or eliminating substantial resistance of spring 130 to bending of endoscope 104, inserted within central lumen 111.

A forward collar element 140 preferably receives distal end 136 of coil spring 130 and removably connects it to a distal end 142 of tubular sleeve 110 and thus to a distal end 144 of endoscope 104 in press-fit frictional engagement. A stretchable band 146 preferably surrounds collar element 140 and presses it into frictional engagement with distal end 142 of tubular sleeve 110 and with distal end 144 of endoscope 104. It is appreciated that lumens 112 and 132 do not extend to distal end 142 of tubular sleeve 110 and thus are not engaged by collar element 140.

It is appreciated that the lumens 111, 112 and 132 may be formed integrally as part of tubular sleeve 110 in any appropriate manner, such as by extrusion, for example. Alternatively, any one or more of lumens 111, 112 and 132 may be formed as a separate tube and may be attached to tubular sleeve 110 in any suitable manner, such as by an adhesive.

In a preferred embodiment of the present invention, tubular sleeve 110 is approximately 120-160 mm in length and spring 130 is approximately 100-130 mm in length.

Preferably the longitudinal distance between a distal edge of peripheral balloon 108 and the distal edge of tubular sleeve 110 does not exceed approximately 20 mm.

It is a particular feature of the present invention that a typical wall thickness of lumens 111, 112 and 132 of the tubular sleeve 110 is relatively thin, such as in the range of 0.15-0.7 mm, so as to provide enhanced flexibility of the tubular sleeve 110.

Preferably, for a typical endoscope diameter range of 10-13 mm, the circumference of central lumen 111 is preferably in the range of 31-41 mm, and its inner diameter is preferably 1-3 mm larger than the outer diameter of the endoscope.

Reference is now made to FIGS. 2-5, which are simplified illustrations of forward collar element 140 (FIGS. 1A & 1B). The forward collar element 140 is preferably integrally formed of plastic, such as polycarbonate, and defines first and second generally circularly curved side collar portions 200, which are arranged generally symmetrically about a longitudinal axis 202 and which are joined by a tubular portion 204, which extends rearwardly of collar portions 200 along axis 202. Tubular portion 204 preferably extends along a longitudinal axis 206 which is parallel to and spaced from longitudinal axis 202.

Tubular portion 204 is preferably formed with a generally circular rearward facing edge 208 which lies in a plane generally perpendicular to longitudinal axes 202 and 206 and a generally elliptical forward facing edge 210, which lies in a plane generally inclined with respect to longitudinal axis 206.

As seen in FIG. 2, side collar portions 200 having mutually facing edges 212, which are separated by a gap 214. A slot 216 is provided in a wall 218 of tubular portion 204, which joins side collar portions 200, generally opposite to gap 214. Slot 216 separates adjacent mutually facing edges 220 of side collar portions 200 and extends partially into tubular portion 204.

A generally circumferential outer facing recess 222 is formed on outside surfaces 224 of side collar portions 200 to accommodate stretchable band 146 (FIGS. 1A & 1B). An inner facing circumferential protrusion 226 is preferably located interiorly of tubular portion 204 and defines a forward stop for distal end 136 of spring 130 (FIGS. 1A & 1B). A pair of inner facing protrusions 228 are located interiorly of tubular portion 204, rearwardly of protrusion 226, and define engagement and locking protrusions for engagement with distal end 136 of spring 130 (FIGS. 1A & 1B).

The dimensions of gap 214 and of slot 216 may be selected so as to allow forward collar element 140 to conform to various circumferences of endoscopes. As seen in FIG. 1A, the forward collar element 140 compressively engages distal end 142 of tubular sleeve 110, which in turn surrounds distal end 144 of endoscope 104 in press-fit frictional engagement. Stretchable band 146 preferably surrounds collar element 140, which is circumferentially flexible, and presses it into this compressive engagement. The circumferential dimension of gap 214 varies as a function of the circumferential dimension of endoscope 104 and thus of distal end 142 of tubular sleeve 110.

Alternatively, tubular sleeve 110 may be obviated. In such a case, the forward collar element 140 compressively engages distal end 144 of endoscope 104 in press-fit frictional engagement. Stretchable band 146 preferably surrounds collar element 140, which is circumferentially flexible, and presses it into this compressive engagement. The circumferential dimension of gap 214 varies as a function of the circumferential dimension of endoscope 104. It is appreciated that in the embodiment wherein tubular sleeve 110 is obviated either one or both of spring 130 and balloon 108 may also be obviated. If spring 130 is obviated, external tube 122 extends into engagement with protrusions 226 and 228 of tubular portion 204 of forward collar element 140.

Figure 6A:
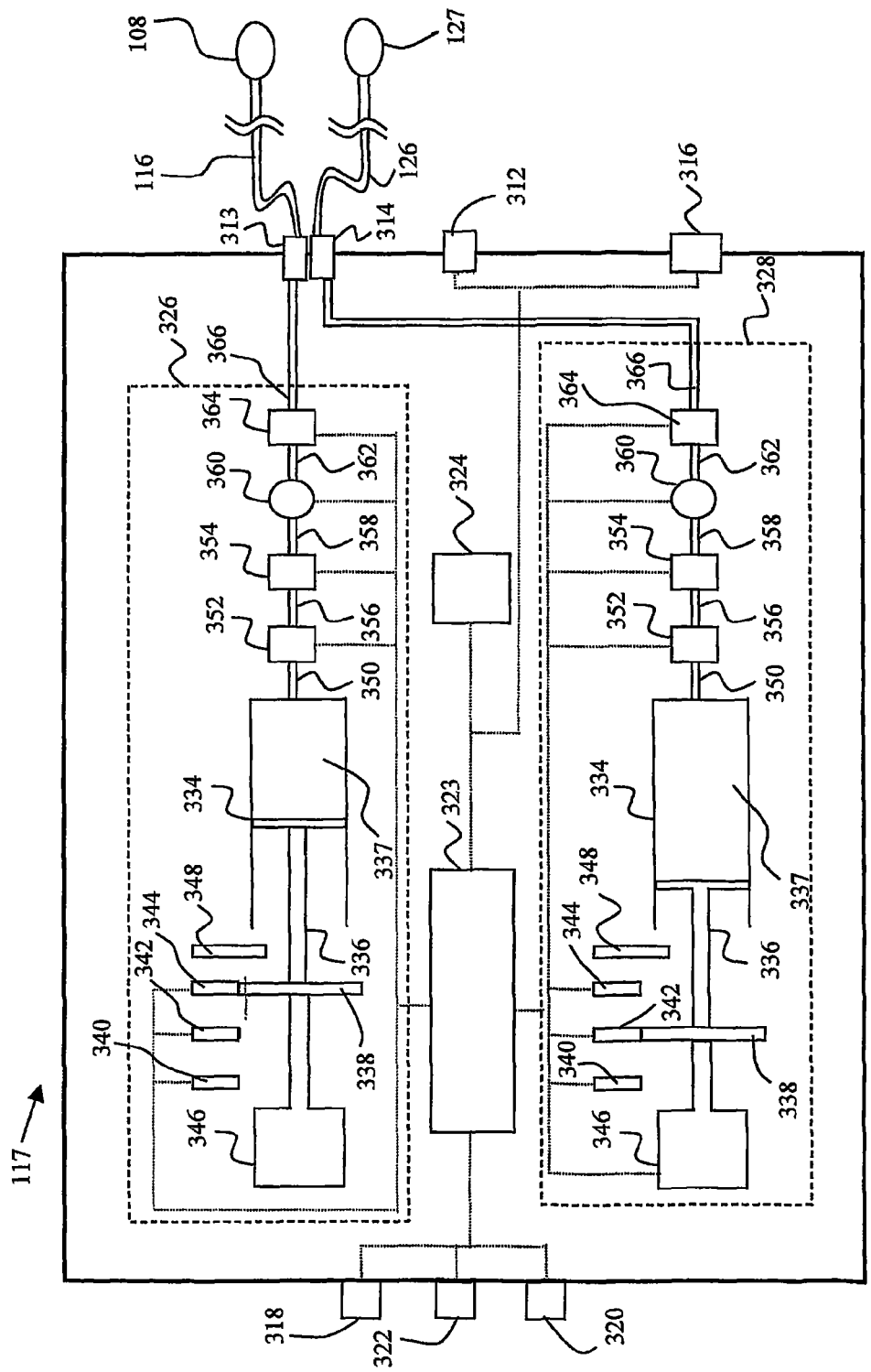
FIGS. 6A, 6B and 6C are simplified schematic illustrations of an inflation control unit forming part of the flexible endoscope system of FIGS. 1A and 1B in three different operative orientations.
Figure 6B:
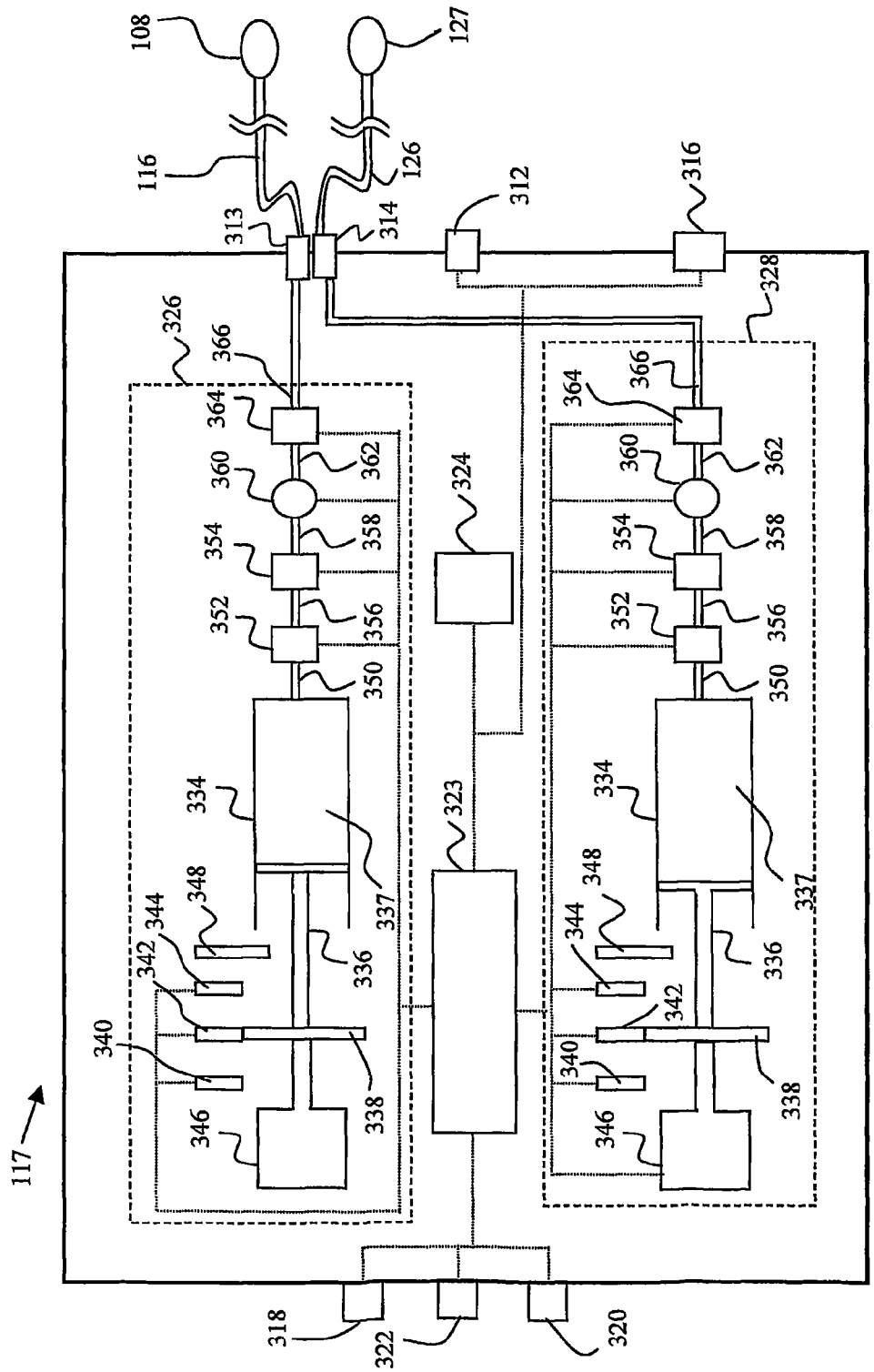
Figure 6C:
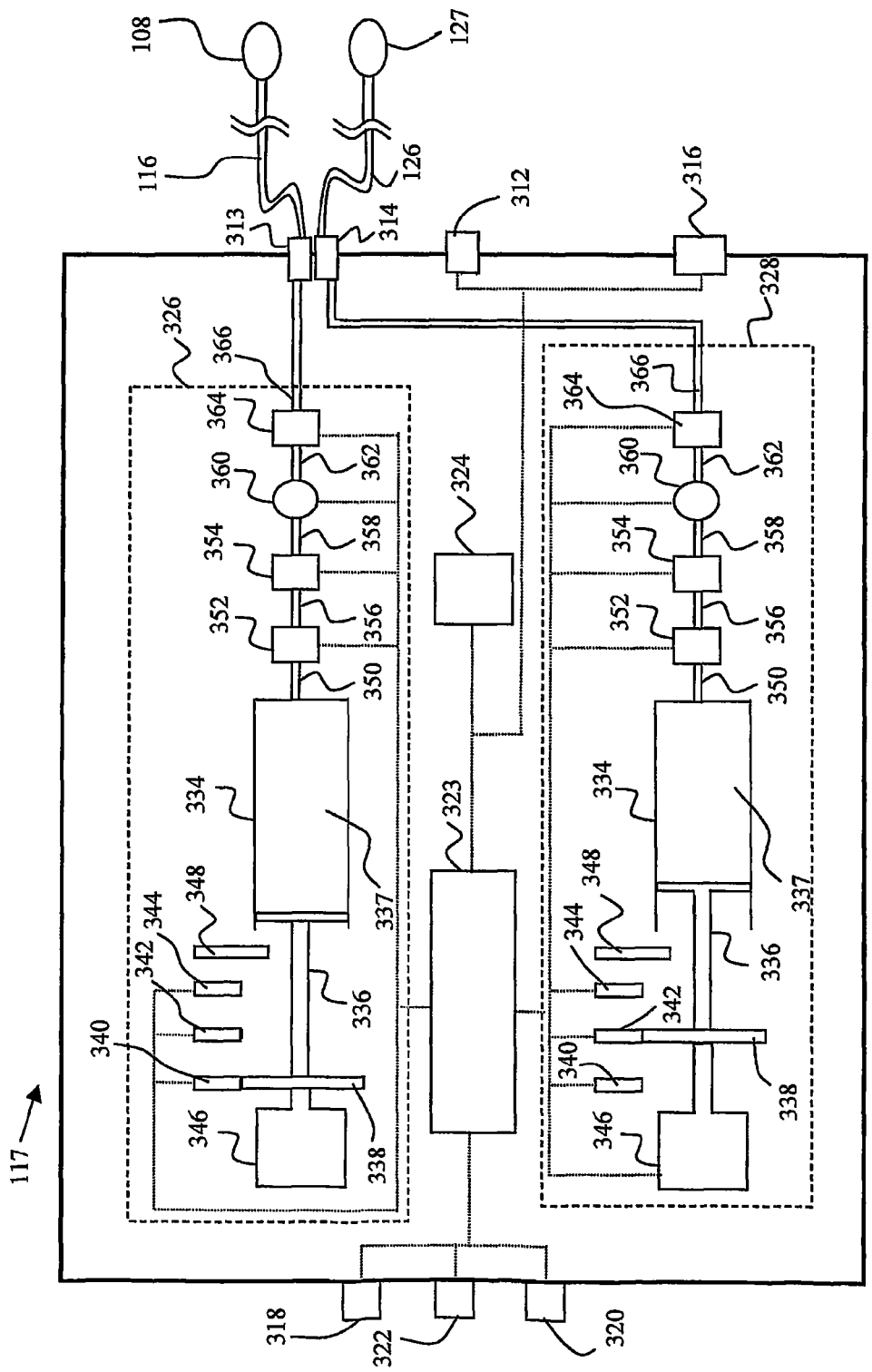

Reference is now made to FIGS. 6A, 6B and 6C, which are simplified schematic illustrations of inflation control unit 115 of the flexible endoscope system of FIGS. 1A and 1B in three different operative orientations.

In a preferred embodiment of the present invention, the inflation control assembly 115 is constructed and operative to facilitate the pneumatic inflation and/or deflation of balloons 108 and 127, which are coupled thereto by respective tubes 116 and 126.

Control unit 117 of inflation control assembly 115 is preferably an electro-mechanically operative pneumatic control subassembly which includes on its front panel a power on/off switch 312, connectors 313 and 314, for respective tubes 116 and 126, preferably female-type pneumatic connectors, and a buzzer mute switch 316.

FIGS. 6A-6C each also illustrate a foot pedal electrical connector 318, an indicator panel electrical connector 320, and a power supply electrical connector 322, all of which are preferably female-type electrical connectors.

Specific reference is now made to FIG. 6A, which is a simplified schematic illustration of the control unit 117 in an ambient inflation pressure operational state. As seen in FIG. 6A, the control unit 117 includes, in addition to the various connectors and switches described hereinabove, an electronic controller 323, a buzzer 324, and two identical inflator/deflator assemblies, respectively indicated by reference numerals 326 and 328. The electronic controller 323 is an electronic circuit which includes software that receives inputs from various components of the inflation control assembly 115 and activates various components of the inflation control assembly 115 in a manner which is described hereinbelow with reference to FIGS. 7A-7D.

Inflator/deflator assemblies 326 and 328 each include a variable volume air reservoir 334 which is coupled in a closed circuit with a corresponding balloon 108 or 127 via a corresponding tube 116 or 126. A piston 336 is movable within each air reservoir 334 to thereby vary the air volume 337 of the air reservoir 334. Associated with each piston 336 is a flange 338 arranged such that during the axial movement of piston 336 flange 338 may be located adjacent a deflated balloon status sensor 340, an ambient balloon status sensor 342 and an inflated balloon status sensor 344. Each of sensors 340, 342 and 344 detects the proximity of flange 338 and provides a corresponding output to controller 323, indicating the corresponding volume of the air volume 337 and thus the inflation/deflation status of a corresponding balloon. Sensors 340, 342 and 344 may be any suitable type of proximity sensors, such as optical sensors or capacitive sensors. An example of an appropriate sensor type is EE-SX672R, manufactured by Omron of Japan.

Piston 336 is driven linearly by a motor 346 moved inwardly or outwardly of air reservoir 334, thereby respectively decreasing or increasing the air volume 337. The operation of motor 346 is controlled by controller 323. Motor 346 may be any suitable electric motor, such as a linear motor, a rotary motor or a step motor.

A mechanical stop 348 prevents the movement of piston 336 beyond a predefined distance, by physically engaging flange 338. This limitation provides a limit on the pressure within air reservoir 334, due to the limited decrease of the air volume 337 in air reservoir 334.

Air reservoir 334 is pneumatically connected, via a first intermediate air tube 350, to a valve 352 that has two states. An example of a suitable purging valve 352 is a solenoid valve G80-24V/DC 6.5 W TWO WAY NO 1.6 mm, manufactured by Baccara of Israel. When the valve 352 is a first state, it allows air flow via first intermediate air tube 350 between air reservoir 334 and the ambient atmosphere. When 352 is in a second state, air flowing via the first intermediate air tube 350 communicates via valve 352, a balloon valve 354, and a second intermediate air tube 356 with a corresponding balloon 108 or 127 (FIGS. 1A & 1B).

Balloon valve 354 is typically a solenoid valve G80-24V/DC 6.5 W TWO WAY NO 1.6 mm, manufactured by Baccara of Israel. Balloon valve 354 may be in either one of two states, an open state and a closed state. When the balloon valve 354 is in the open state, air flowing in second intermediate air tube 356 can pass via the balloon valve 354 to a third intermediate air tube 358. When balloon valve 354 is open, third intermediate air tube 358 couples air from second intermediate air tube 356 via balloon valve 354 to a pressure sensor 360.

Pressure sensor 360 detects the air pressure in the third intermediate air tube 358. The output of pressure sensor 360 may be used by controller 323 to govern the operation of the valve 352 and of the balloon valve 354. An example of pressure sensor 360 is sensor number 6763, manufactured by Hegra Electric Ltd, Northern Way, Bury St. Edmunds, Suffolk IP32 6NN, United Kingdom.

It is appreciated that the output of pressure sensor 360 may be employed by the controller 323 for actuation of balloon valve 354, valve 352 and piston 336. It is appreciated that actuation of the above described pneumatic components may be different for different levels of pressure or vacuum which are indicated by pressure sensor 360. It is appreciated that pressure sensor 360 may comprise multiple pressure sensors, each of which may provide a digital input of a single pressure value. For instance, detection of pressure higher than 60 mbar by pressure sensor 360 may cause balloon valve 354 to be in its closed state. Detection of pressure that is below 60 mbar by the pressure sensor 360 may cause balloon valve 354 to be in its open state. Similarly, detection of a vacuum level lower than −100 mbar by pressure sensor 360 may cause the balloon valve 354 to be in its closed state.

A fourth intermediate air tube 362 allows air flow from air tube 358 via pressure sensor 360 to an overpressure release valve 364. Release valve 364 has two states, an open and a closed state. In the closed state, release valve 364 allows air flow from fourth intermediate air tube 362 to a fifth intermediate air tube 366. In the open state, release valve 364 directs the air flow from fourth intermediate air tube 362 to the ambient atmosphere. Release valve 364 is in its closed state as long as the pressure within air tube 362 is below a predefined value. Whenever the pressure in air tube 362 exceeds the predefined value, the release valve 364 is automatically shifted to its open state.

This ensures that the pressure in a fifth intermediate air tube 366 and any components connected thereto outside of the control unit 117 (FIG. 1A), does not exceed the predefined pressure value set for release valve 364, corresponding to a safe, predefined value, such as 120 mbar. The transition of the release valve 364 from its closed to its open state may be automatic as in release valve 559B-1M-1.0 psi, manufactured by Circle Seal Controls, Inc., 2301 Wardlow Circle, Corona, Calif. 92880, USA.

It is appreciated that the release valve 364 may also be controlled by a backup control mechanism.

Each intermediate air tube 366 is connected to a corresponding one of tubes 116 and 126 (FIG. 1A) via a corresponding one of connectors 313 and 314.

It is appreciated that inflator/deflator assemblies 326 and 328 can be operated using identical components and by implementing the same or different algorithms, such that, for example balloon 108 may operate at a maximum inflation of 60 mbar, while balloon 127 may operate at a maximum inflation of 90 mbar.

Reference is now made additionally to FIGS. 7A-7D, which are simplified flow charts illustrating preferred modes of operation of the inflation control assembly 115 of FIGS. 6A-6C. An indicated above, control of the operation of inflation control assembly 115 is provided principally by controller 323 based on various sensor inputs, described hereinabove.

It is appreciated that the implementation of controller 323 may involve any suitable technology, for example, the use of embedded firmware, loading software from a digital memory device and loading software from an external source.

Figure 7A:
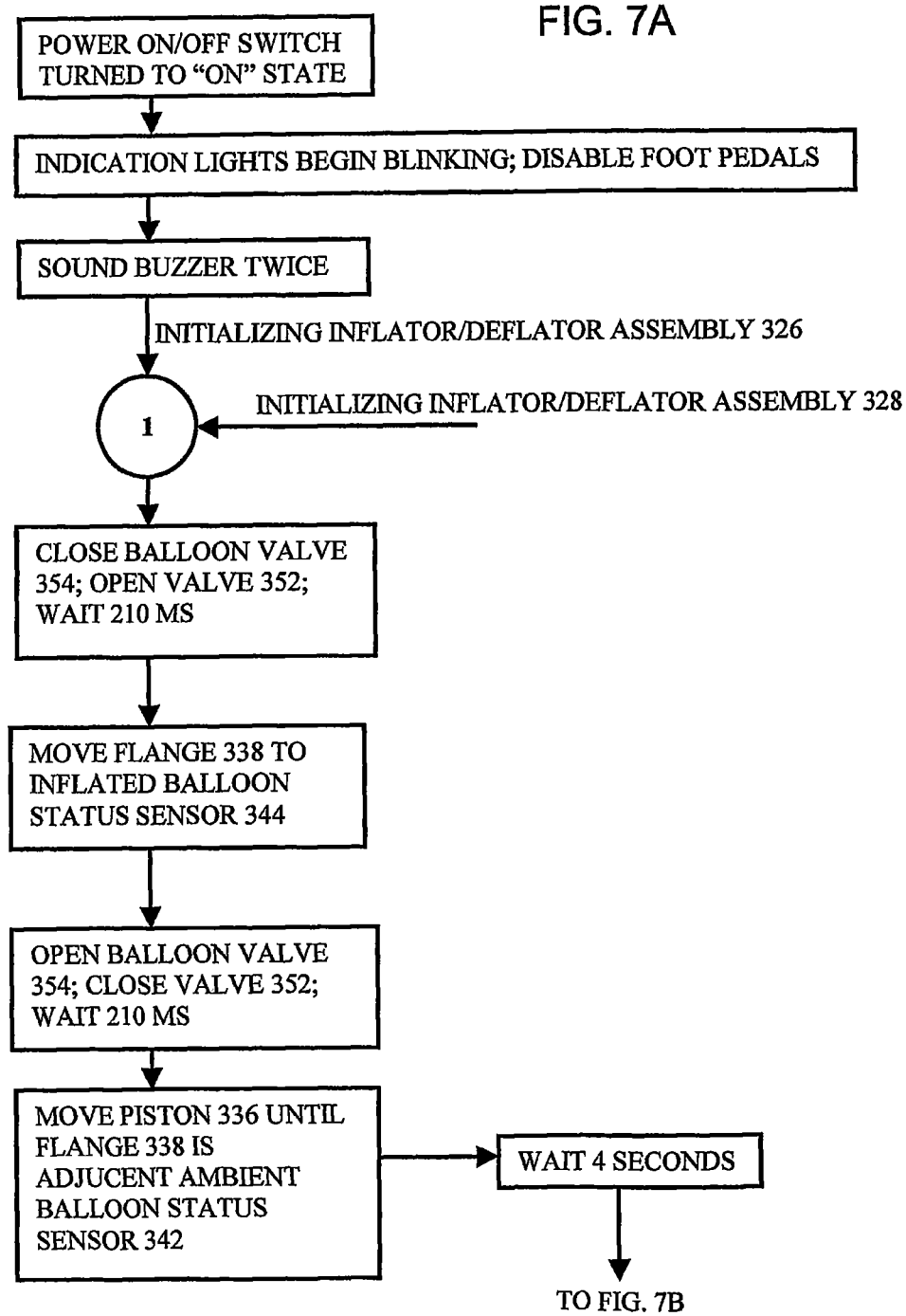
FIGS. 7A, 7B, 7C and 7D are simplified flow charts illustrating preferred modes of operation of the inflation control unit of FIGS. 6A-6C.
Figure 7B:
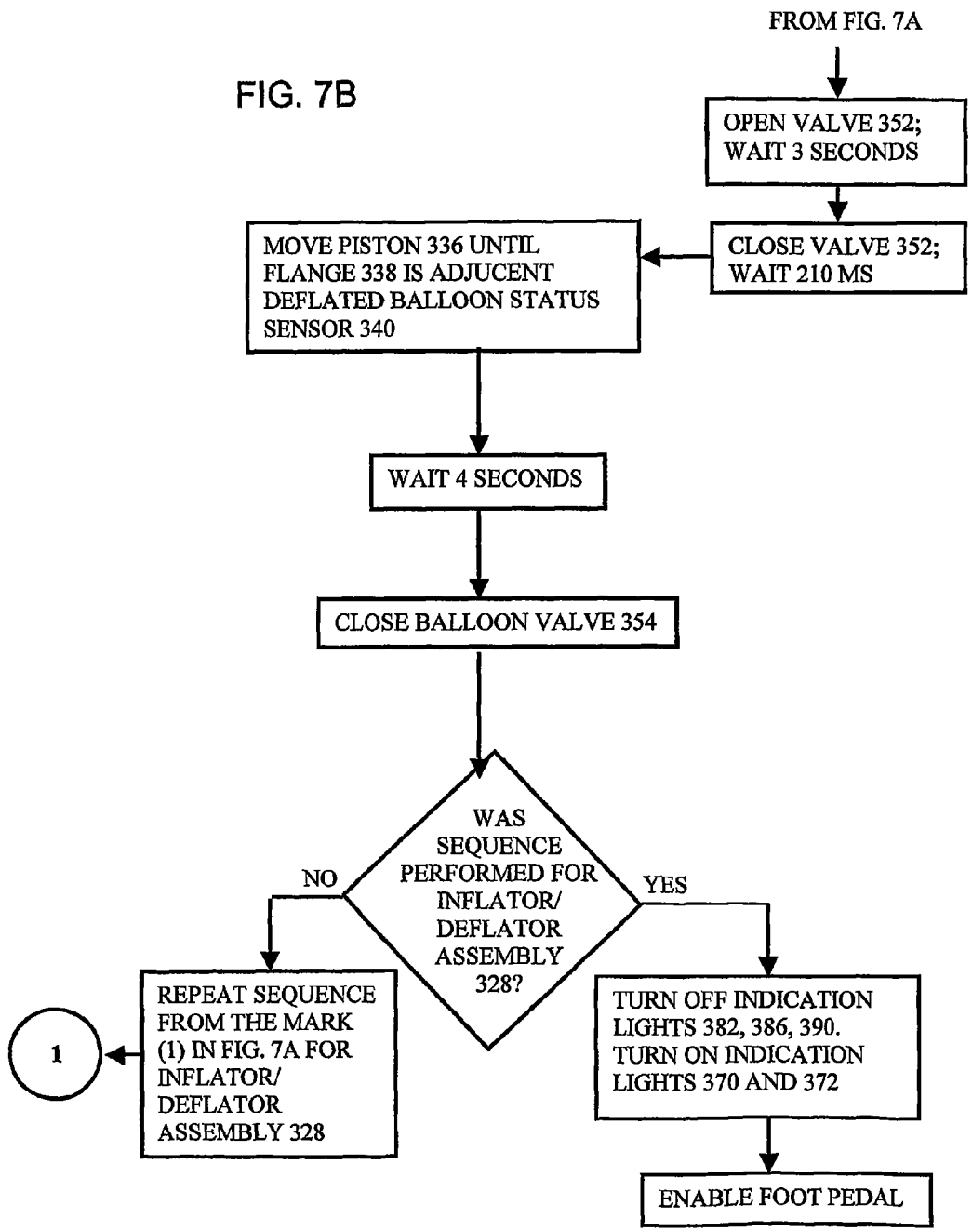

FIGS. 7A and 7B illustrate initialization functionality Which is performed automatically once the power switch 312 is switched to its on state. A primary purpose of the initialization functionality is to ensure that, whatever is the initial state of the control unit 117 (FIG. 1A), prior to operation, balloons 108 and 127 are in their fully deflated (vacuum) operational states.

As seen in FIGS. 7A and 7B, following powering on of the inflation control assembly 115 (FIG. 1A), indication lights on panel 119 (FIG. 1A) blink, foot pedals 118 are disabled and buzzer 324 (FIGS. 6A-6C) sounds.

At this stage, initialization of one of the two identical inflator/deflator assemblies 326 and 328 begins. Once initialization of one of the identical inflator/deflator assemblies is completed, initialization of the other of the identical inflator/deflator assemblies takes place. In the illustrated example, initialization of inflator/deflator assembly 326 occurs first, starting with closing of balloon valve 354 and opening of valve 352 thereof. After a predetermined period of time, typically 210 ms, piston 336 is positioned by motor 346 such that flange 338 is adjacent inflated balloon status sensor 344. This is the state illustrated by FIG. 6A.

The balloon valve 354 is then opened and valve 352 is closed. Following a predetermined time duration, typically 210 ms, piston 336 is moved by motor 346 such that flange 338 is adjacent ambient balloon status sensor 342. This is the state illustrated by FIG. 6B.

Following a further predetermined time duration, typically 4 seconds, valve 352 is opened. Following an additional predetermined time duration, typically 3 seconds, valve 352 is closed.

Following a still further predetermined time duration, typically 210 ms, piston 336 is moved by motor 346 such that flange 338 is adjacent deflated balloon status sensor 340. This is the state illustrated by FIG. 6C.

Following yet another predetermined time duration, typically four seconds, balloon valve 354 is closed. This completes initialization of inflator/deflator assembly 326 and is followed by initialization of inflator/deflator assembly 328, which includes identical steps to those described above for initialization of inflator/deflector assembly 326.

Following completion of initialization of inflator/deflator assemblies 326 and 328, the indication lights on panel 119 (FIG. 1A) stop blinking and foot pedals 118 are enabled. At this stage, two vacuum indication lights, here designated by reference numerals 370 and 372 (FIG. 1A) are illuminated to indicate the presence of vacuum in balloons 108 and 127 (FIG. 1A).

Figure 7C:
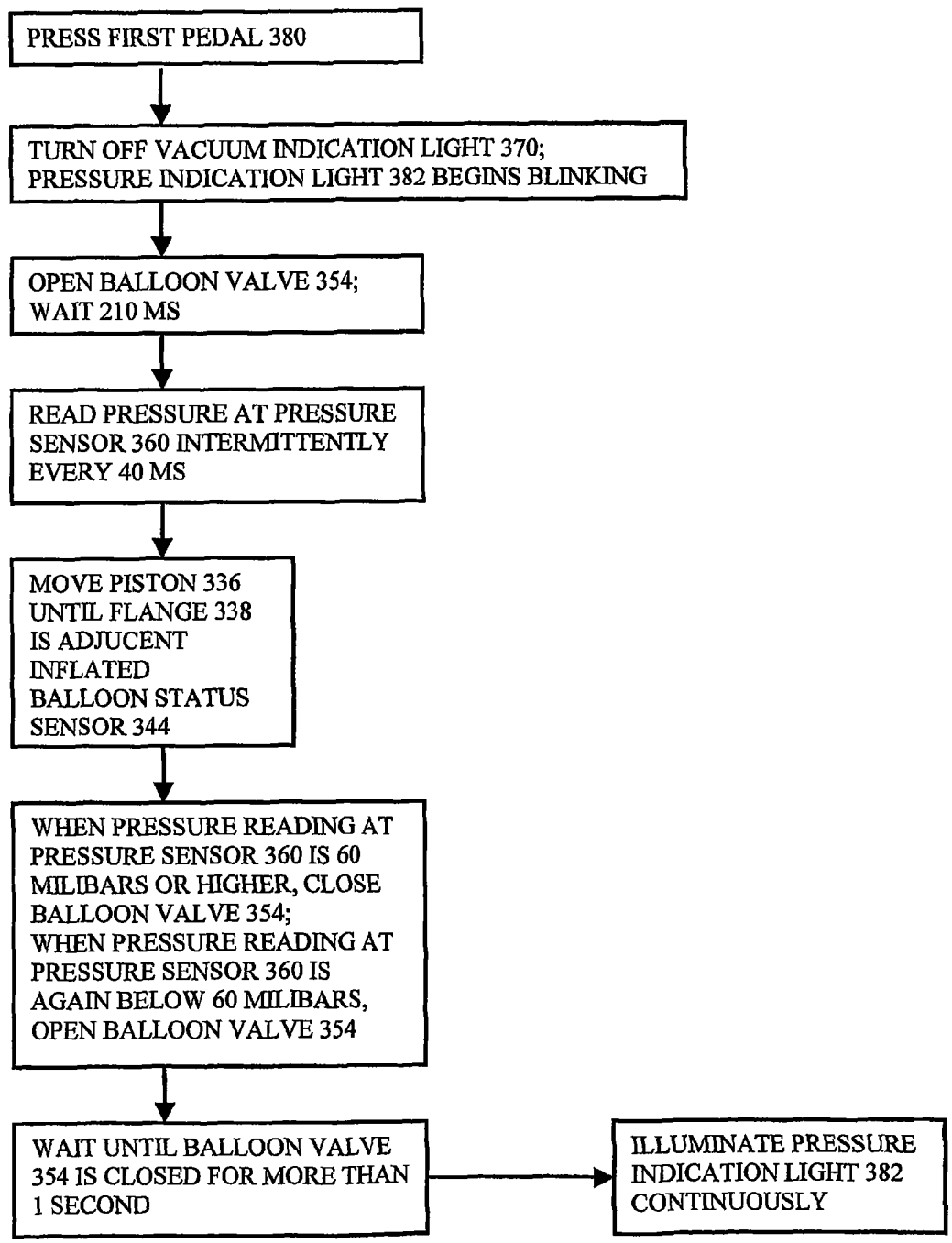

At this stage, normally inflation of one of balloons 108 and 127 takes place. Usually, but not necessarily, inflation of balloon 108 takes place first. As seen in FIG. 7C, inflation of balloon 108 is initiated by an operator pressing on one of the foot pedals 118, here designated by reference numeral 380, to send a signal to controller 323 (FIGS. 6A-6C) to initiate inflation of balloon 108. Indication light 370 is extinguished and another one of the indication lights on panel 119, a pressure indication light for balloon 108, here designated by reference numeral 382 (FIG. 1A), begins blinking. Balloon valve 354 is opened. Following a predetermined time duration, typically 210 ms, piston 336 is positioned by motor 346 such that flange 338 is adjacent inflated balloon status sensor 344. This is the state illustrated by FIG. 6A.

At this stage, piston 336 is pressurized to a relatively high pressure, typically 200 mbar and the desired pressure at balloon 108 is typically 60 mbar. Inflation of the balloon 108 is accomplished by intermittently opening and closing balloon valve 354 and monitoring the pressure at sensor 360, which is connected in series between piston 336 and balloon 108. When the desired pressure at sensor 360 remains steady at 60 mbar for at least a predetermined time, typically one second, balloon valve 354 remains closed and inflation of balloon 108 is considered to be completed and indicator light 382 is illuminated continuously. Even following completion of inflation of balloon 108, sensor 360 continues to monitor the pressure and if and when necessary, balloon valve 354 may be opened to top up the pressure at balloon 108.

Inflation of balloon 127 is initiated by an operator pressing on one of the foot pedals 118, here designated by reference numeral 384, to send a signal to controller 323 (FIGS. 6A-6C) to initiate inflation of balloon 127. Indication light 372 is extinguished and another one of the indication lights on panel 119, a pressure indication light for balloon 108, here designated by reference numeral 386 (FIG. 1A), begins blinking. Balloon valve 354 is opened. Following a predetermined time duration, typically 210 ms, piston 336 is positioned by motor 346 such that flange 338 is adjacent inflated balloon status sensor 344. This corresponds to the state illustrated by FIG. 6A.

At this stage, piston 336 is pressurized to a relatively high pressure, typically 200 mbar and the desired pressure at balloon 127 is typically 60 mbar. Inflation of the balloon 127 is accomplished by intermittently opening and closing balloon valve 354 and monitoring the pressure at sensor 360, which is connected in series between piston 336 and balloon 127. When the desired pressure at sensor 360 remains steady at 60 mbar for at least a predetermined time, typically one second, balloon valve 354 remains closed and inflation of balloon 127 is considered to be completed and indicator light 386 is illuminated continuously. Even following completion of inflation of balloon 127, sensor 360 continues to monitor the pressure and if and when necessary, balloon valve 354 may be opened to top up the pressure at balloon 127.

Figure 7D:
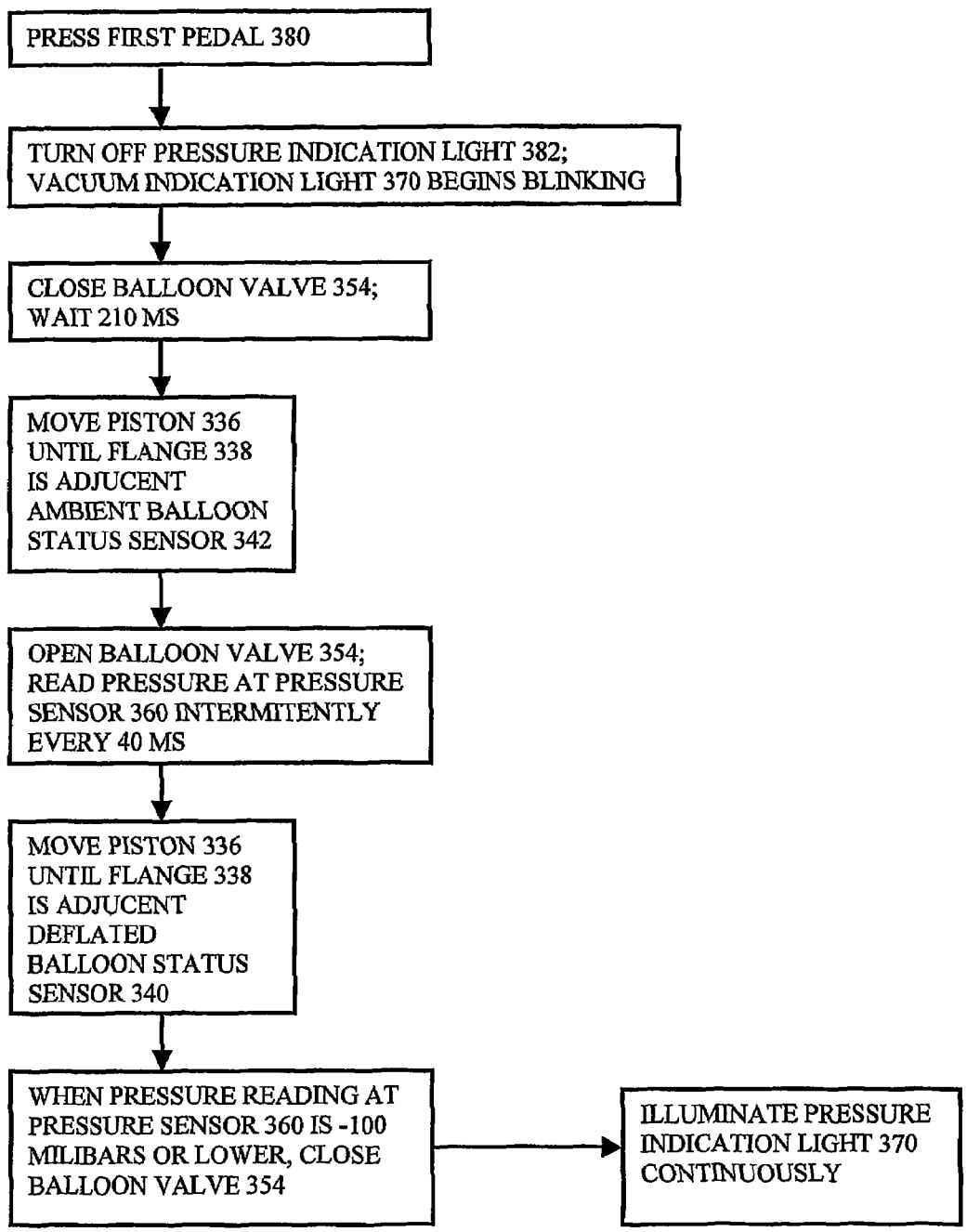

As seen in FIG. 7D, deflation of balloon 108 takes place by an operator pressing on foot pedal 380, to send a signal to controller 323 (FIGS. 6A-6C) to initiate deflation of balloon 108. Indication light 382 is extinguished and vacuum indication light 370 begins blinking. Balloon valve 354 is closed. Following a predetermined time duration, typically 210 ms, piston 336 is positioned by motor 346 such that flange 338 is adjacent ambient balloon status sensor 342 and balloon valve 354 is opened. This is the state illustrated by FIG. 6B.

At this stage, piston 336 is at approximately ambient pressure. Piston 336 is then positioned by motor 346 such that flange 338 is adjacent deflated balloon status sensor 340. This is the state illustrated by FIG. 6C.

Deflation of the balloon 108 is accomplished by monitoring the pressure at sensor 360. When the desired pressure at sensor 360 reaches a negative level of −100 mbar, balloon valve 354 is closed, deflation of balloon 108 is considered to be completed and indicator light 370 is illuminated continuously. Even following completion of deflation of balloon 108, sensor 360 continues to monitor the pressure inside balloon 108.

Deflation of balloon 127 takes place by an operator pressing on foot pedal 384, to send a signal to controller 323 (FIGS. 6A-6C) to initiate deflation of balloon 127. Indication light 386 is extinguished and vacuum indication light 372 begins blinking. Balloon valve 354 is closed. Following a predetermined time duration, typically 210 ms, piston 336 is positioned by motor 346 such that flange 338 is adjacent ambient balloon status sensor 342 and balloon valve 354 is opened. This is a state corresponding to the state illustrated in FIG. 6B.

At this stage, piston 336 is at approximately ambient pressure. Piston 336 is then positioned by motor 346 such that flange 338 is adjacent deflated balloon status sensor 340. This is the state illustrated by FIG. 6C.

Deflation of the balloon 127 is accomplished by monitoring the pressure at sensor 360. When the desired pressure at sensor 360 reaches a negative level of −100 mbar, balloon valve 354 is closed, deflation of balloon 127 is considered to be completed and indicator light 372 is illuminated continuously. Even following completion of deflation of balloon 127, sensor 360 continues to monitor the pressure inside balloon 127.

One of the indicator lights on panel 119 may be a failure indication light, here designated by reference numeral 390. This light may be illuminated when any of the functionalities described above fails to be fully performed.

Figure 8:
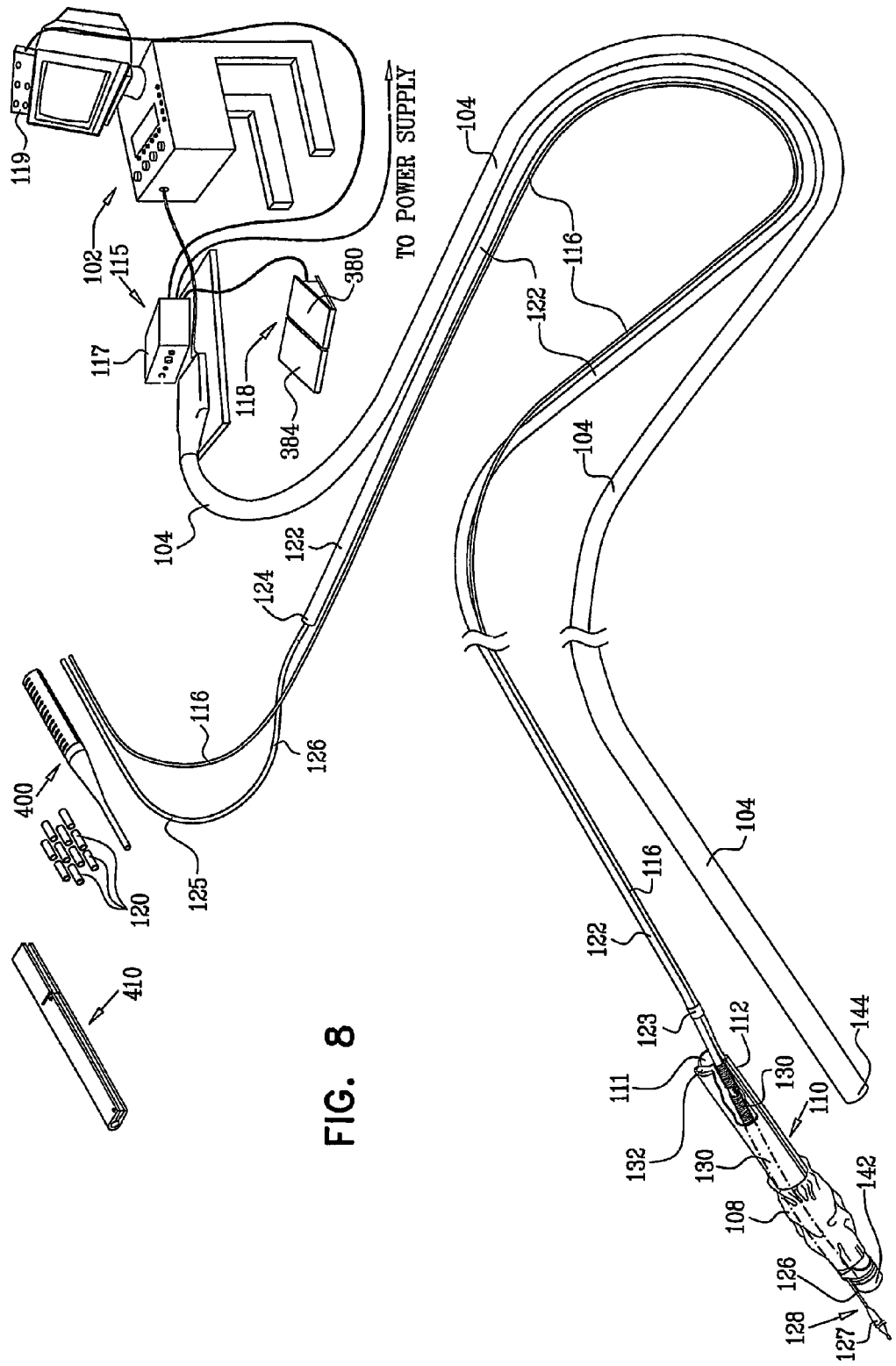
FIG. 8 is a simplified illustration of the flexible endoscope system of FIGS. 1A and 1B in a pre-preparation stage.

Reference is now made to FIG. 8, which is a simplified illustration of the flexible endoscope system of FIGS. 1A and 1B in a pre-preparation stage. Additional elements used in preparation and operation of the flexible endoscope system of FIGS. 1A and 1B are illustrated in FIG. 8. These include a flexible band mounting assembly 400 for mounting of flexible bands 120 (FIG. 1A) and an endoscope tool manipulator assembly 410.

Figure 9B:
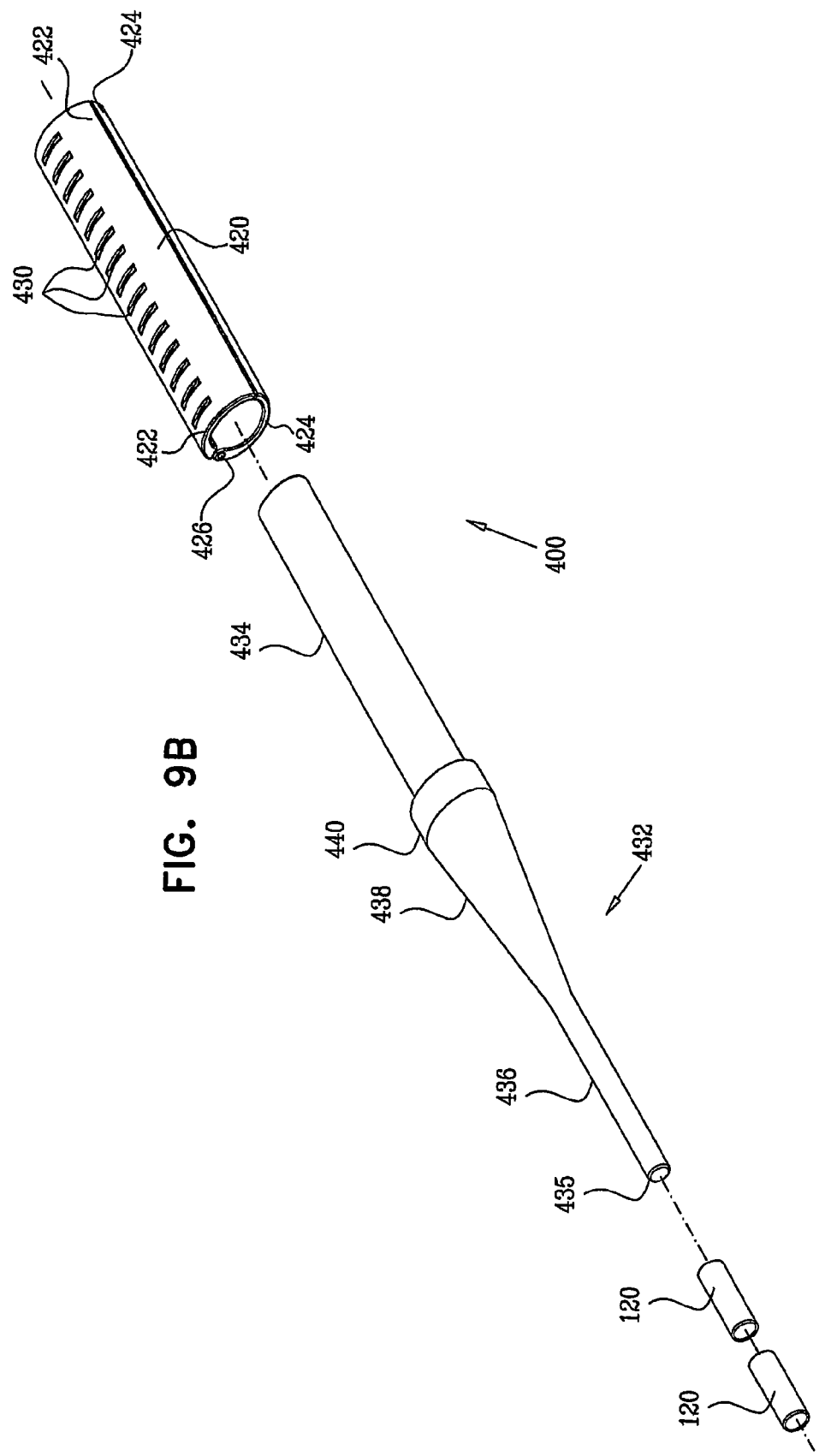

Reference is now made to FIGS. 9A and 9B, which are respective simplified assembled and exploded view illustrations of a flexible band mounting assembly used for mounting flexible bands 120 in preparation of the flexible endoscope system of FIGS. 1A and 1B for use. As seen in FIGS. 9A and 9B, the flexible band mounting assembly 400 comprises a hinged, generally cylindrical mounting band holder 420 which includes first and second portions 422 and 424, which are hinged together by one or more hinges 426 and which define, when in a mutually closed orientation, as seen in FIGS. 9A and 9B, an elongate, hollow body having a generally elliptical cross-section and having a series of rolled flexible band retaining slots 430 formed on first portion 422.

Flexible band mounting assembly 400 also preferably includes an elongate tapered flexible band roller and stretcher element 432 which includes a shaft portion 434 onto which band holder 420 is seated during flexible band mounting on band holder 420. Flexible band roller and stretcher element 432 preferably includes a circumferentially tapered end 435 which leads to a generally cylindrical flexible band rolling portion 436, rearward of which is a tapered rolled flexible band stretching portion 438, followed by an intermediate portion 440 which is preferably of a cross-sectional configuration identical to that of band holder 420.

Figure 10B:
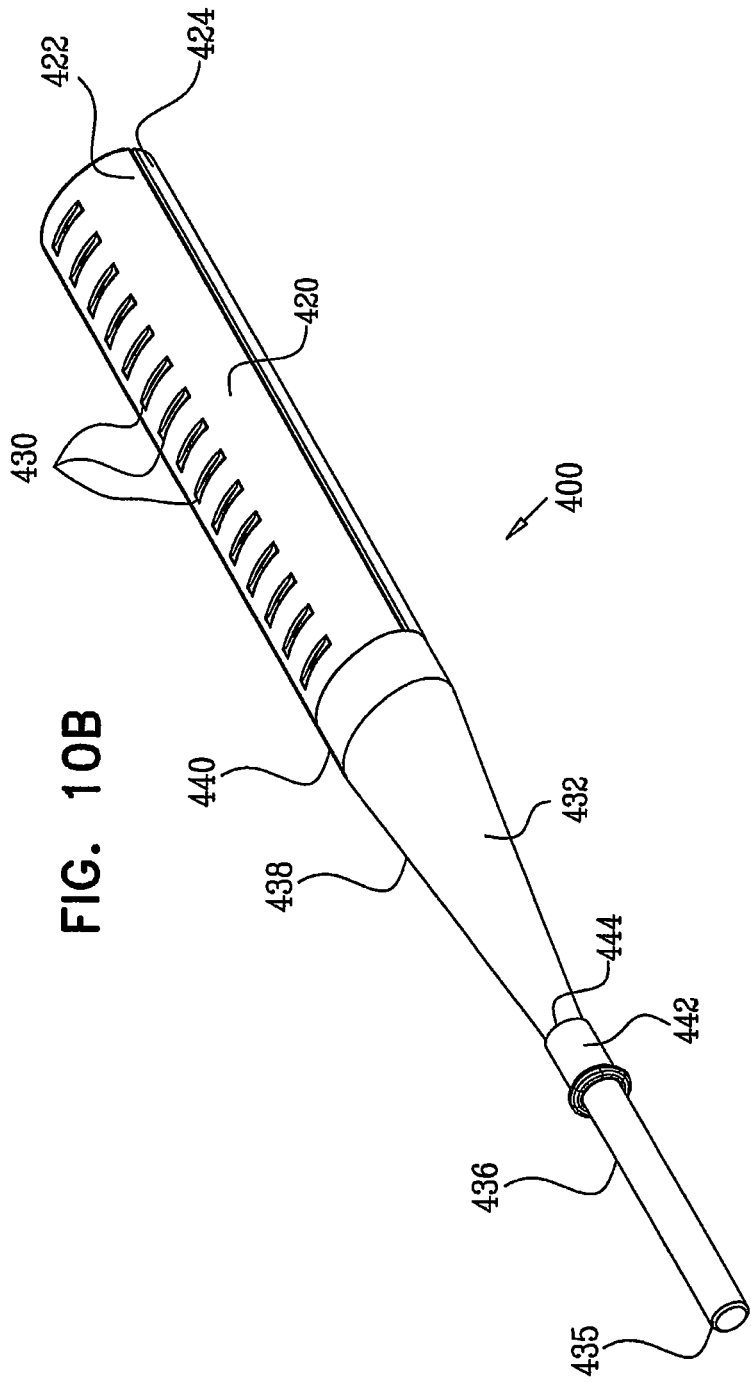
Figure 10D:
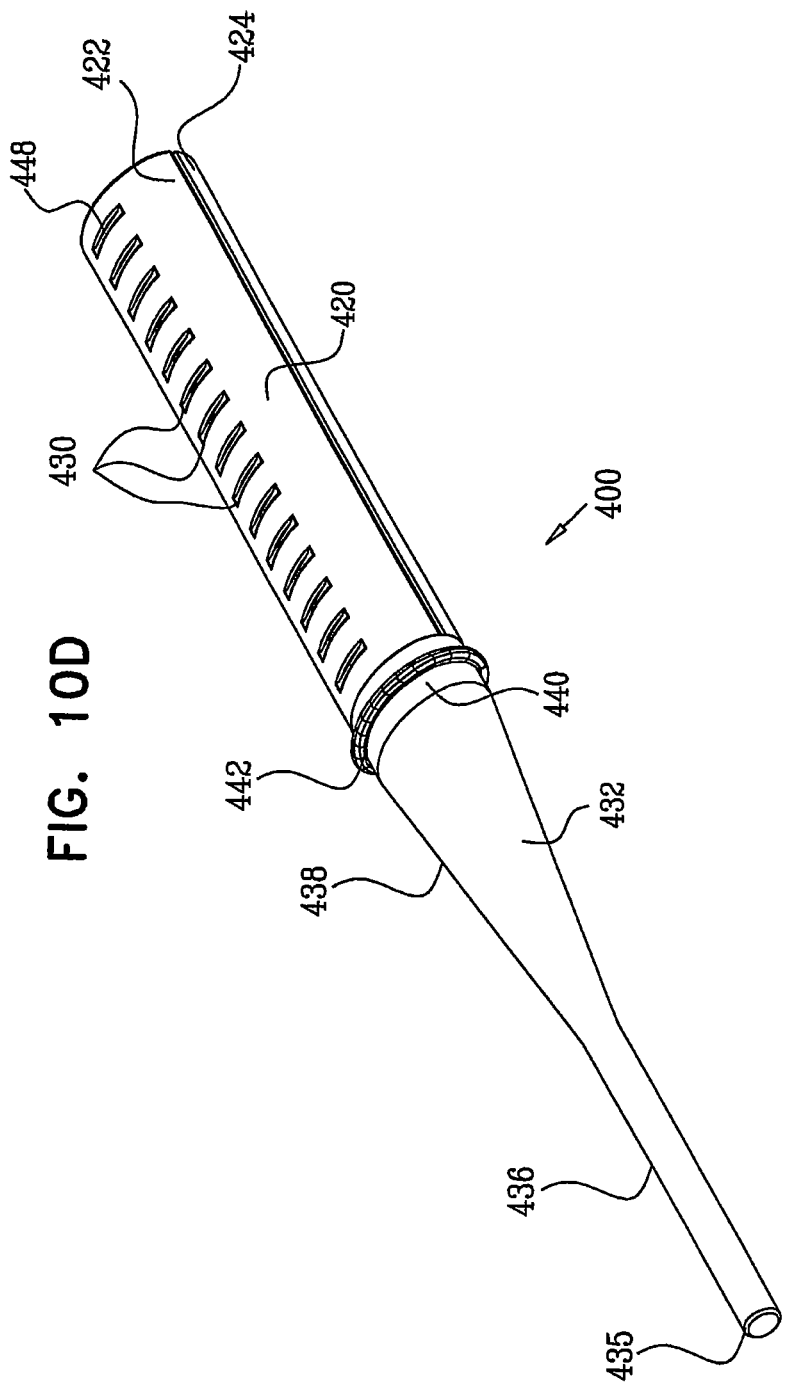
Figure 10E:
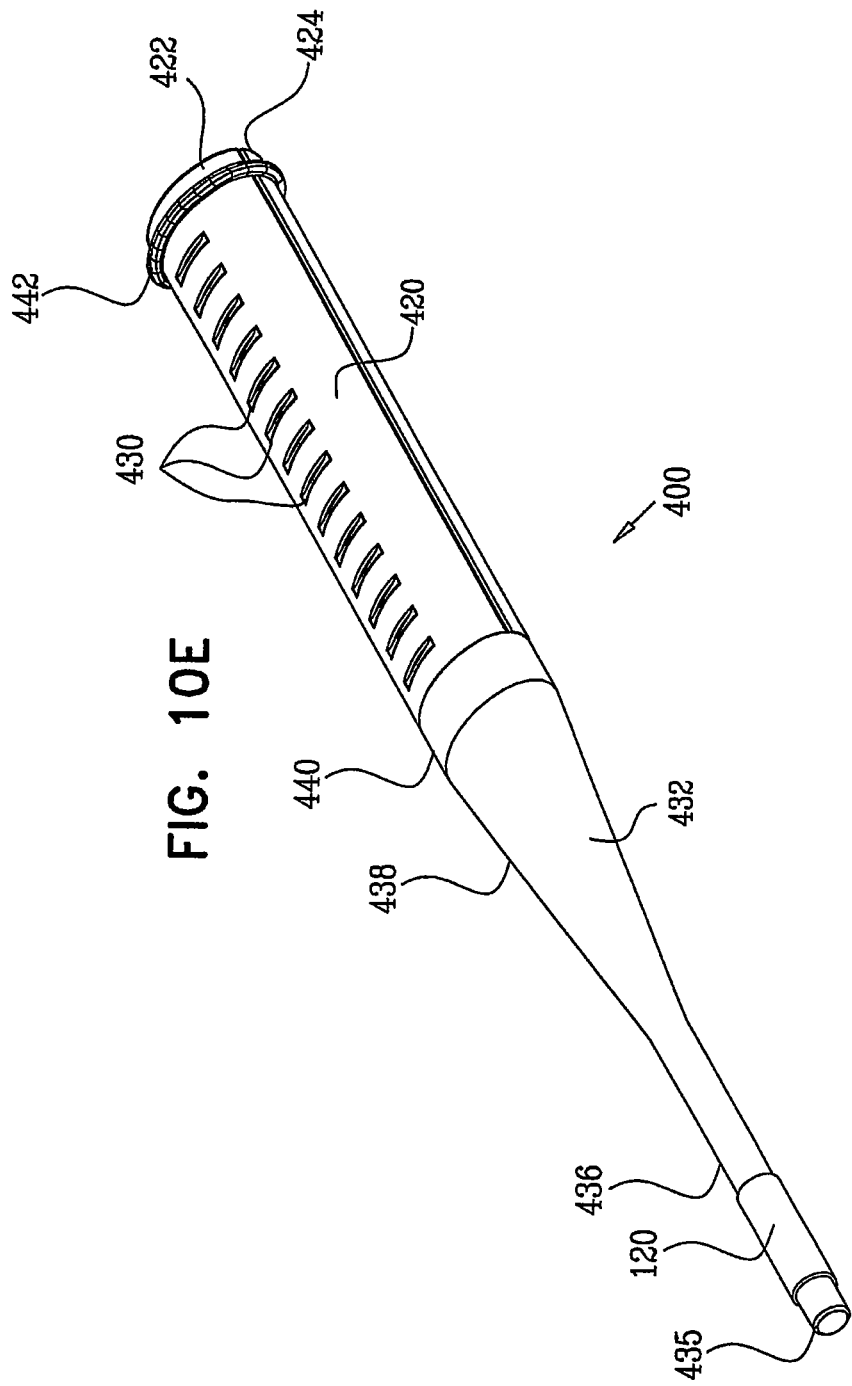

Reference is now made to FIGS. 10A-10H, which are simplified illustrations of loading flexible bands 120 onto flexible band holder 420. FIG. 10A shows a first flexible band, here designated by reference numeral 442, slid over portion 436, such that its forward end 444 abuts on tapered portion 438 and a rearward end 446 thereof is free. FIG. 10B shows the rearward end of band 442 being rolled, typically manually, towards end 444 thereof. FIG. 10C shows band 442 fully rolled and located at a junction between portions 436 and 438 of element 432. FIG. 10D shows band 442, after having rolled over tapered portion 438 and having been stretched, located on intermediate portion 440. FIG. 10E shows rolled band 442 positioned on a first one of flexible band retaining slots 430, designated by reference numeral 448 in FIG. 10D, as well as another band 120 awaiting rolling.

FIG. 10F illustrates additional rolled bands 450 respectively positioned on flexible band retaining slots 430 lying rearward of retaining slot 448 as well as another band 120 awaiting rolling. FIG. 10G shows flexible band holder 420 fully loaded with rolled bands 450 at all of its flexible band retaining slots 430. FIG. 10H, shows slidable detachment of fully loaded flexible band holder 420 from shaft portion 434 of flexible band roller and stretcher element 432.

Reference is now made to FIGS. 11A, 11B, 11C, 11D, 11E, 11F, 11G, 11H, 11I, 11J, 11K and 11L, which are simplified illustrations of unloading rolled flexible bands 450 from the flexible band holder 420 and placement of the rolled flexible bands 450 onto the flexible endoscope assembly, including endoscope 104, tube 116, tube 126 and external tube 122, at appropriate locations therealong.

Figure 11A:
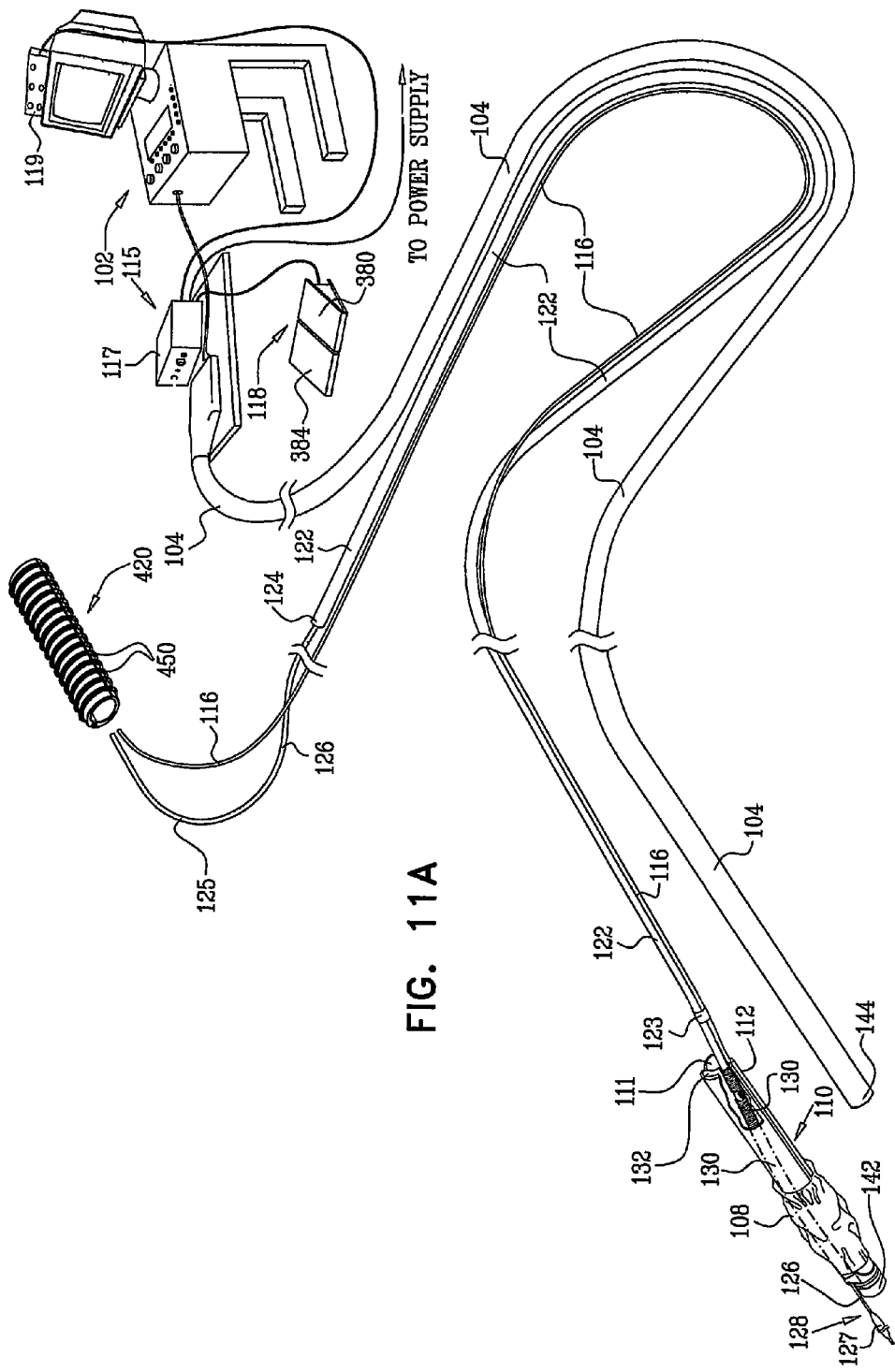
Figure 11B:
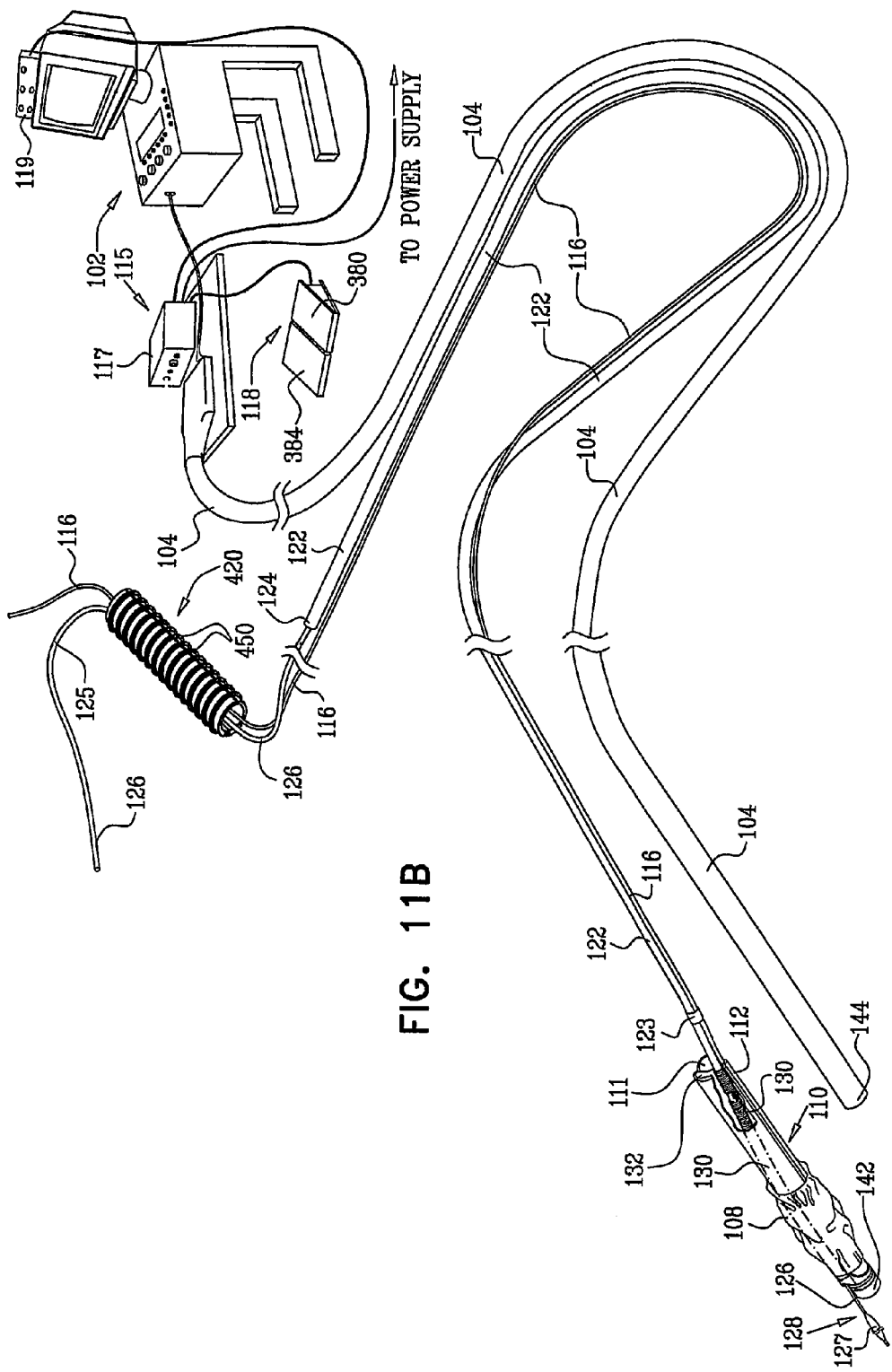
Figure 11C:
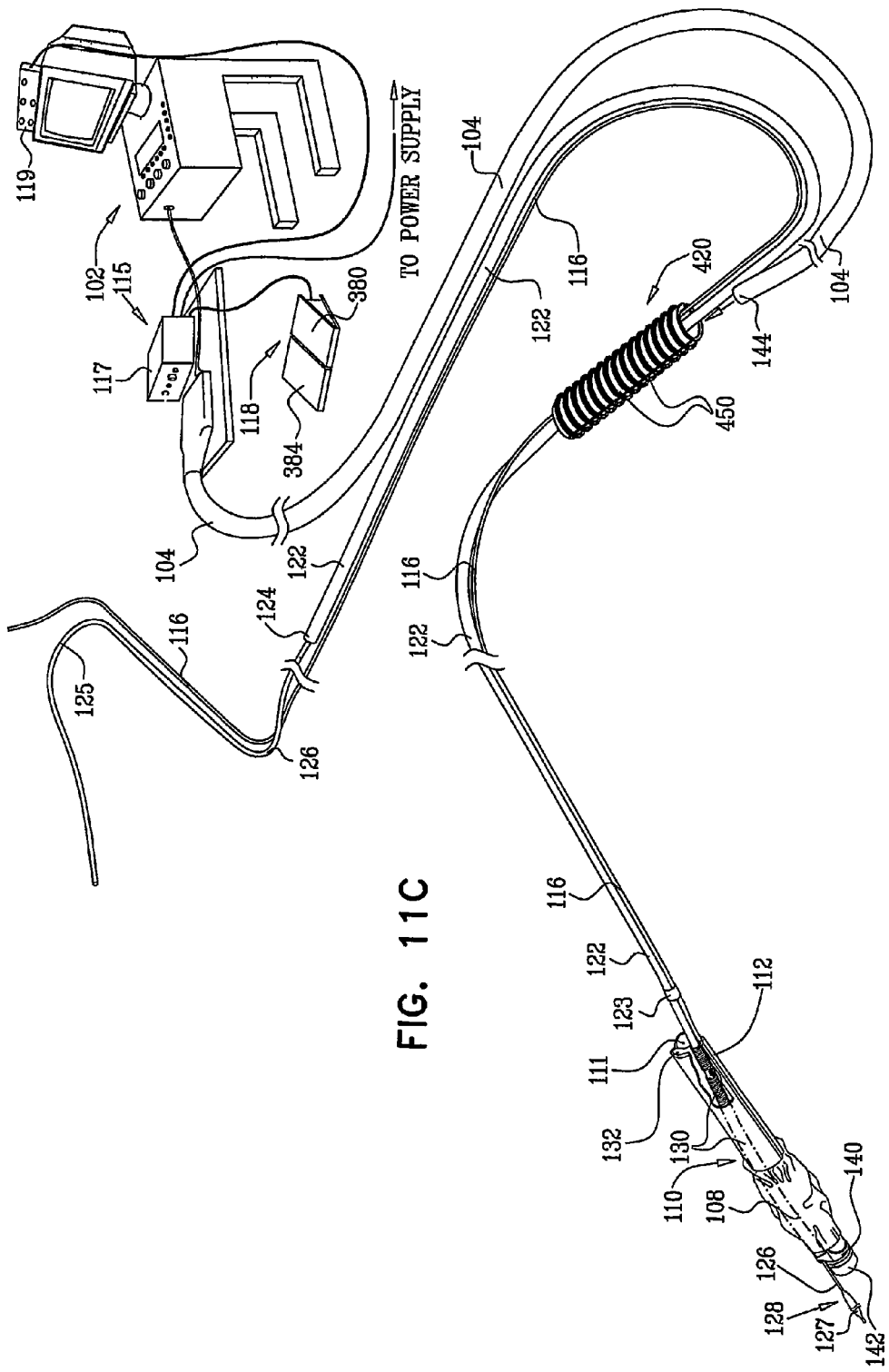
Figure 11D:
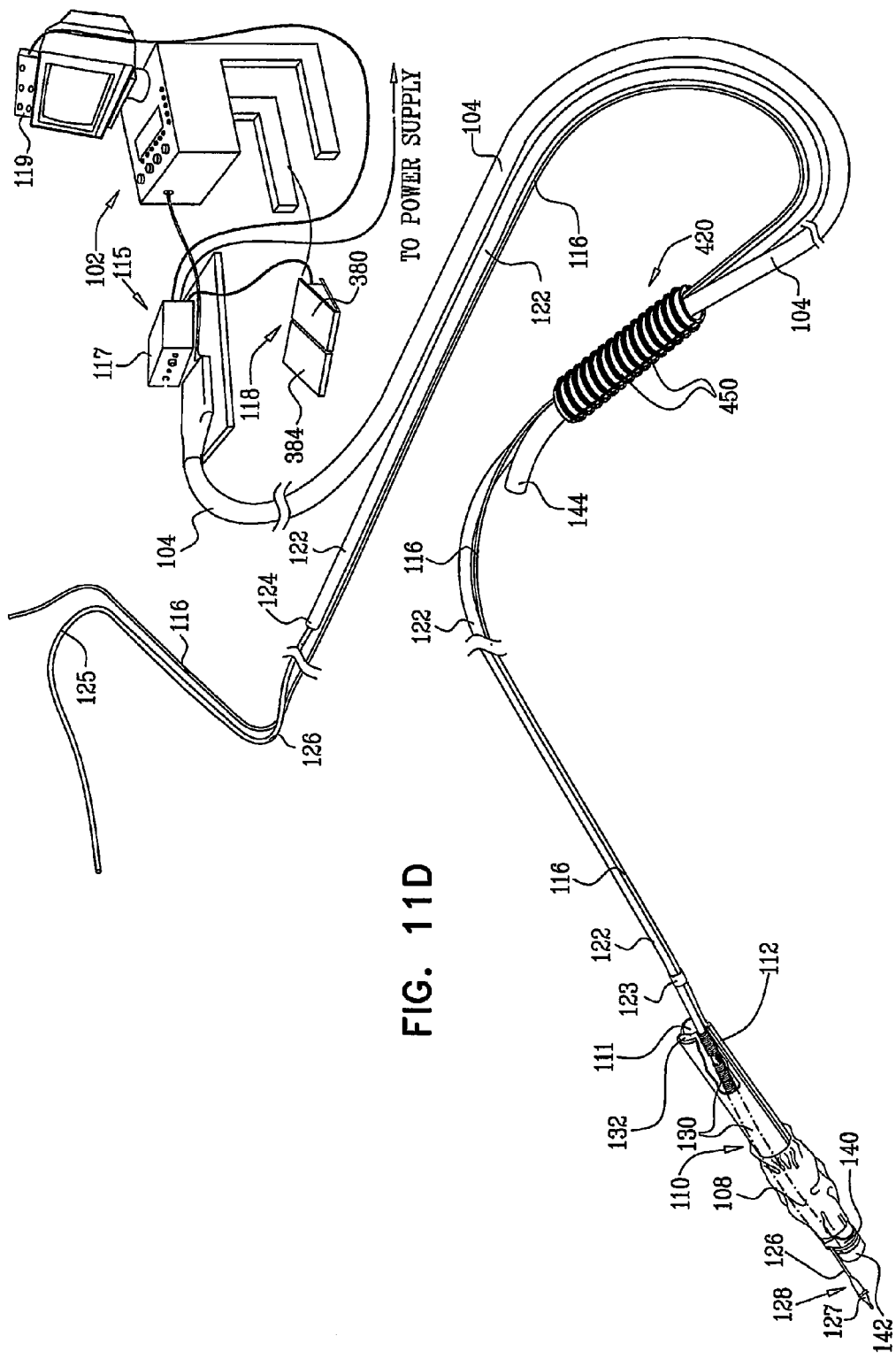
Figure 11E:
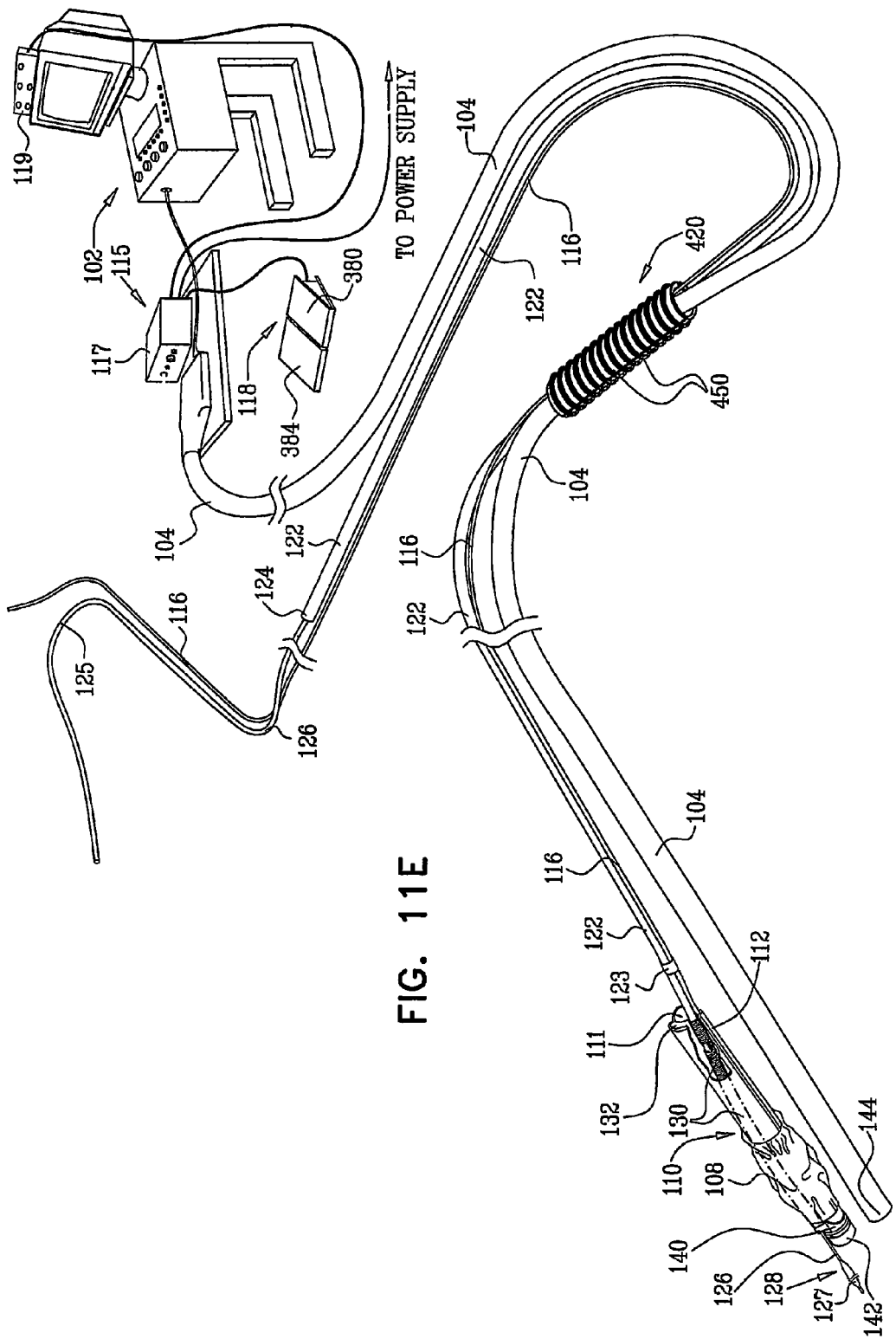
Figure 11F:
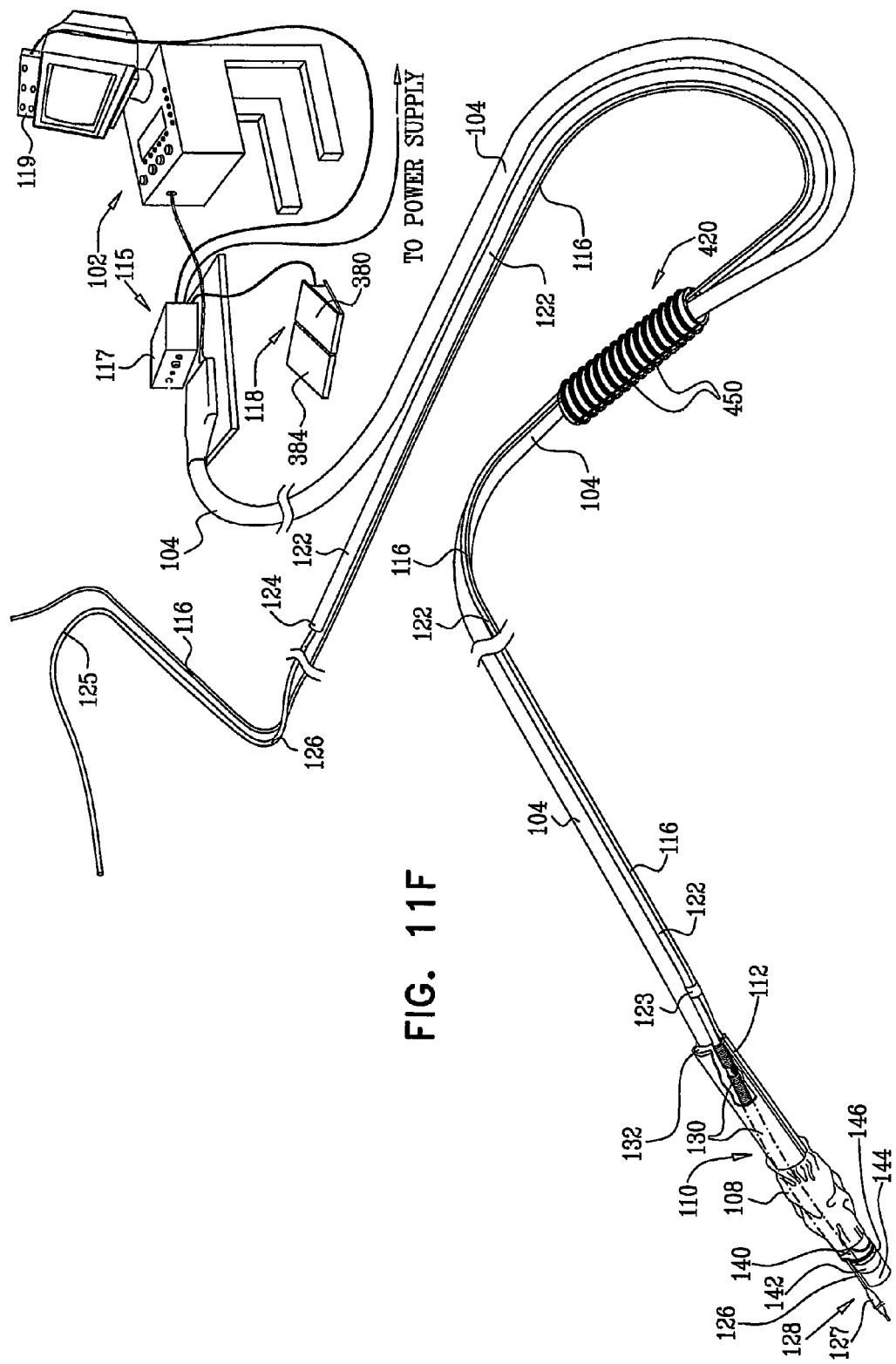

As seen in FIG. 11A, the loaded flexible band holder 420 is located outside proximal ends of tubes 116 and 126. FIG. 11B shows the loaded flexible band holder 420 overlying tubes 116 and 126. FIG. 11C shows the loaded flexible band holder 420 overlying tube 116 and external tube 122, through which extends tube 126, at a location just forward of the distal end 144 of endoscope 104. FIG. 11D shows distal end 144 of endoscope 104 threaded through flexible band holder 420. FIG. 11E shows loaded flexible band holder 420 overlying endoscope 104, tube 116 and external tube 122, through which extends tube 126. FIG. 11F shows distal end 144 of endoscope 104 inserted in central lumen 111 of sleeve 110 (FIG. 1A) and fixed in place by band 146.

Figure 11G:
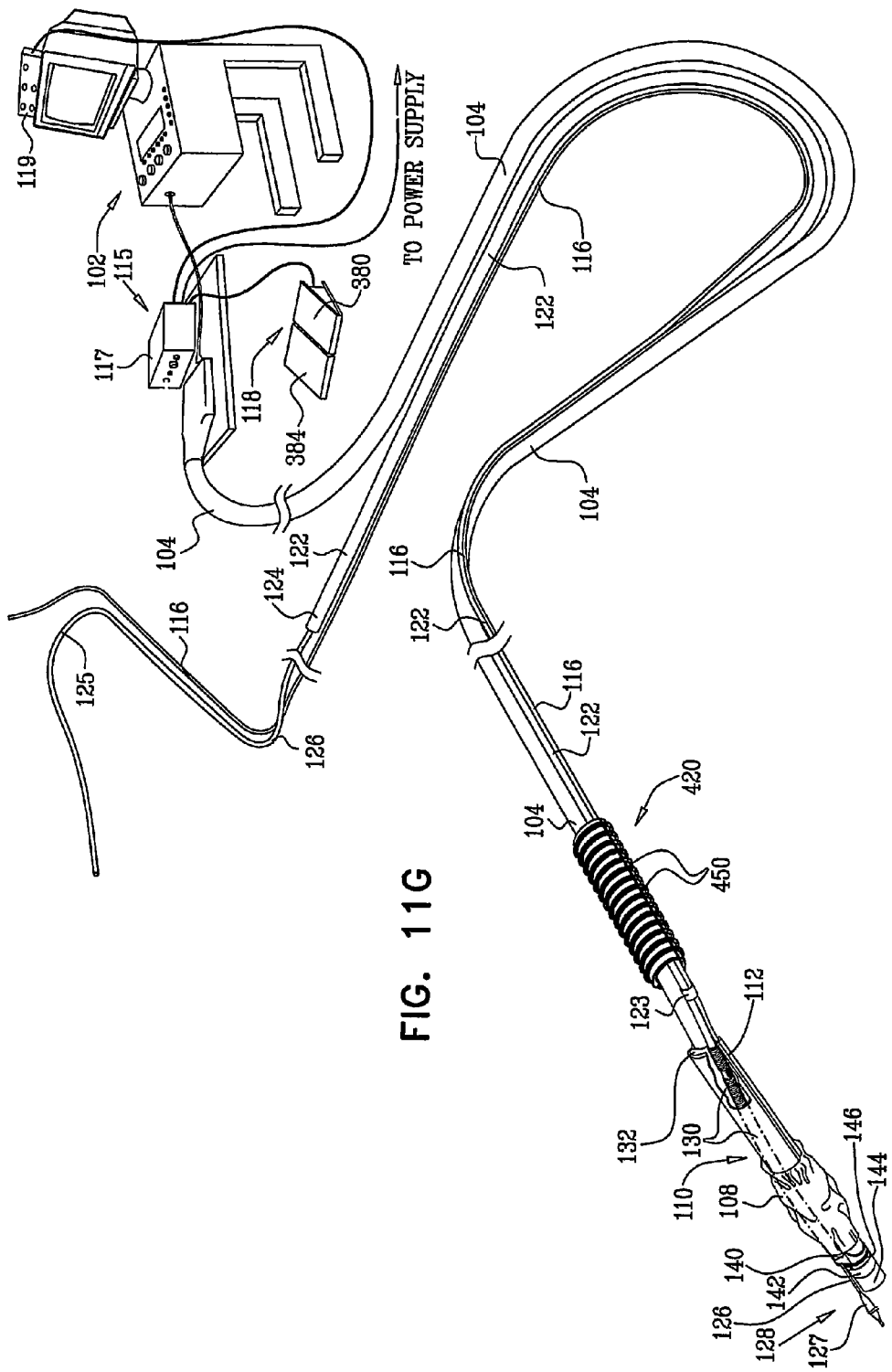
Figure 11I:
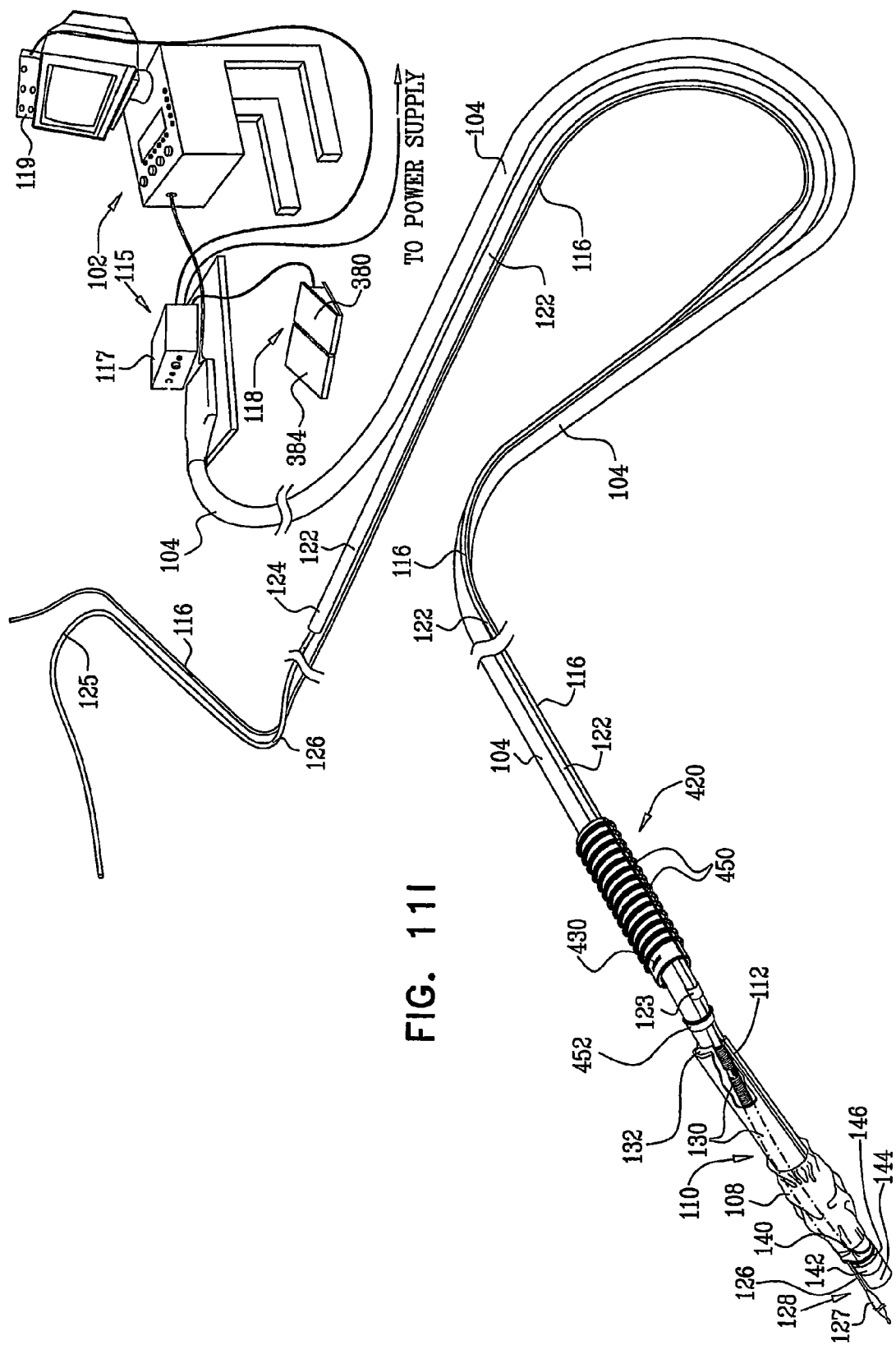
Figure 11J:
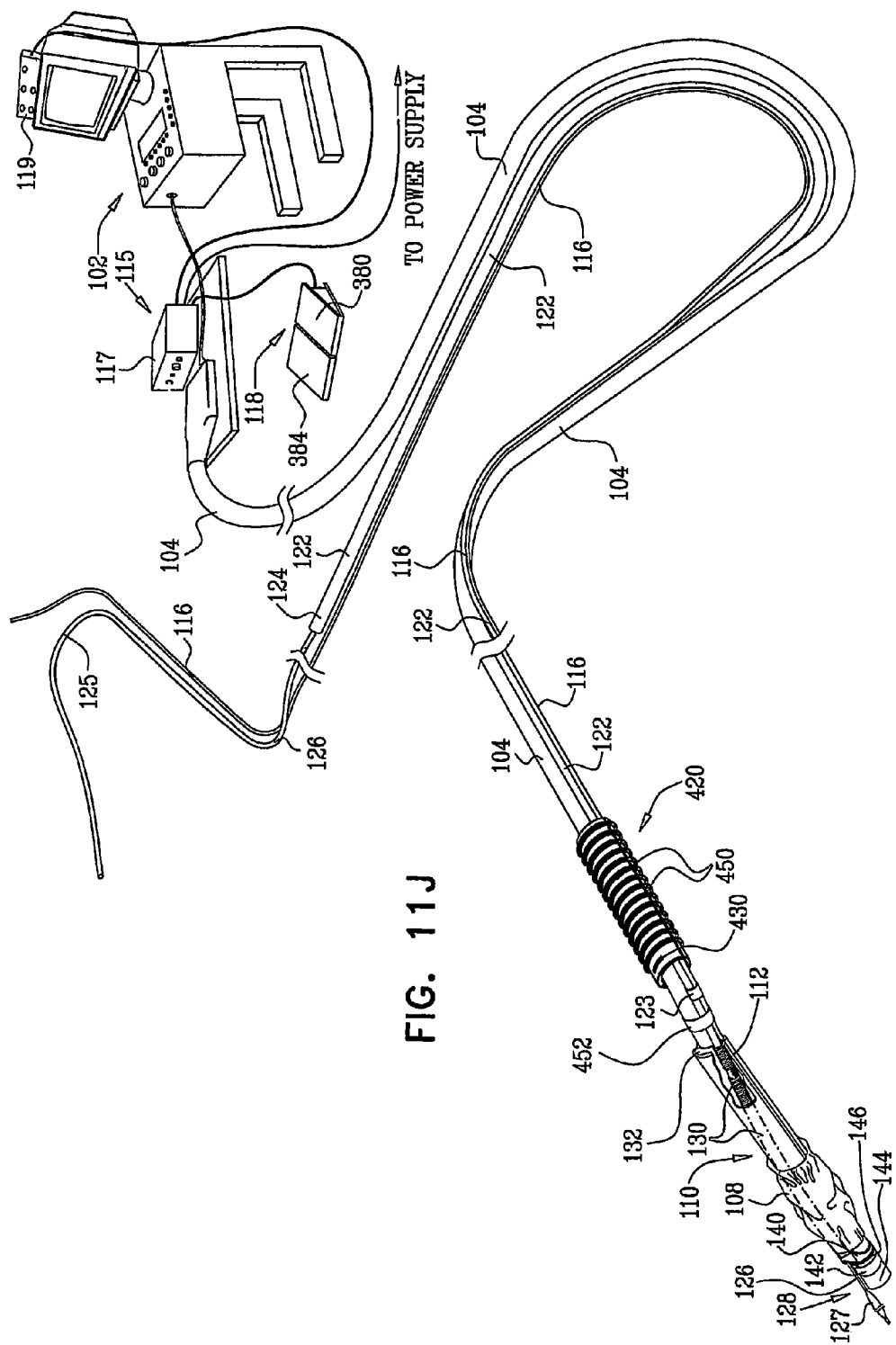
Figure 11K:
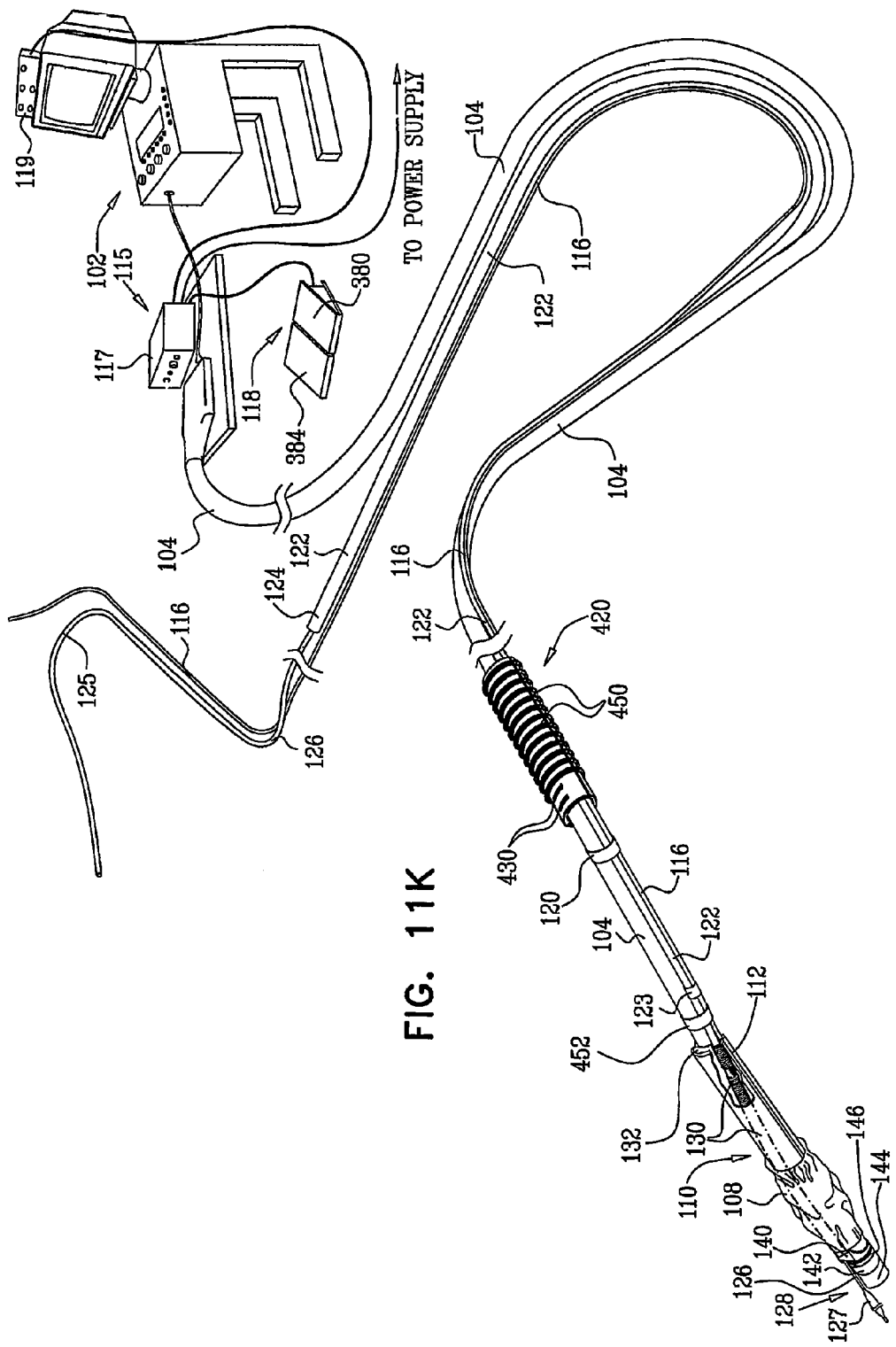
Figure 11L:
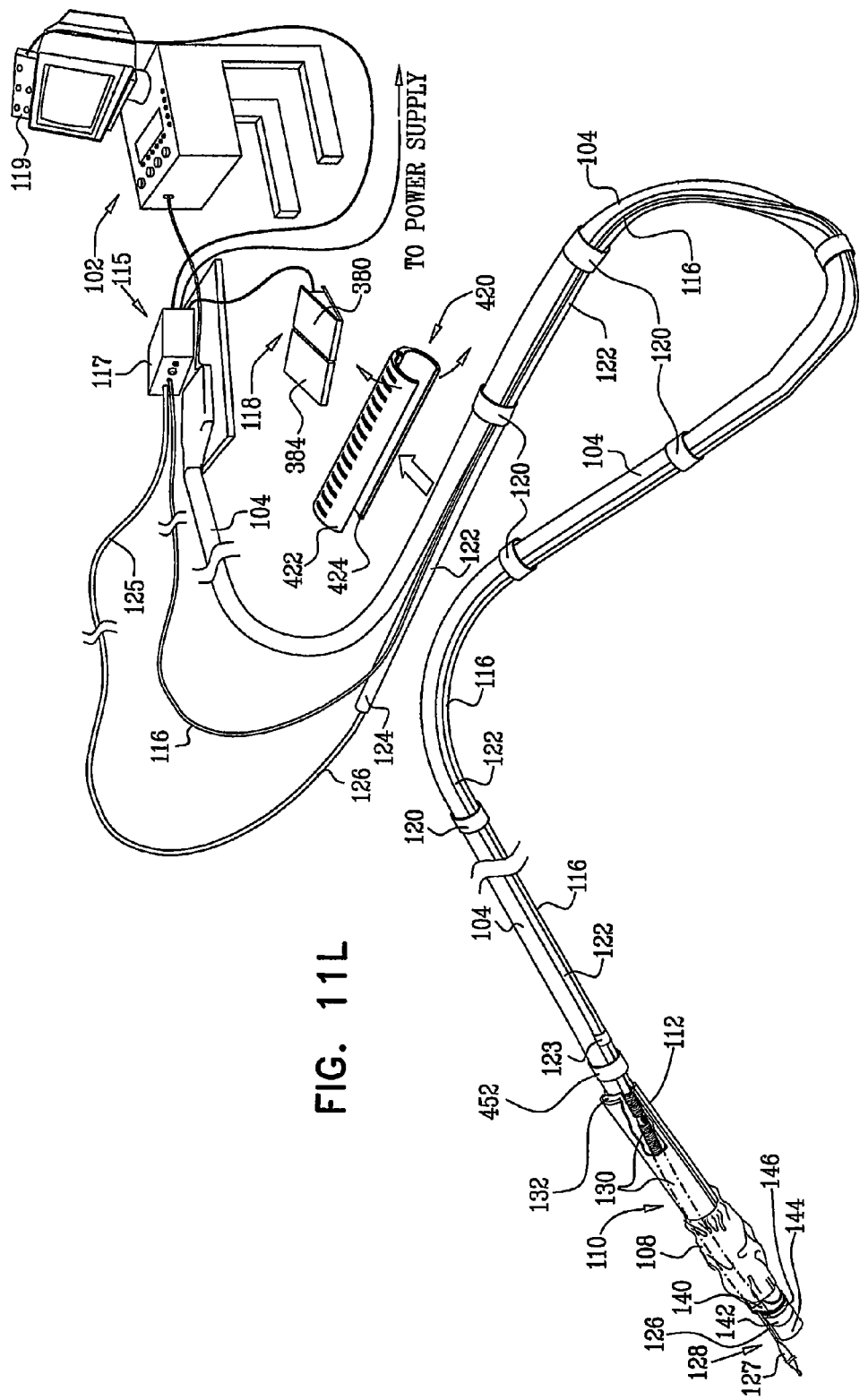

FIG. 11G shows loaded flexible band holder 420 positioned adjacent distal end 144 of endoscope 104. FIG. 11H shows a first one of rolled flexible bands 450, designated by reference numeral 452, rolled off of band holder 420 onto endoscope 104 and tubes 116 and 122. FIG. 11I shows band 452 partially unrolled and FIG. 11J shows band 452 fully unrolled in a desired position holding together endoscope 104 and tubes 116 and 122. FIG. 11K shows placement of another band 120, holding together endoscope 104 and tubes 116 and 122 and FIG. 11L shows placement of all of the flexible bands 120 holding together endoscope 104 and tubes 116 and 122, and hinged opening of flexible band holder 420 and disengagement thereof from endoscope 104 and tubes 116 and 122.

It is a particular feature of the present invention to afford attachment of tubes, such as tubes 116 and 122, to an endoscope, such as endoscope 104, by stretchable attachment means having endless continuous circumference, such as bands 120.

It is another particular feature of the present invention to afford attachment of tubes 116 and 126 to endoscope 104 by stretchable bands 120 having endless continuous circumference, wherein the maximally stretched circumference of bands 120 is smaller than the maximal circumference of flexible endoscope assembly and of the proximal portion of endoscope 104.

Reference is now made to FIGS. 12A and 12B, which are simplified assembled and exploded view illustrations of endoscope tool driving assembly 410 (FIG. 8). The endoscope tool driving assembly 410 is illustrated in FIGS. 12A and 12B together with tube 126 which extends through tube 122 and out from proximal end 124 thereof.

As seen in FIGS. 12A and 12B, the endoscope tool driving assembly 410 preferably comprises an elongate integrally hinged clamp 500 which is partially longitudinally bifurcated by transverse slots 501 into a fixed tube engagement portion 502, which engages tube 122, and a selectable tube clamping portion 504, which selectably, in response to squeezing engagement of a user's hand, clamps tube 126.

Fixed tube engagement portion 502 of clamp 500 comprises a pair of elongated tapered walls 510 and 512 which extend outwardly from an integrally formed elongated hinge 514 and define together therewith an elongated recess 516 configured and sized to slidably engage proximal end 124 of tube 122.

Selectable tube clamping portion 504 of clamp 500 comprises a pair of elongated tapered walls 520 and 522, integrally formed with respective walls 510 and 512 and partially separated therefrom by slots 501, which extend outwardly from an integrally formed elongated hinge 524, integrally formed with hinge 514, and define together therewith an elongated recess 526 configured and sized to selectably clamp tube 126. A shoulder 527 is defined between elongate recess 516 and elongate recess 526.

Preferably, tapered walls 510 and 512 are formed at corners thereof with retaining apertures 528, which are located, configured and sized to accommodate corresponding protrusions 530, formed on a locking member 532. Normally, tapered walls 510 and 512 are forced apart, as shown in FIG. 12A, to permit insertion of tube 122 in recess 514, and are then allowed to return to their steady-state mutual orientation, shown in FIG. 12B, following insertion of tubes 122 and 126 and locking insertion of locking member 532 between tapered walls 510 and 512, such that protrusions 530 engage apertures 528. It is noted that in the operative orientation of the endoscope tool driving assembly 410 shown in FIG. 12B, tapered walls 520 and 522 do not clamp tube 126 but are sufficiently flexible to provide clamping of tube 126 when squeezed by a user's hand.

Reference is now made to FIGS. 13A, 13B, 13C, 13D, 13E, 13F and 13G, which are simplified illustrations of operation of the flexible endoscope system of FIGS. 1A and 1B.

Figure 13A:
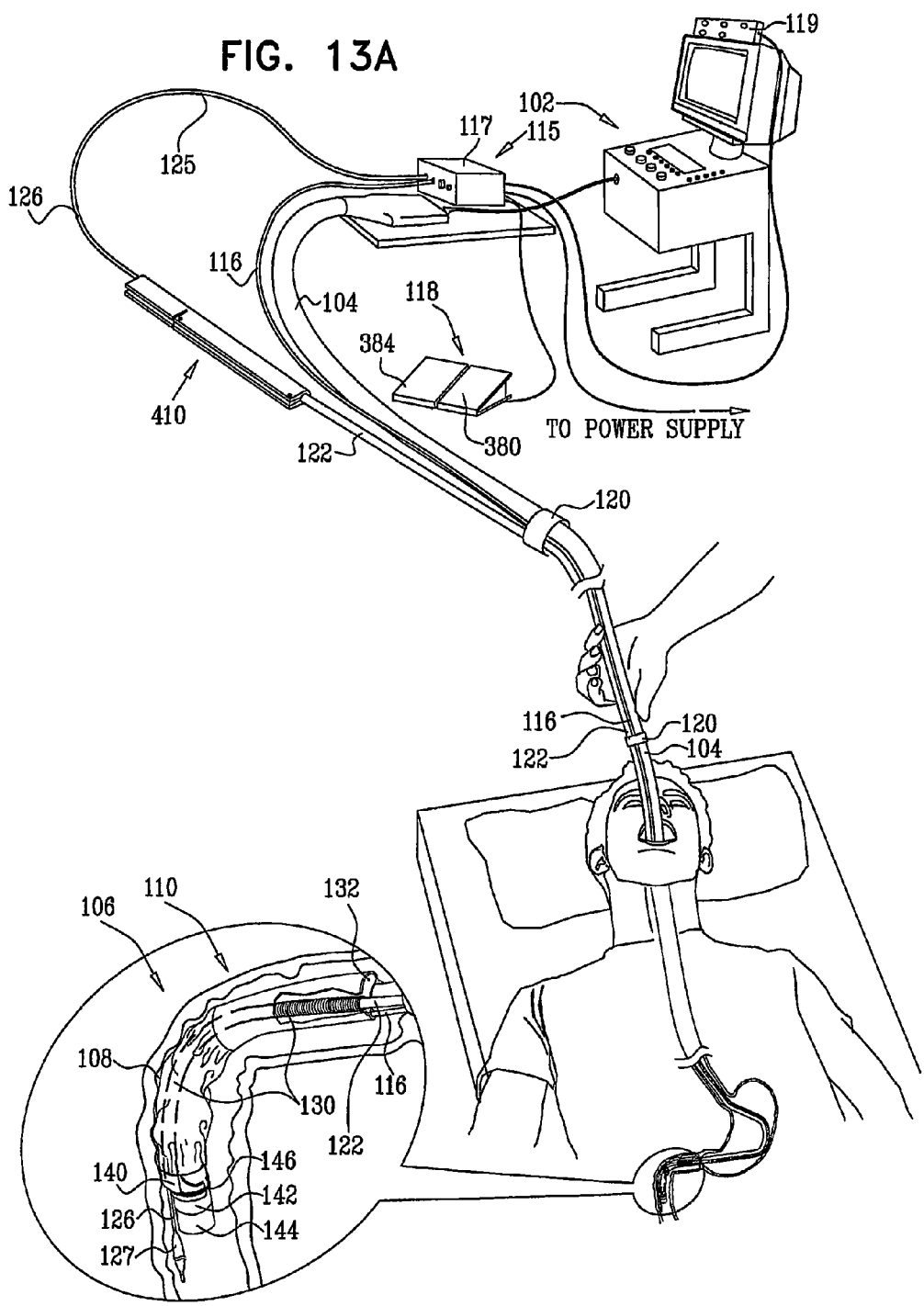

FIG. 13A shows insertion of the flexible endoscope assembly, including endoscope 104, tube 116, tube 126, external tube 122, tubular sleeve 110, forward collar element 140 and auxiliary endoscopy assembly 106 into the small intestine of a patient.

Figure 13B:
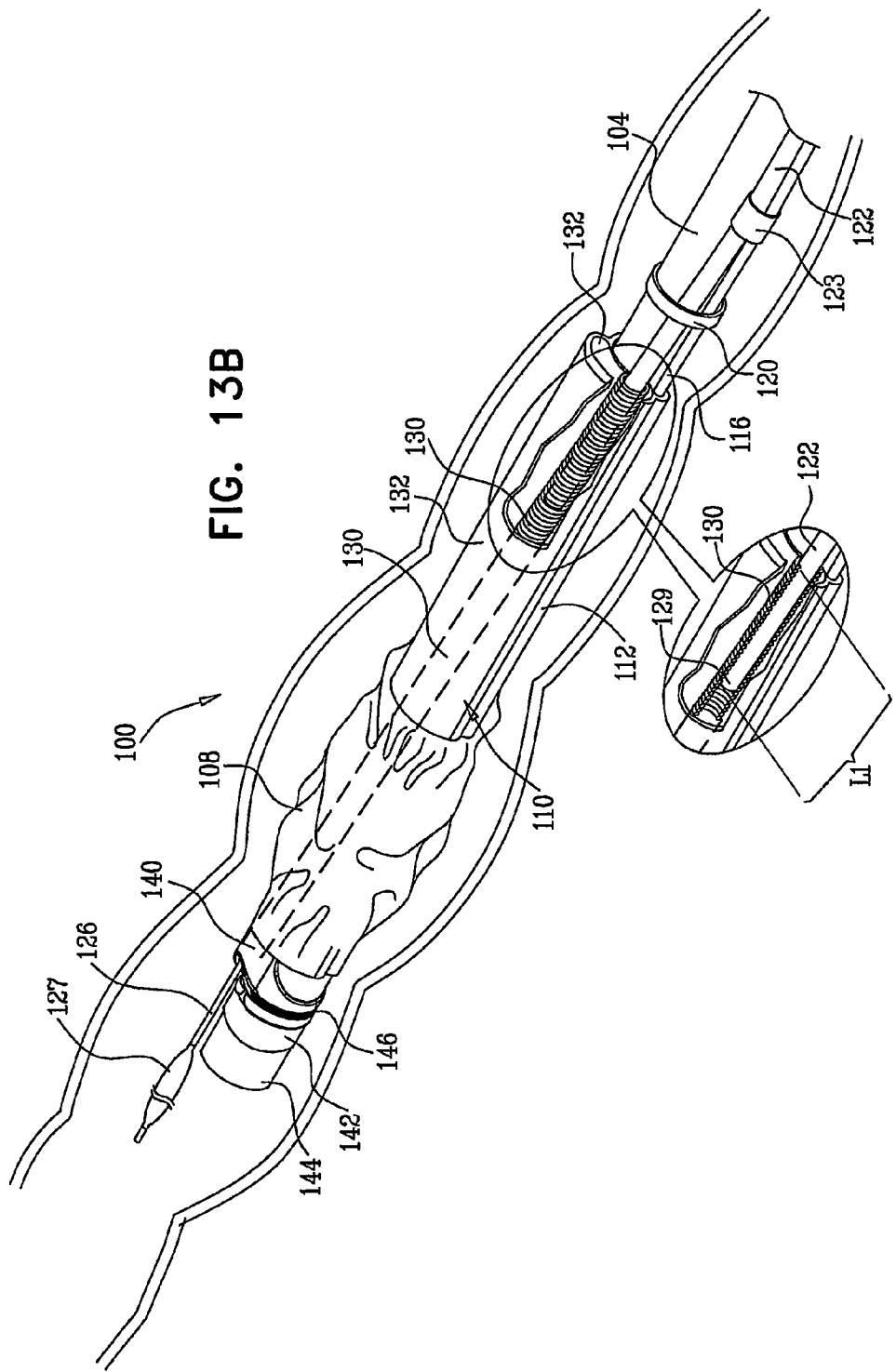
Figure 13D:
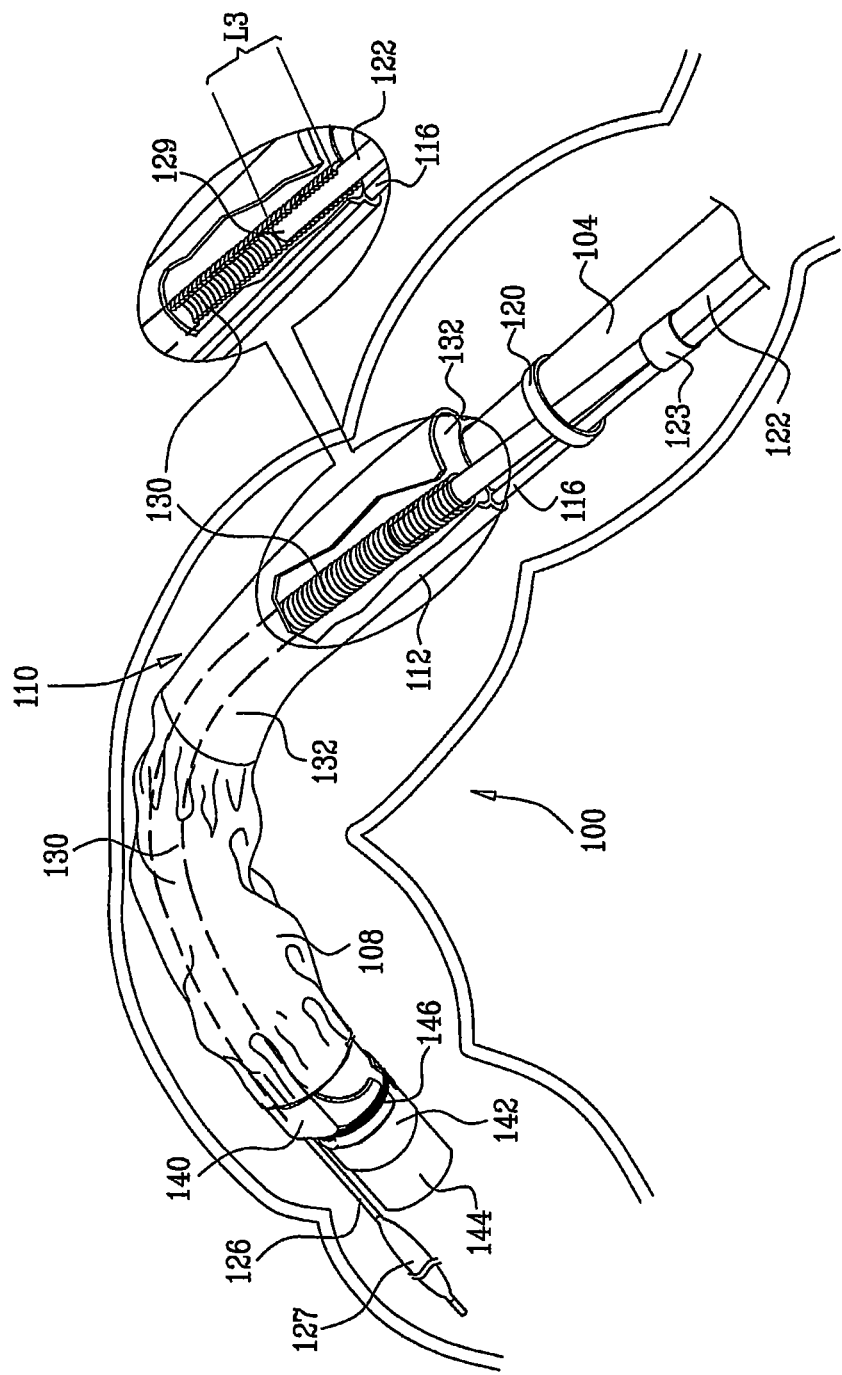

FIGS. 13B, 13C and 13D together illustrate bending of the flexible endoscope assembly. FIG. 13B shows the endoscope assembly along a relatively straight portion of the small intestine. It is seen that in this situation the distal end 129 of tube 122 typically extends into spring 130 by a first amount, here designated L1. It is also seen that spring 130 typically enters lumen 132 at the left side thereof in the sense of FIG. 13B and exits the lumen 132 at the right side thereof in the sense of FIG. 13B. This is seen with clarity in Section A-A of FIG. 1A.

FIG. 13C illustrates the flexible endoscope assembly located at an upwardly curving portion of the small intestine. It is seen that in this situation the distal end 129 of tube 122 typically extends into spring 130 by a second amount, here designated L2, which is typically more than the L1. It is also seen that spring 130 typically enters lumen 132 at the right side thereof in the sense of FIG. 13B and exits the lumen 132 at the right side thereof in the sense of FIG. 13B.

FIG. 13D illustrates the flexible endoscope assembly located at a downwardly curving portion of the small intestine. It is seen that in this situation the distal end 129 of tube 122 typically extends into spring 130 by a third amount, here designated L3, which is typically less than the L1. It is also seen that spring 130 typically enters lumen 132 at the left side thereof in the sense of FIG. 13B and exits the lumen 132 at the right side thereof in the sense of FIG. 13B.

It is appreciated that L1 is large enough to prevent distal end 129 of external tube 122 from sliding out of spring 130 if endoscope 104 is bent downwardly to its minimum radius of curvature. For example, L1 may be in the range of 2-4 centimeters.

The amount L1 is fixed by attaching external tube 122 to tube 116 by band 123 (FIG. 1A).

It is appreciated that the slidable positioning of distal end 129 of external tube 122 within spring 130, as well as the ability of spring 130 to change its orientation within saddle-type lumen 132 of tubular assembly 110, increase the flexibility of the flexible endoscope assembly, and reduce or eliminate resistance of tubular assembly 110, external tube 122 and spring 130 to bending of endoscope 104, such as during in vivo operation illustrated in FIGS. 13C and 13D.

Figure 13E:
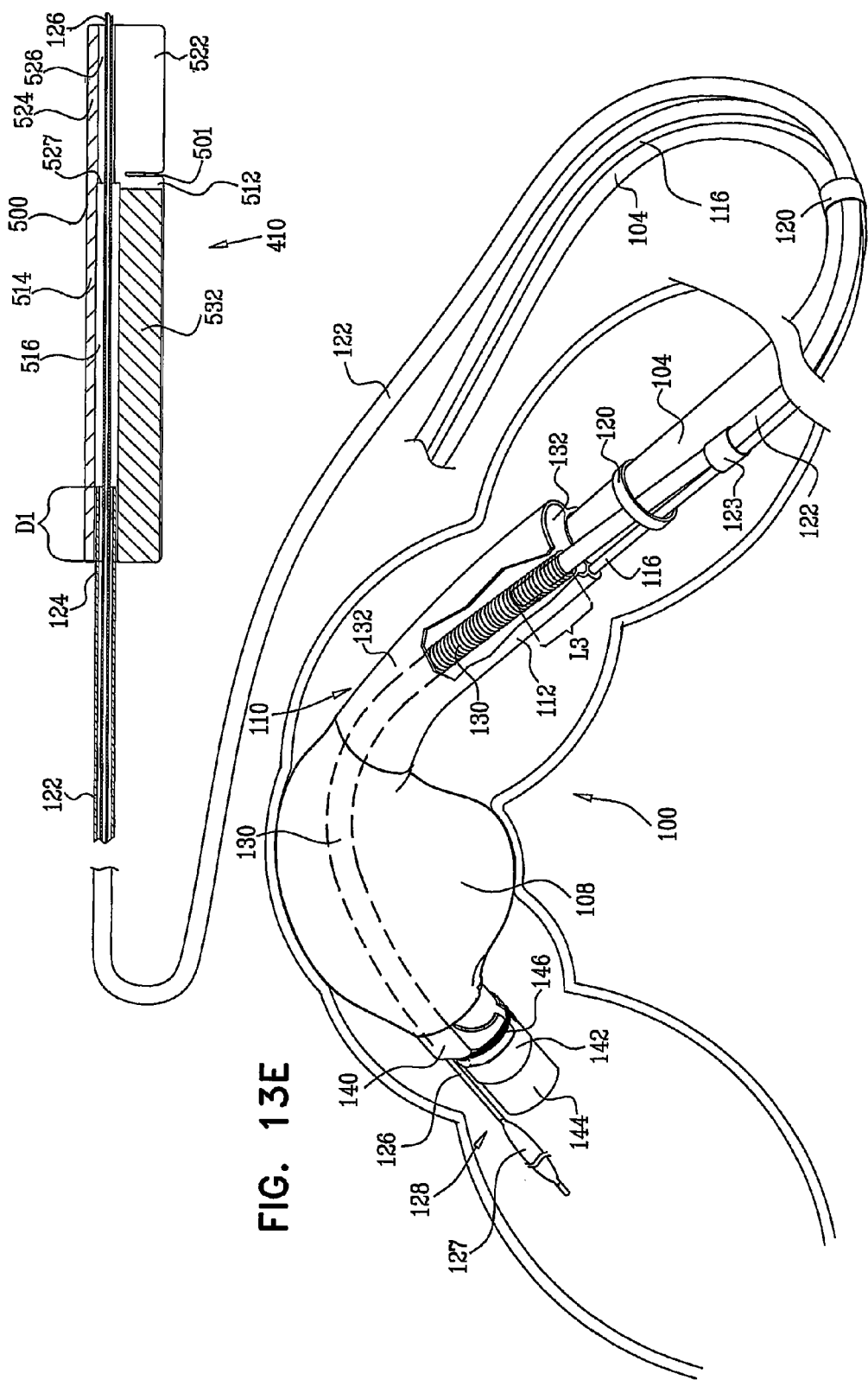

FIG. 13E illustrates the flexible endoscope assembly arranged generally as shown in FIG. 13D but having balloon 108 inflated so as to anchor the flexible endoscope assembly within the small intestine. It is seen that endoscope tool driving assembly 410 is propositioned with respect to proximal end 124 of tube 122 but does not clamp tube 126. Proximal end 124 extends to a length designated by D1 within clamp 500.

Figure 13F:
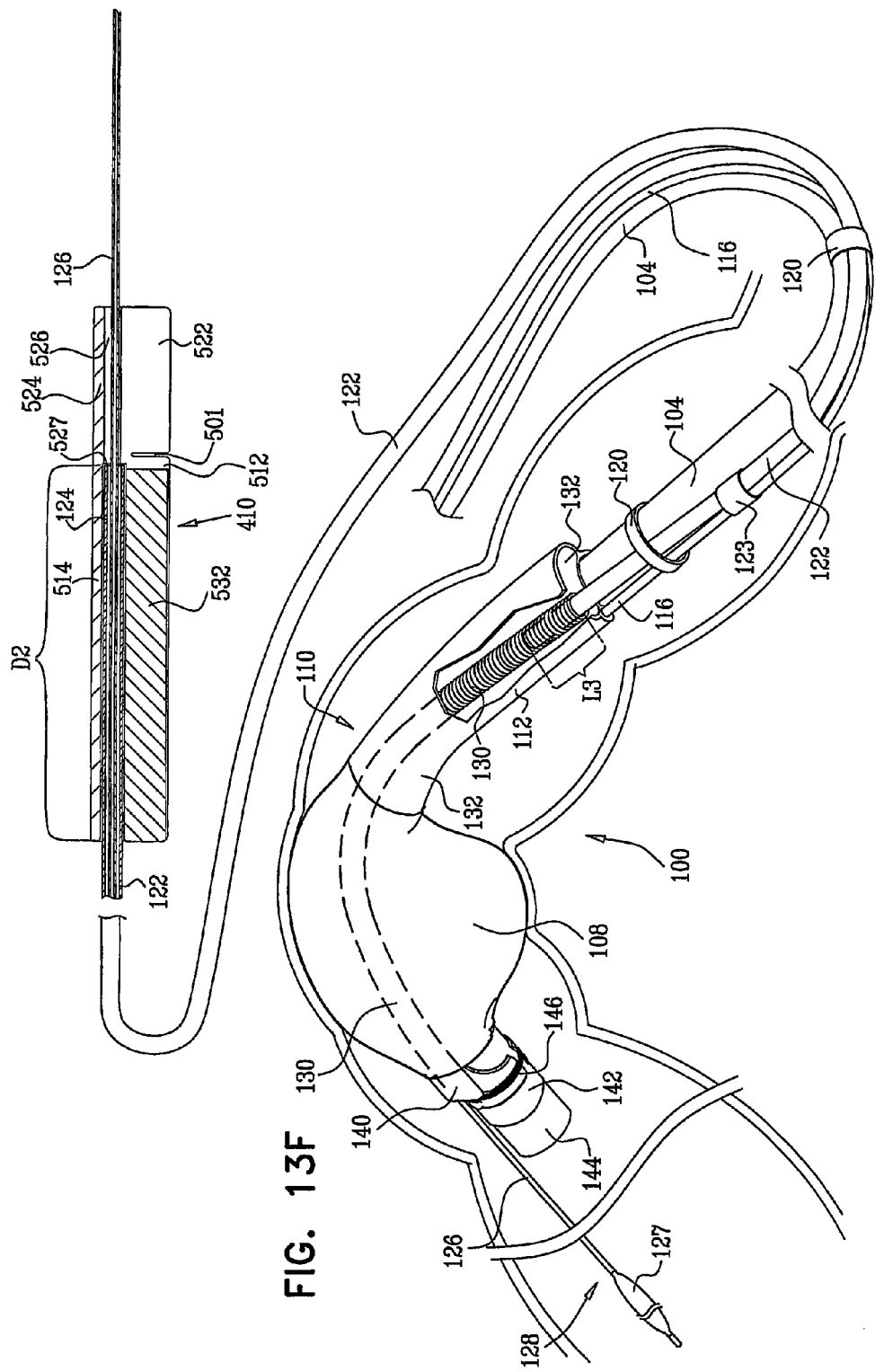

FIG. 13F illustrates the flexible endoscope assembly arranged generally as shown in FIGS. 13D and 13E but having endoscope tool 128 and balloon 127 moved forwardly with respect to the remainder of the flexible endoscope assembly within the small intestine. It is seen that proximal end 124 of tube 122 engages shoulder 527 and extends to a length designated by D2, which is greater than D1, within clamp 500.

The transition between the operative orientations of FIGS. 13E and 13F is effected preferably by an operator holding tube 122 in one hand and squeezing selectable tube clamping portion 504 of clamp 500 into clamping engagement with tube 126. The user employs clamp 500 to force the tube 126 forwardly relative to tube 122, thereby forcing the endoscope tool 128 forward with respect to the remainder of the flexible endoscope assembly.

Figure 13G:
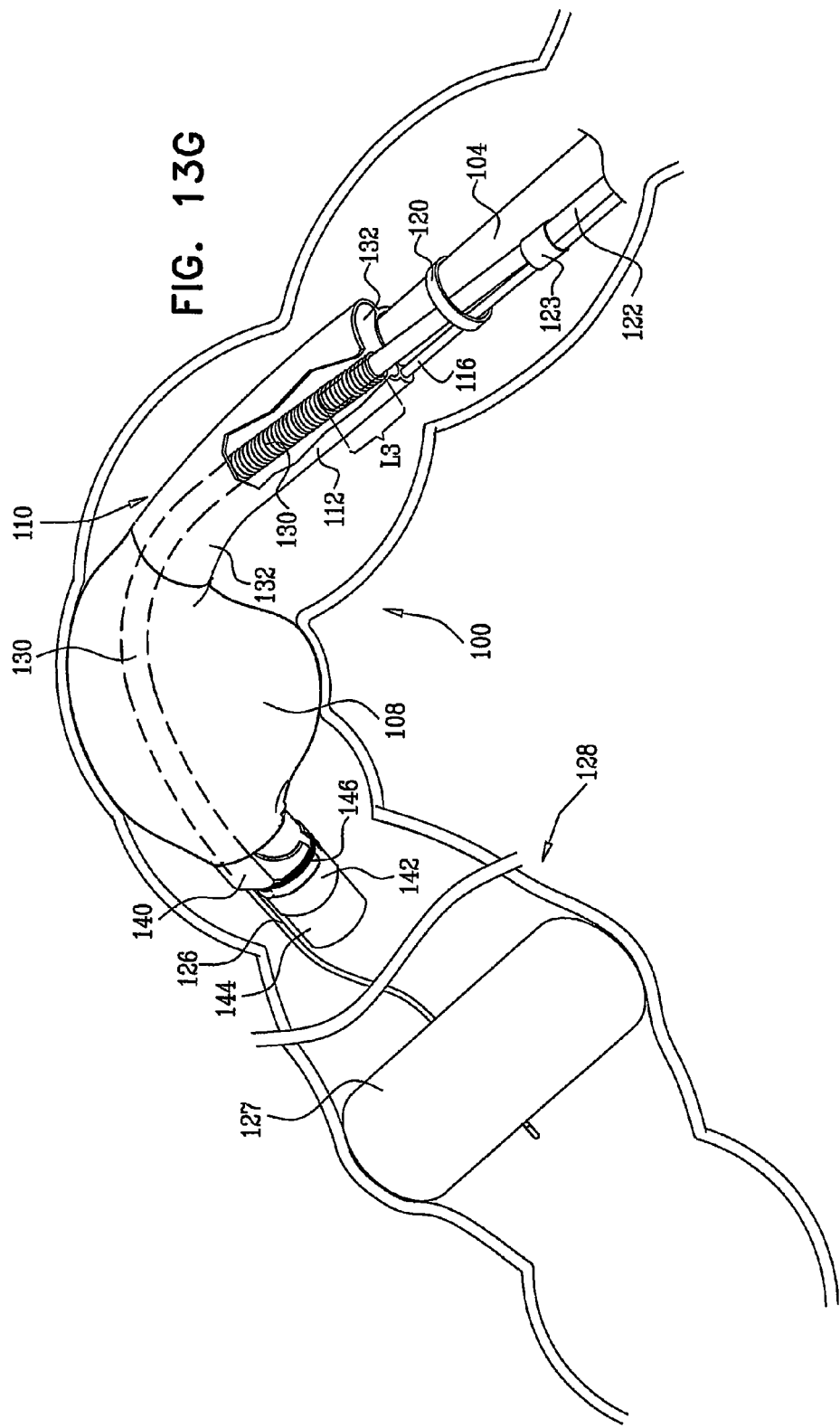

FIG. 13G illustrates the flexible endoscope assembly arranged generally as shown in FIG. 13F but having balloon 127 inflated for anchoring engagement of endoscope tool 128 with the small intestine.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

The invention claimed is:

1. An enhanced flexibility auxiliary endoscope assembly for use with an endoscope having an instrument channel, the assembly comprising:

a coil spring; and a flexible sleeve having a first lumen for accommodating a distal portion of an endoscope having an instrument channel, each of said sleeve, said first lumen, said endoscope and said instrument channel being capable of assuming at least a first curvature, and a second lumen for accommodating said coil spring, said second lumen having a generally saddle-shaped cross-section, said second lumen being configured to allow said coil spring to assume said at least first curvature as well as at least a second curvature about said first curvature, thereby to enhance flexibility of said auxiliary endoscope assembly, and said coil spring lying radially outside said first lumen and being angularly misaligned with respect to said first lumen when said endoscope is assuming said at least a first curvature.

2. An enhanced flexibility auxiliary endoscope assembly according to claim 1 and also comprising an inflatable balloon mounted onto said flexible sleeve.

3. An enhanced flexibility auxiliary endoscope assembly according to claim 1 and also comprising a channel which is defined at least in part by said coil spring.

4. An enhanced flexibility auxiliary endoscope assembly according to claim 1 and also comprising a collar operative to secure together at least said endoscope, said coil spring and said flexible sleeve.

5. An enhanced flexibility auxiliary endoscope assembly according to claim 1 and wherein:

said coil spring has an outer cross section having a diameter; and said first lumen is configured for accommodating said distal portion of said endoscope which is capable of assuming said at least a first curvature and said second lumen is configured to define, at least along a portion of an elongate extent thereof, an elongate element transverse displacement accommodating volume having a transverse extent at least twice as long as said diameter of said outer cross section of said coil spring.

6. An enhanced flexibility auxiliary endoscope assembly according to claim 2 and also comprising an inflation control subassembly operative to facilitate at least one of inflation and deflation of said inflatable balloon.

7. An enhanced flexibility auxiliary endoscope assembly according to claim 2 and wherein said at least one flexible elongate element comprises a channel and an endoscope tool which extends through said channel and includes an inflatable endoscope tool balloon and also comprising at least one inflation control subassembly operative to facilitate at least one of inflation and deflation of at least one of said inflatable balloon and said inflatable endoscope tool balloon and wherein said at least one inflation control subassembly comprises initialization functionality operative to ensure that prior to operation at least one of said inflatable balloon and said inflatable endoscope tool balloon is in a fully deflated state.

8. An enhanced flexibility auxiliary endoscope assembly according to claim 3 and also comprising an endoscope tool which extends through said channel and includes an inflatable endoscope tool balloon.

9. An enhanced flexibility auxiliary endoscope assembly according to claim 3 and wherein said channel comprises at least first and second mutually telescoping channel elements.

10. An enhanced flexibility auxiliary endoscope assembly according to claim 3 and wherein said channel comprises:

an elongate channel element arranged for mounting on of said endoscope, said coil spring being arranged to receive said elongate channel element to a variable elongate extent, at least one of said coil spring and said elongate channel element being flexible; and said variable elongate extent varying as a function of a degree of bending of said endoscope.

11. An enhanced flexibility auxiliary endoscope assembly according to claim 3 and wherein the inner diameter of said channel is in the range of 3 -6 mm.

12. An enhanced flexibility auxiliary endoscope assembly according to claim 8 and also comprising an endoscope tool manipulator for advancing and retracting said endoscope tool.

13. An enhanced flexibility auxiliary endoscope assembly according to claim 8 and wherein said inflatable endoscope tool balloon, when in a fully deflated state, is adapted to be at least partially inserted within said channel.

14. An enhanced flexibility auxiliary endoscope assembly according to claim 8 and wherein said inflatable endoscope tool balloon is adapted to be inflated to a diameter of at least 35 mm.

15. An enhanced flexibility auxiliary endoscope assembly according to claim 4 and wherein said collar comprises a collar portion and a retaining band portion engaging said collar portion, said collar being adapted for securing endoscopes of varying cross-sectional dimensions together with said at least one flexible elongate element and said flexible sleeve.

16. An enhanced flexibility auxiliary endoscope assembly according to claim 3 and also comprising a plurality of stretchable resilient endless mounting bands engaging said endoscope and at least one of said flexible sleeve, said coil spring and said channel at spaced locations along the length thereof.

17. An enhanced flexibility endoscope system comprising:

an endoscope having an instrument channel;

a coil spring; and a flexible sleeve having a first lumen for accommodating a distal portion of said endoscope, each of said sleeve, said first lumen, said endoscope and said instrument channel being capable of assuming at least a first curvature, and a second lumen for accommodating said coil spring, said second lumen having a generally saddle-shaped cross-section, said second lumen being configured to allow said coil spring to assume said at least first curvature as well as at least a second curvature about said first curvature, thereby to enhance flexibility of said endoscope system, and said coil spring lying radially outside said first lumen and being angularly misaligned with respect to said first lumen when said endoscope is assuming said at least a first curvature.

18. An enhanced flexibility endoscope system according to claim 17 and also comprising an endoscope tool which extends through said coil spring and includes an inflatable endoscope tool balloon.

19. An enhanced flexibility endoscope system according to claim 17 and also comprising:

an elongate channel element arranged for mounting on said endoscope, said coil spring being arranged to receive said elongate channel element to a variable elongate extent, at least one of said coil spring and said elongate channel element being flexible; and said variable elongate extent varying as a function of a degree of bending of said endoscope.

20. An enhanced flexibility endoscope system according to claim 18 and also comprising at least one inflation control subassembly operative to facilitate at least one of inflation and deflation of said inflatable endoscope tool balloon.

21. An enhanced flexibility endoscope system according to claim 20 and wherein said at least one inflation control subassembly comprises initialization functionality operative to ensure that prior to operation said inflatable endoscope tool balloon is in a fully deflated state.

22. An enhanced flexibility endoscope system according to claim 19 and also comprising an endoscope tool which extends through said coil spring and said elongate channel element and includes an inflatable endoscope tool balloon.

23. An enhanced flexibility endoscope system according to claim 22 and also comprising at least one inflation control subassembly operative to facilitate at least one of inflation and deflation of said inflatable endoscope tool balloon and wherein said at least one inflation control subassembly comprises initialization functionality operative to ensure that prior to operation said inflatable endoscope tool balloon is in a fully deflated state.

24. An enhanced flexibility auxiliary endoscope assembly according to claim 16 and wherein said plurality of stretchable resilient endless mounting bands each have an endless continuous circumference, wherein the maximally stretched circumference of at least one of said bands is smaller than the maximal circumference of said auxiliary endoscope assembly and of a proximal portion of said endoscope.

* * * * *